(12) United States Patent
Delisa et al.

(10) Patent No.: US 9,322,023 B2
(45) Date of Patent: Apr. 26, 2016

(54) CONSTRUCTS AND METHODS FOR THE ASSEMBLY OF BIOLOGICAL PATHWAYS

(71) Applicant: Cornell University, Ithaca, NY (US)

(72) Inventors: Matthew Delisa, Ithaca, NY (US); Robert Conrado, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 13/647,898

(22) Filed: Oct. 9, 2012

(65) Prior Publication Data

US 2013/0130347 A1  May 23, 2013

Related U.S. Application Data

(60) Provisional application No. 61/544,047, filed on Oct. 6, 2011.

(51) Int. Cl.

| | |
|---|---|
| *C12N 15/115* | (2010.01) |
| *C12N 9/96* | (2006.01) |
| *C12N 15/63* | (2006.01) |
| *C12N 1/00* | (2006.01) |
| *C12N 1/14* | (2006.01) |
| *C12N 1/20* | (2006.01) |
| *C12N 5/04* | (2006.01) |
| *C12N 5/07* | (2010.01) |
| *C12N 15/11* | (2006.01) |
| *C12N 15/52* | (2006.01) |
| *C12P 7/22* | (2006.01) |

(Continued)

(52) U.S. Cl.
CPC ............... *C12N 15/115* (2013.01); *C12N 1/00* (2013.01); *C12N 1/14* (2013.01); *C12N 1/20* (2013.01); *C12N 5/04* (2013.01); *C12N 5/06* (2013.01); *C12N 9/96* (2013.01); *C12N 15/11* (2013.01); *C12N 15/52* (2013.01); *C12N 15/63* (2013.01); *C12P 7/18* (2013.01); *C12P 7/22* (2013.01); *C12P 7/42* (2013.01); *C07K 2319/80* (2013.01); *C07K 2319/81* (2013.01); *C12N 2310/13* (2013.01); *C12N 2310/51* (2013.01)

(58) Field of Classification Search
None
See application file for complete search history.

(56) References Cited

U.S. PATENT DOCUMENTS

2009/0075392 A1* 3/2009 Colyer ......................... 436/501
2011/0008829 A1   1/2011 Dueber et al.

FOREIGN PATENT DOCUMENTS

| WO | WO 9856904 A1 * | 12/1998 |
| WO | WO 2009108774 A2 * | 9/2009 |

(Continued)

OTHER PUBLICATIONS

Fierobe et al., "Design and production of active cellulosome chimeras. Selective incorporation of dockerin-containing enzymes into defined functional complexes", Journal of Biological Chemistry, vol. 276, No. 24, pp. 21257-21261, 2001.*

(Continued)

*Primary Examiner* — Tekchand Saidha
*Assistant Examiner* — Richard Ekstrom
(74) *Attorney, Agent, or Firm* — LeClairRyan, a Professional Corporation

(57) ABSTRACT

The present invention is directed to a synthetic nucleic acid scaffold comprising one or more subunits, each subunit comprising two or more different protein-binding sequences coupled together. The present invention further relates to systems and methods for assembling a synthetic biological pathway and producing a biological pathway product or a precursor product using the synthetic nucleic acid scaffold.

29 Claims, 17 Drawing Sheets

(51) Int. Cl.
    C12P 7/18    (2006.01)
    C12P 7/42    (2006.01)

(56) References Cited

FOREIGN PATENT DOCUMENTS

WO    WO2012053985 A1 *   4/2012
WO    WO 2013006762 A2 *  1/2013

OTHER PUBLICATIONS

Muller et al., "DNA-directed assembly of artificial multienzyme complexes", Biochemical and Biophysical Research Communications, vol. 377, pp. 62-67, 2008.*

Numajiri et al., "Discrete and active enzyme nanoarrays on DNA origami scaffolds purified by affinity tag separation", Journal American Chemical Socieity, vol. 132, No. 29, pp. 9937-9939, 2010; published on Web Jun. 30, 2010.*

Chen et al., "Designing biological compartmentalization", Trends in Cell Biology, vol. 22, No. 12, pp. 662-670, 2012.*

Conrado et al., "Engineering the spatial organization of metabolic enzymes: mimicking nature's synergy", Current Opinion in Biotechnology, vol. 19, pp. 492-499, 2008.*

Dueber et al., "Synthetic protein scaffolds provide modular control over metabolic flux" Nature Biotechnology, vol. 27, No. 8, pp. 753-759, 2009.*

Bulyk et al., "Exploring the DNA-Binding Specificities of Zinc Fingers With DNA Microarrays," Proc. Nat'l. Acad. Sci. U.S.A. 98(13):7158-7163 (2001).

Conrado et al., "DNA-Guided Assembly of Biosynthetic Pathways Promotes Improved Catalytic Efficiency," Nucleic Acids Res. 40(4):1879-1889 (2012).

Delebecque et al., "Organization of Intracellular Reactions With Rationally Designed RNA Assemblies," Science 333:470-474 (2011).

Kim et al., "A Zinc Finger Protein Array for the Visual Detection of Specific DNA Sequences for Diagnostic Applications," Nucleic Acids Res. 39(5):e29 (9 pages) (2011).

Krishna et al., "Survey and Summary: Structural Classification of Zinc Fingers," Nucleic Acids Res. 31(2):532-550 (2003).

* cited by examiner

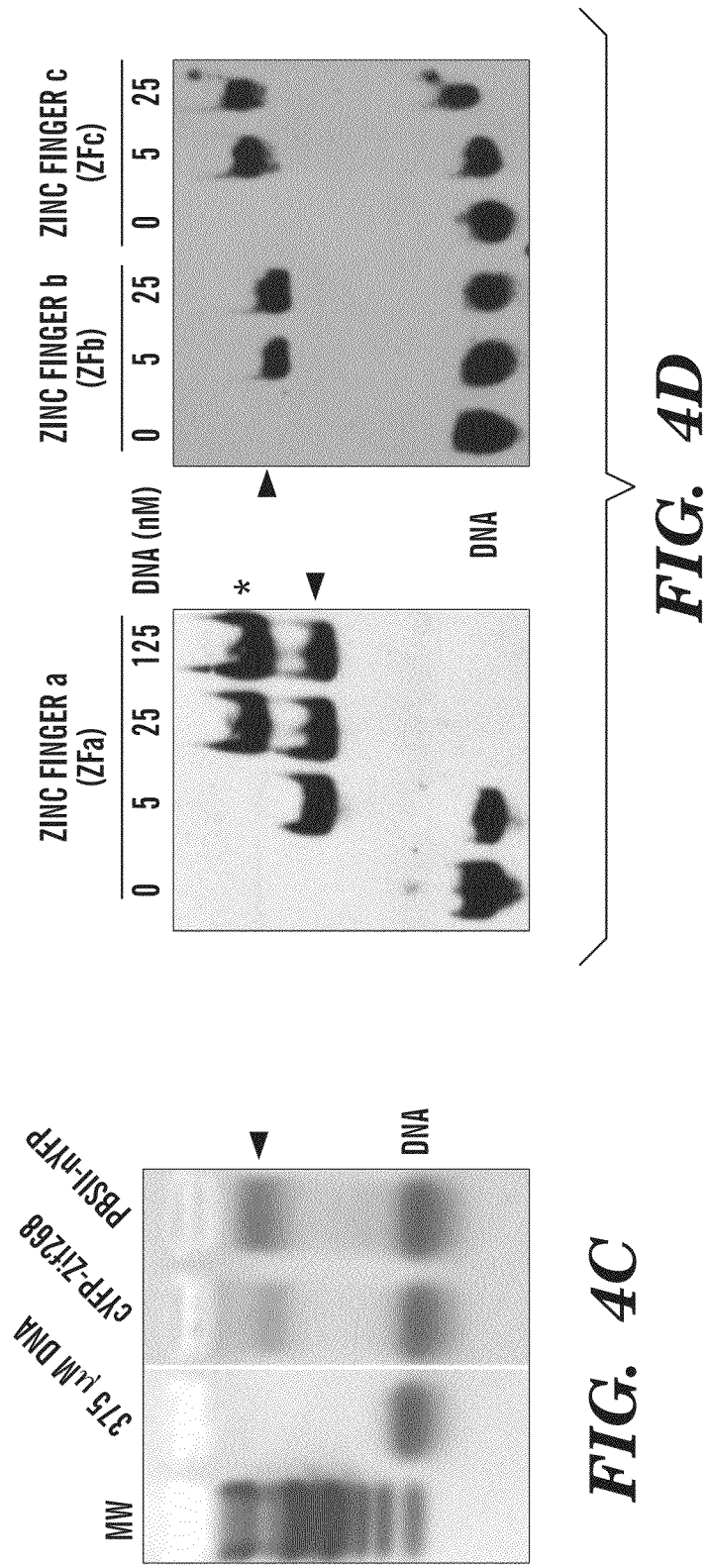

US 9,322,023 B2

SEQUENCE LISTING

```
<160> NUMBER OF SEQ ID NOS: 51

<210> SEQ ID NO 1
<211> LENGTH: 9
<212> TYPE: DNA
<213> ORGANISM: Artificial
<220> FEATURE:
<223> OTHER INFORMATION: Zif268 protein binding sequence

<400> SEQUENCE: 1 gcgtgggcg                                                              9

<210> SEQ ID NO 2
<211> LENGTH: 9
<212> TYPE: DNA
<213> ORGANISM: Artificial
<220> FEATURE:
<223> OTHER INFORMATION: Zif268 protein binding sequence

<400> SEQUENCE: 2 gcggggcg                                                               9

<210> SEQ ID NO 3
<211> LENGTH: 9
<212> TYPE: DNA
<213> ORGANISM: Artificial
<220> FEATURE:
<223> OTHER INFORMATION: PBSII protein binding sequence

<400> SEQUENCE: 3 gtgtggaaa                                                              9

<210> SEQ ID NO 4
<211> LENGTH: 9
<212> TYPE: DNA
<213> ORGANISM: Artificial
<220> FEATURE:
<223> OTHER INFORMATION: ZFa protein binding sequence

<400> SEQUENCE: 4
```

```
gtcgatgcc                                                              9

<210> SEQ ID NO 5
<211> LENGTH: 9
<212> TYPE: DNA
<213> ORGANISM: Artificial
<220> FEATURE:
<223> OTHER INFORMATION: ZFb protein binding sequence

<400> SEQUENCE: 5 gcggctggg                                                              9

<210> SEQ ID NO 6
<211> LENGTH: 9
<212> TYPE: DNA
<213> ORGANISM: Artificial
<220> FEATURE:
<223> OTHER INFORMATION: ZFc protein binding sequence

<400> SEQUENCE: 6 gaggacggc                                                              9

<210> SEQ ID NO 7
<211> LENGTH: 9
<212> TYPE: DNA
<213> ORGANISM: Artificial
<220> FEATURE:
<223> OTHER INFORMATION: Tyr123 protein binding sequence

<400> SEQUENCE: 7 gtggatgac                                                              9

<210> SEQ ID NO 8
<211> LENGTH: 9
<212> TYPE: DNA
<213> ORGANISM: Artificial
<220> FEATURE:
<223> OTHER INFORMATION: Tyr456 protein binding sequence

<400> SEQUENCE: 8 gaaggggaa                                                              9

<210> SEQ ID NO 9
<211> LENGTH: 9
<212> TYPE: DNA
<213> ORGANISM: Artificial
<220> FEATURE:
<223> OTHER INFORMATION: Blues protein binding sequence

<400> SEQUENCE: 9 gtttggatg                                                              9

<210> SEQ ID NO 10
<211> LENGTH: 9
<212> TYPE: DNA
<213> ORGANISM: Artificial
<220> FEATURE:
<223> OTHER INFORMATION: Jazz protein binding sequence

<400> SEQUENCE: 10 gctgctgcg                                                              9

<210> SEQ ID NO 11
<211> LENGTH: 12
<212> TYPE: DNA
```

```
<213> ORGANISM: Artificial
<220> FEATURE:
<223> OTHER INFORMATION: Bagly protein binding sequence

<400> SEQUENCE: 11
cgggctgctg cg                                                              12

<210> SEQ ID NO 12
<211> LENGTH: 15
<212> TYPE: DNA
<213> ORGANISM: Artificial
<220> FEATURE:
<223> OTHER INFORMATION: Gli1 protein binding sequence

<400> SEQUENCE: 12
gaccacccaa gacga                                                           15

<210> SEQ ID NO 13
<211> LENGTH: 9
<212> TYPE: DNA
<213> ORGANISM: Artificial
<220> FEATURE:
<223> OTHER INFORMATION: HIVC protein binding sequence

<400> SEQUENCE: 13 gatgctgca                                                                   9

<210> SEQ ID NO 14
<211> LENGTH: 8
<212> TYPE: DNA
<213> ORGANISM: Artificial
<220> FEATURE:
<223> OTHER INFORMATION: B3 protein binding sequence

<400> SEQUENCE: 14 gacggggg                                                                    8

<210> SEQ ID NO 15
<211> LENGTH: 9
<212> TYPE: DNA
<213> ORGANISM: Artificial
<220> FEATURE:
<223> OTHER INFORMATION: N1 protein binding sequence

<400> SEQUENCE: 15 gtagaaggg                                                                   9

<210> SEQ ID NO 16
<211> LENGTH: 9
<212> TYPE: DNA
<213> ORGANISM: Artificial
<220> FEATURE:
<223> OTHER INFORMATION: Sp-1 protein binding sequence

<400> SEQUENCE: 16 ggggcgggg                                                                   9

<210> SEQ ID NO 17
<211> LENGTH: 87
<212> TYPE: PRT
<213> ORGANISM: Artificial
<220> FEATURE:
<223> OTHER INFORMATION: Zif268 DNA binding sequence

<400> SEQUENCE: 17

Pro Gly Glu Lys Pro Tyr Ala Cys Pro Val Glu Ser Cys Asp Arg Arg
```

```
1               5                   10                  15
Phe Ser Arg Ser Asp Glu Leu Thr Arg His Ile Arg Ile His Thr Gly
                20                  25                  30

Gln Lys Pro Phe Gln Cys Arg Ile Cys Met Arg Asn Phe Ser Arg Ser
                35                  40                  45

Asp His Leu Thr Thr His Ile Arg Thr His Thr Gly Glu Lys Pro Phe
    50                  55                  60

Ala Cys Asp Ile Cys Gly Arg Lys Phe Ala Arg Ser Asp Glu Arg Lys
65                  70                  75                  80

Arg His Thr Lys Ile His Thr
                85

<210> SEQ ID NO 18
<211> LENGTH: 85
<212> TYPE: PRT
<213> ORGANISM: Artificial
<220> FEATURE:
<223> OTHER INFORMATION: PBSII DNA binding sequence

<400> SEQUENCE: 18

Pro Gly Glu Lys Pro Tyr Ala Cys Pro Glu Cys Gly Lys Ser Phe Ser
1               5                   10                  15

Gln Arg Ala Asn Leu Arg Ala His Gln Arg Thr His Thr Gly Glu Lys
                20                  25                  30

Pro Tyr Lys Cys Pro Glu Cys Gly Lys Ser Phe Ser Arg Ser Asp His
                35                  40                  45

Leu Thr Thr His Gln Arg Thr His Thr Gly Glu Lys Pro Tyr Lys Cys
    50                  55                  60

Pro Glu Cys Gly Lys Ser Phe Ser Arg Ser Asp Val Leu Val Arg His
65                  70                  75                  80

Gln Arg Thr His Thr
                85

<210> SEQ ID NO 19
<211> LENGTH: 84
<212> TYPE: PRT
<213> ORGANISM: Artificial
<220> FEATURE:
<223> OTHER INFORMATION: ZFa DNA binding sequence

<400> SEQUENCE: 19

Pro Gly Glu Arg Pro Phe Gln Cys Arg Ile Cys Met Arg Asn Phe Ser
1               5                   10                  15

Asp Ser Pro Thr Leu Arg Arg His Thr Arg Thr His Thr Gly Glu Lys
                20                  25                  30

Pro Phe Gln Cys Arg Ile Cys Met Arg Asn Phe Ser Val Arg His Asn
                35                  40                  45

Leu Thr Arg His Leu Arg Thr His Thr Gly Glu Lys Pro Phe Gln Cys
    50                  55                  60

Arg Ile Cys Met Arg Asn Phe Ser Asp Arg Thr Ser Leu Ala Arg His
65                  70                  75                  80

Leu Lys Thr His

<210> SEQ ID NO 20
<211> LENGTH: 84
<212> TYPE: PRT
<213> ORGANISM: Artificial
<220> FEATURE:
<223> OTHER INFORMATION: ZFb DNA binding sequence
```

<400> SEQUENCE: 20

Pro Gly Glu Arg Pro Phe Gln Cys Arg Ile Cys Met Arg Asn Phe Ser
1               5                   10                  15

Lys Lys Asp His Leu His Arg His Thr Arg Thr His Thr Gly Glu Lys
                20                  25                  30

Pro Phe Gln Cys Arg Ile Cys Met Arg Asn Phe Ser Leu Ser Gln Thr
            35                  40                  45

Leu Lys Arg His Leu Arg Thr His Thr Gly Glu Lys Pro Phe Gln Cys
        50                  55                  60

Arg Ile Cys Met Arg Asn Phe Ser Arg Leu Asp Met Leu Ala Arg His
65                  70                  75                  80

Leu Lys Thr His

<210> SEQ ID NO 21
<211> LENGTH: 84
<212> TYPE: PRT
<213> ORGANISM: Artificial
<220> FEATURE:
<223> OTHER INFORMATION: ZFc DNA binding sequence

<400> SEQUENCE: 21

Pro Gly Glu Arg Pro Phe Gln Cys Arg Ile Cys Met Arg Asn Phe Ser
1               5                   10                  15

Ser Pro Ser Lys Leu Ile Arg His Thr Arg Thr His Thr Gly Glu Lys
                20                  25                  30

Pro Phe Gln Cys Arg Ile Cys Met Arg Asn Phe Ser Asp Gly Ser Asn
            35                  40                  45

Leu Ala Arg His Leu Arg Thr His Thr Gly Glu Lys Pro Phe Gln Cys
        50                  55                  60

Arg Ile Cys Met Arg Asn Phe Ser Arg Val Asp Asn Leu Pro Arg His
65                  70                  75                  80

Leu Lys Thr His

<210> SEQ ID NO 22
<211> LENGTH: 83
<212> TYPE: PRT
<213> ORGANISM: Artificial
<220> FEATURE:
<223> OTHER INFORMATION: Try123 DNA binding sequence

<400> SEQUENCE: 22

Glu Lys Pro Tyr Lys Cys Pro Glu Cys Gly Lys Ser Phe Ser Asp Arg
1               5                   10                  15

Ser Asn Leu Thr Arg His Gln Arg Thr His Thr Gly Glu Lys Pro Tyr
                20                  25                  30

Lys Cys Pro Glu Cys Gly Lys Ser Phe Ser Thr Ser Asn Leu Ala
            35                  40                  45

Arg His Gln Arg Thr His Thr Gly Glu Lys Pro Phe Lys Cys Pro Glu
        50                  55                  60

Cys Gly Lys Ser Phe Ser Arg Ser Asp Ala Leu Thr Arg His Gln Arg
65                  70                  75                  80

Thr His Thr

<210> SEQ ID NO 23
<211> LENGTH: 10
<212> TYPE: PRT
<213> ORGANISM: Artificial

```
<220> FEATURE:
<223> OTHER INFORMATION: Polypeptide linker

<400> SEQUENCE: 23

Gly Gly Ser Gly Gly Gly Ser Gly Gly Ser
1               5                   10

<210> SEQ ID NO 24
<211> LENGTH: 83
<212> TYPE: PRT
<213> ORGANISM: Artificial
<220> FEATURE:
<223> OTHER INFORMATION: Tyr456 DNA binding sequence

<400> SEQUENCE: 24

Glu Lys Pro Tyr Lys Cys Pro Glu Cys Gly Lys Ser Phe Ser Gln Ser
1               5                   10                  15

Ser Asn Leu Ala Arg His Gln Arg Thr His Thr Gly Glu Lys Pro Tyr
            20                  25                  30

Lys Cys Pro Glu Cys Gly Lys Ser Phe Ser Arg Ser Asp His Leu Thr
        35                  40                  45

Lys His Gln Arg Thr His Thr Gly Glu Lys Pro Phe Lys Cys Pro Glu
    50                  55                  60

Cys Gly Lys Ser Phe Ser Gln Ser Ser Asn Leu Ala Arg His Gln Arg
65                  70                  75                  80

Thr His Thr

<210> SEQ ID NO 25
<211> LENGTH: 94
<212> TYPE: PRT
<213> ORGANISM: Artificial
<220> FEATURE:
<223> OTHER INFORMATION: Blues DNA binding sequence

<400> SEQUENCE: 25

Ala Ser Asp Asp Arg Pro Tyr Ala Cys Pro Val Glu Ser Cys Asp Arg
1               5                   10                  15

Arg Phe Ser Arg Arg Asp Val Leu Met Asn His Ile Arg Ile His Thr
            20                  25                  30

Gly Gln Lys Pro Phe Gln Cys Arg Ile Cys Met Arg Asn Phe Ser Arg
        35                  40                  45

Ser Asp His Leu Thr Thr His Ile Arg Thr His Thr Gly Glu Lys Pro
    50                  55                  60

Phe Ala Cys Asp Ile Cys Gly Arg Lys Phe Ala Asn Arg Asp Thr Leu
65                  70                  75                  80

Thr Arg His Ser Lys Ile His Leu Arg Gln Asn Asp Leu Glu
                85                  90

<210> SEQ ID NO 26
<211> LENGTH: 94
<212> TYPE: PRT
<213> ORGANISM: Artificial
<220> FEATURE:
<223> OTHER INFORMATION: Jazz DNA binding sequence

<400> SEQUENCE: 26

Ala Ser Asp Asp Arg Pro Tyr Ala Cys Pro Val Glu Ser Cys Asp Arg
1               5                   10                  15

Arg Phe Ser Arg Ser Asp Glu Leu Thr Arg His Ile Arg Ile His Thr
            20                  25                  30
```

```
Gly Gln Lys Pro Phe Gln Cys Arg Ile Cys Met Arg Asn Phe Ser Ser
         35                  40                  45

Arg Asp Val Leu Arg Arg His Asn Arg Thr His Thr Gly Glu Lys Pro
 50                  55                  60

Phe Ala Cys Asp Ile Cys Gly Arg Lys Phe Ala Ser Arg Asp Val Leu
 65                  70                  75                  80

Arg Arg His Asn Arg Ile His Leu Arg Gln Asn Asp Leu Glu
                 85                  90
```

<210> SEQ ID NO 27
<211> LENGTH: 127
<212> TYPE: PRT
<213> ORGANISM: Artificial
<220> FEATURE:
<223> OTHER INFORMATION: Bagly DNA binding sequence

<400> SEQUENCE: 27

```
Glu Phe Met Thr Gly Asp Arg Pro Tyr Ala Cys Pro Val Glu Ser Cys
1               5                   10                  15

Asp Arg Arg Phe Ser Arg Ser Asp Glu Leu Thr Arg His Ile Arg Ile
                 20                  25                  30

His Thr Gly Gln Lys Pro Phe Gln Cys Arg Ile Cys Met Arg Asn Phe
             35                  40                  45

Ser Ser Arg Asp Val Leu Arg Arg His Asn Arg Thr His Thr Gly Glu
 50                  55                  60

Lys Pro Phe Ala Cys Asp Ile Cys Gly Arg Lys Phe Ala Ser Arg Asp
 65                  70                  75                  80

Val Leu Arg Arg His Asn Arg Ile His Leu Arg Gln Gly Arg Ser His
                 85                  90                  95

Val Cys Ala Glu Cys Gly Lys Ala Phe Val Glu Ser Ser Lys Leu Lys
            100                 105                 110

Arg His Gln Leu Val His Thr Gly Glu Lys Pro Phe Gln Leu Glu
            115                 120                 125
```

<210> SEQ ID NO 28
<211> LENGTH: 175
<212> TYPE: PRT
<213> ORGANISM: Artificial
<220> FEATURE:
<223> OTHER INFORMATION: Gli1 DNA binding sequence

<400> SEQUENCE: 28

```
Lys Arg Glu Pro Glu Ser Val Tyr Glu Thr Asp Cys Arg Trp Asp Gly
1               5                   10                  15

Cys Ser Gln Glu Phe Asp Ser Gln Glu Gln Leu Val His His Ile Asn
                 20                  25                  30

Ser Glu His Ile His Gly Glu Arg Lys Glu Phe Val Cys His Trp Gly
             35                  40                  45

Gly Cys Ser Arg Glu Leu Arg Pro Phe Lys Ala Gln Tyr Met Leu Val
 50                  55                  60

Val His Met Arg Arg His Thr Gly Glu Lys Pro His Lys Cys Thr Phe
 65                  70                  75                  80

Glu Gly Cys Arg Lys Ser Tyr Ser Arg Leu Glu Asn Leu Lys Thr His
                 85                  90                  95

Leu Arg Ser His Thr Gly Glu Lys Pro Tyr Met Cys Glu His Glu Gly
            100                 105                 110

Cys Ser Lys Ala Phe Ser Asn Ala Ser Asp Arg Ala Lys His Gln Asn
            115                 120                 125
```

Arg Thr His Ser Asn Glu Lys Pro Tyr Val Cys Lys Leu Pro Gly Cys
            130                 135                 140

Thr Lys Arg Tyr Thr Asp Pro Ser Ser Leu Arg Lys His Val Lys Thr
145                 150                 155                 160

Val His Gly Pro Asp Ala His Val Thr Lys Arg His Arg Gly Asp
                165                 170                 175

<210> SEQ ID NO 29
<211> LENGTH: 84
<212> TYPE: PRT
<213> ORGANISM: Artificial
<220> FEATURE:
<223> OTHER INFORMATION: HIVC DNA binding sequence

<400> SEQUENCE: 29

Pro Phe Gln Cys Arg Ile Cys Met Arg Asn Phe Ser Leu Arg Thr Asp
1               5                   10                  15

Leu Asp Arg His Thr Arg Thr His Thr Gly Glu Lys Pro Phe Gln Cys
            20                  25                  30

Arg Ile Cys Met Arg Asn Phe Ser Leu Ser Gln Thr Leu Arg Arg His
        35                  40                  45

Leu Arg Thr His Thr Gly Glu Lys Pro Phe Gln Cys Arg Ile Cys Met
50                  55                  60

Arg Asn Phe Ser Leu Arg Ser Asn Leu Gly Arg His Leu Lys Thr His
65                  70                  75                  80

Thr Gly Glu Lys

<210> SEQ ID NO 30
<211> LENGTH: 100
<212> TYPE: PRT
<213> ORGANISM: Artificial
<220> FEATURE:
<223> OTHER INFORMATION: B3 DNA binding sequence

<400> SEQUENCE: 30

Ala Gln Ala Ala Leu Glu Pro Lys Glu Lys Pro Tyr Ala Cys Pro Glu
1               5                   10                  15

Cys Gly Lys Ser Phe Ser Asp Pro Gly Asn Leu Val Arg His Gln Arg
            20                  25                  30

Thr His Thr Gly Glu Lys Pro Tyr Lys Cys Pro Glu Cys Gly Lys Ser
        35                  40                  45

Phe Ser Arg Ser Asp Lys Leu Val Arg His Gln Arg Thr His Thr Gly
50                  55                  60

Glu Lys Pro Tyr Lys Cys Pro Glu Cys Gly Lys Ser Phe Ser Gln Ser
65                  70                  75                  80

Ser His Leu Val Arg His Gln Arg Thr His Thr Gly Lys Lys Thr Ser
                85                  90                  95

Gly Gln Ala Gly
            100

<210> SEQ ID NO 31
<211> LENGTH: 100
<212> TYPE: PRT
<213> ORGANISM: Artificial
<220> FEATURE:
<223> OTHER INFORMATION: N1 DNA binding sequence

<400> SEQUENCE: 31

Ala Gln Ala Ala Leu Glu Pro Lys Glu Lys Pro Tyr Ala Cys Pro Glu

```
                1               5                  10                 15
            Cys Gly Lys Ser Phe Ser Gln Ser Ser Leu Val Arg His Gln Arg
                            20                  25                  30
            Thr His Thr Gly Glu Lys Pro Tyr Lys Cys Pro Glu Cys Gly Lys Ser
                            35                  40                  45
            Phe Ser Gln Ser Ser Asn Leu Val Arg His Gln Arg Thr His Thr Gly
                50                  55                  60
            Glu Lys Pro Tyr Lys Cys Pro Glu Cys Gly Lys Ser Phe Ser Arg Ser
            65                  70                  75                  80
            Asp Lys Leu Val Arg His Gln Arg Thr His Thr Gly Lys Lys Thr Ser
                            85                  90                  95
            Gly Gln Ala Gly
                        100

<210> SEQ ID NO 32
<211> LENGTH: 94
<212> TYPE: PRT
<213> ORGANISM: Artificial
<220> FEATURE:
<223> OTHER INFORMATION: Sp-1 DNA binding sequence

<400> SEQUENCE: 32

Pro Gly Lys Lys Lys Gln His Ile Cys His Ile Gln Gly Cys Gly Lys
            1               5                   10                  15
            Val Tyr Gly Lys Thr Ser His Leu Arg Ala His Leu Arg Trp His Thr
                            20                  25                  30
            Gly Glu Arg Pro Phe Met Cys Thr Trp Ser Tyr Cys Gly Lys Arg Phe
                        35                  40                  45
            Thr Arg Ser Asp Glu Leu Gln Arg His Lys Arg Thr His Thr Gly Glu
                50                  55                  60
            Lys Lys Phe Ala Cys Pro Glu Cys Pro Lys Arg Phe Met Arg Ser Asp
            65                  70                  75                  80
            His Leu Ser Lys His Ile Lys Thr His Gln Asn Lys Lys Gly
                            85                  90

<210> SEQ ID NO 33
<211> LENGTH: 90
<212> TYPE: PRT
<213> ORGANISM: Artificial
<220> FEATURE:
<223> OTHER INFORMATION: Sp1 DNA binding sequence

<400> SEQUENCE: 33

Pro Gly Lys Lys Lys Gln His Ala Cys Pro Glu Cys Gly Lys Ser Phe
            1               5                   10                  15
            Ser Lys Ser Ser His Leu Arg Ala His Gln Arg Thr His Thr Gly Glu
                            20                  25                  30
            Arg Pro Tyr Lys Cys Pro Glu Cys Gly Lys Ser Phe Ser Arg Ser Asp
                        35                  40                  45
            Glu Leu Gln Arg His Gln Arg Thr His Thr Gly Glu Lys Pro Tyr Lys
                50                  55                  60
            Cys Pro Glu Cys Gly Lys Ser Phe Ser Arg Ser Asp His Leu Ser Lys
            65                  70                  75                  80
            His Gln Arg Thr His Gln Asn Lys Lys Gly
                        85                  90

<210> SEQ ID NO 34
<211> LENGTH: 4
```

<212> TYPE: PRT
<213> ORGANISM: Artificial
<220> FEATURE:
<223> OTHER INFORMATION: Polypeptide linker

<400> SEQUENCE: 34

Gly Ser Gly Ser
1

<210> SEQ ID NO 35
<211> LENGTH: 5
<212> TYPE: PRT
<213> ORGANISM: Artificial
<220> FEATURE:
<223> OTHER INFORMATION: Polypeptide linker

<400> SEQUENCE: 35

Gly Ser Gly Ser Gly
1               5

<210> SEQ ID NO 36
<211> LENGTH: 5
<212> TYPE: PRT
<213> ORGANISM: Artificial
<220> FEATURE:
<223> OTHER INFORMATION: Polypeptide linker

<400> SEQUENCE: 36

Thr Ser Ala Ala Ala
1               5

<210> SEQ ID NO 37
<211> LENGTH: 6
<212> TYPE: PRT
<213> ORGANISM: Artificial
<220> FEATURE:
<223> OTHER INFORMATION: Polypeptide linker

<400> SEQUENCE: 37

Ala Ala Ala Gly Gly Met
1               5

<210> SEQ ID NO 38
<211> LENGTH: 14
<212> TYPE: PRT
<213> ORGANISM: Artificial
<220> FEATURE:
<223> OTHER INFORMATION: Polypeptide linker

<400> SEQUENCE: 38

Ala Ala Ala Gly Gly Met Pro Pro Ala Ala Ala Gly Gly Met
1               5                   10

<210> SEQ ID NO 39
<211> LENGTH: 6
<212> TYPE: PRT
<213> ORGANISM: Artificial
<220> FEATURE:
<223> OTHER INFORMATION: Polypeptide linker

<400> SEQUENCE: 39

Ala Ala Ala Gly Gly Met
1               5

<210> SEQ ID NO 40
<211> LENGTH: 9
<212> TYPE: PRT

```
<213> ORGANISM: Artificial
<220> FEATURE:
<223> OTHER INFORMATION: Polypeptide linker

<400> SEQUENCE: 40

Pro Pro Ala Ala Ala Gly Gly Met Met
1               5

<210> SEQ ID NO 41
<211> LENGTH: 15
<212> TYPE: DNA
<213> ORGANISM: Artificial
<220> FEATURE:
<223> OTHER INFORMATION: Anchor DNA sequence

<400> SEQUENCE: 41
cgctcgagta gtaac                                                    15

<210> SEQ ID NO 42
<211> LENGTH: 116
<212> TYPE: DNA
<213> ORGANISM: Artificial
<220> FEATURE:
<223> OTHER INFORMATION: DNA scaffold containing Zif268 and PBSII
      binding sites

<400> SEQUENCE: 42
gttactactc gagcgatcgg aattcgaagg ggaattgctg ctgcggtgtt tggatggagc    60
gtgggcgggg tgtggaaatt gatgctgcat tgaccaccca agacgactgc agtaca       116

<210> SEQ ID NO 43
<211> LENGTH: 112
<212> TYPE: DNA
<213> ORGANISM: Artificial
<220> FEATURE:
<223> OTHER INFORMATION: Control DNA scaffold

<400> SEQUENCE: 43
gttactactc gagcggaatt catctaagtt actagagtcc ttatagttga ctcttgttcc    60
acattctact gtacacgctc agtactcgag cataccctatc tcctgcagta ca          112

<210> SEQ ID NO 44
<211> LENGTH: 33
<212> TYPE: DNA
<213> ORGANISM: Artificial
<220> FEATURE:
<223> OTHER INFORMATION: Psyn-Zif268 promoter

<400> SEQUENCE: 44
ttgacacatc gcgtgggcgt cgattatttt acc                                33

<210> SEQ ID NO 45
<211> LENGTH: 33
<212> TYPE: DNA
<213> ORGANISM: Artificial
<220> FEATURE:
<223> OTHER INFORMATION: Psyn-PBSII promoter

<400> SEQUENCE: 45
ttgacacatc gtgtggaaat cgattatttt acc                                33
```

```
<210> SEQ ID NO 46
<211> LENGTH: 33
<212> TYPE: DNA
<213> ORGANISM: Artificial
<220> FEATURE:
<223> OTHER INFORMATION: Psyn-tetO promoter

<400> SEQUENCE: 46
ttgacactct atcaatgata gagttatttt acc                                       33

<210> SEQ ID NO 47
<211> LENGTH: 105
<212> TYPE: PRT
<213> ORGANISM: Artificial
<220> FEATURE:
<223> OTHER INFORMATION: Zif268 DNA binding sequence

<400> SEQUENCE: 47
```

Met His His His His His His Pro Gly Glu Lys Pro Tyr Ala Cys Pro
1               5                   10                  15

Val Glu Ser Cys Asp Arg Arg Phe Ser Arg Ser Asp Glu Leu Thr Arg
            20                  25                  30

His Ile Arg Ile His Thr Gly Gln Lys Pro Phe Gln Cys Arg Ile Cys
        35                  40                  45

Met Arg Asn Phe Ser Arg Ser Asp His Leu Thr Thr His Ile Arg Thr
    50                  55                  60

His Thr Gly Glu Lys Pro Phe Ala Cys Asp Ile Cys Gly Arg Lys Phe
65                  70                  75                  80

Ala Arg Ser Asp Glu Arg Lys Arg His Thr Lys Ile His Thr Gly Gly
                85                  90                  95

Gly Ser Gly Gly Gly Ser Gly Gly Ser
            100                 105

```
<210> SEQ ID NO 48
<211> LENGTH: 103
<212> TYPE: PRT
<213> ORGANISM: Artificial
<220> FEATURE:
<223> OTHER INFORMATION: PBSII DNA binding sequence

<400> SEQUENCE: 48
```

Met His His His His His His Pro Gly Glu Lys Pro Tyr Ala Cys Pro
1               5                   10                  15

Glu Cys Gly Lys Ser Phe Ser Gln Arg Ala Asn Leu Arg Ala His Gln
            20                  25                  30

Arg Thr His Thr Gly Glu Lys Pro Tyr Lys Cys Pro Glu Cys Gly Lys
        35                  40                  45

Ser Phe Ser Arg Ser Asp His Leu Thr Thr His Gln Arg Thr His Thr
    50                  55                  60

Gly Glu Lys Pro Tyr Lys Cys Pro Glu Cys Gly Lys Ser Phe Ser Arg
65                  70                  75                  80

Ser Asp Val Leu Val Arg His Gln Arg Thr His Thr Gly Gly Gly Ser
                85                  90                  95

Gly Gly Gly Ser Gly Gly Ser
            100

```
<210> SEQ ID NO 49
<211> LENGTH: 98
<212> TYPE: PRT
<213> ORGANISM: Artificial
<220> FEATURE:
```

<223> OTHER INFORMATION: ZFa DNA binding sequence

<400> SEQUENCE: 49

Thr Ser Ala Ala Ala Pro Gly Glu Arg Pro Phe Gln Cys Arg Ile Cys
1               5                   10                  15

Met Arg Asn Phe Ser Asp Ser Pro Thr Leu Arg Arg His Thr Arg Thr
            20                  25                  30

His Thr Gly Glu Lys Pro Phe Gln Cys Arg Ile Cys Met Arg Asn Phe
        35                  40                  45

Ser Val Arg His Asn Leu Thr Arg His Leu Arg Thr His Thr Gly Glu
    50                  55                  60

Lys Pro Phe Gln Cys Arg Ile Cys Met Arg Asn Phe Ser Asp Arg Thr
65                  70                  75                  80

Ser Leu Ala Arg His Leu Lys Thr His Tyr Pro Tyr Asp Val Pro Asp
                85                  90                  95

Tyr Ala

<210> SEQ ID NO 50
<211> LENGTH: 98
<212> TYPE: PRT
<213> ORGANISM: Artificial
<220> FEATURE:
<223> OTHER INFORMATION: ZFb DNA binding sequence

<400> SEQUENCE: 50

Thr Ser Ala Ala Ala Pro Gly Glu Arg Pro Phe Gln Cys Arg Ile Cys
1               5                   10                  15

Met Arg Asn Phe Ser Lys Lys Asp His Leu His Arg His Thr Arg Thr
            20                  25                  30

His Thr Gly Glu Lys Pro Phe Gln Cys Arg Ile Cys Met Arg Asn Phe
        35                  40                  45

Ser Leu Ser Gln Thr Leu Lys Arg His Leu Arg Thr His Thr Gly Glu
    50                  55                  60

Lys Pro Phe Gln Cys Arg Ile Cys Met Arg Asn Phe Ser Arg Leu Asp
65                  70                  75                  80

Met Leu Ala Arg His Leu Lys Thr His Tyr Pro Tyr Asp Val Pro Asp
                85                  90                  95

Tyr Ala

<210> SEQ ID NO 51
<211> LENGTH: 98
<212> TYPE: PRT
<213> ORGANISM: Artificial
<220> FEATURE:
<223> OTHER INFORMATION: ZFc DNA binding sequence

<400> SEQUENCE: 51

Thr Ser Ala Ala Ala Pro Gly Glu Arg Pro Phe Gln Cys Arg Ile Cys
1               5                   10                  15

Met Arg Asn Phe Ser Ser Pro Ser Lys Leu Ile Arg His Thr Arg Thr
            20                  25                  30

His Thr Gly Glu Lys Pro Phe Gln Cys Arg Ile Cys Met Arg Asn Phe
        35                  40                  45

```
Ser Asp Gly Ser Asn Leu Ala Arg His Leu Arg Thr His Thr Gly Glu
    50                  55                  60
Lys Pro Phe Gln Cys Arg Ile Cys Met Arg Asn Phe Ser Arg Val Asp
65                  70                  75                  80
Asn Leu Pro Arg His Leu Lys Thr His Tyr Pro Tyr Asp Val Pro Asp
                85                  90                  95
Tyr Ala
```

CONSTRUCTS AND METHODS FOR THE ASSEMBLY OF BIOLOGICAL PATHWAYS

This application claims the benefit of U.S. Provisional Patent Application Ser. No. 61/544,047, filed Oct. 6, 2011, which is hereby incorporated by reference in its entirety.

This invention was made with government support under grant numbers N000140610565 and N000140710027 awarded by the Office of Naval Research. The government has certain rights in this invention

FIELD OF THE INVENTION

The present invention relates to methods, systems and constructs for assembling synthetic biological pathways in vitro.

BACKGROUND OF THE INVENTION

Metabolic engineering of microbial pathways provides a cost-effective and environmentally benign route for producing numerous valuable compounds, including commodity and specialty chemicals (e.g. biodegradable plastics), biofuels (e.g. ethanol and butanol) and therapeutic molecules (e.g. anticancer drugs and antimicrobial compounds). However, efforts to engineer new functional biosynthetic pathways in well-characterized micro-organisms such as *Escherichia coli* are still often hampered by issues such as imbalanced pathway flux, formation of side products and accumulation of toxic intermediates that can inhibit host cell growth. One strategy for increasing metabolite production in metabolically engineered microorganisms is the use of directed enzyme organization [for a review see Conrado et al., "Engineering the Spatial Organization of Metabolic Enzymes Mimicking Nature's Synergy," *Curr. Opin. Biotechnol.* 19:492-499 (2008)]. This concept is inspired by natural metabolic systems, for which optimal metabolic pathway performance often arises from the organization of enzymes into specific complexes and, in some cases, enzyme-to-enzyme channeling (a.k.a. metabolic channeling) (Conrado et al., "Engineering the Spatial Organization of Metabolic Enzymes: Mimicking Nature's Synergy," *Curr. Opin. Biotechnol.* 19:492-499 (2008); Srere P. A., "Complexes of Sequential Metabolic Enzymes," *Annu. Rev. Biochem.* 56:89-124 (1987); Miles et al., "The Molecular Basis of Substrate Channeling," *J. Biol. Chem.* 274:12193-12196 (1999)).

The most striking naturally occurring examples are enzymes that have evolved three-dimensional structures capable of physically channeling substrates such as tryptophan synthase and carbamoyl phosphate synthase. The crystal structures of these enzymes reveal tunnels that connect catalytic sites and protect reactive intermediates from the bulk solution (Hyde et al., "Three-Dimensional Structure of the Tryptophan Synthase $\alpha_2\beta_2$ Multienzyme Complex From *Salmonella typhimurium,*" *J. Biol. Chem.* 263:17857-17871 (1988); Thoden et al., "Structure of Carbamoyl Phosphate Synthetase: A Journey of 96 A From Substrate to Product," *Biochemistry* 36:6305-6316 (1997)). Other notable examples include electrostatic channeling of negatively charged substrates along a positively charged protein surface that leads from one active site to the next (Stroud R. M., "An Electrostatic Highway," *Nat. Struct. Biol.* 1:131-134 (1994)), direct channeling of substrates via thioester linkages between polyketide synthase enzyme modules (Tsuji et al., "Selective Protein—Protein Interactions Direct Channeling of Intermediates Between Polyketide Synthase Modules," *Biochemistry* 40:2326-2331 (2001)), compartmentalization of specific enzymes into small volumes within the cell in the form of subcellular organelles (Bobik T. A., "Polyhedral Organelles Compartmenting Bacterial Metabolic Processes," *Appl. Microbiol. Biotechnol.* 70:517-525 (2006); Straight et al., "A Singular Enzymatic Megacomplex From *Bacillus subtilis,*" *Proc. Nat'l. Acad. Sci. U.S.A.* 104:305-310 (2007)), and dynamic assembly of enzyme complexes, perhaps as a feedback mechanism, to achieve a precise concentration of metabolic product (Narayanaswamy et al., "Widespread Reorganization of Metabolic Enzymes Into Reversible Assemblies Upon Nutrient Starvation," *Proc. Nat'l. Acad. Sci. U.S.A.* 106:10147-10152 (2009); An et al., "Reversible Compartmentalization of de Novo Purine Biosynthetic Complexes in Living Cells," *Science* 320:103-106 (2008)).

Inspired by these natural systems, several groups have developed methods for artificially assembling enzyme complexes to enhance the performance of biological pathways. For example, direct enzyme fusions have been used to coordinate the expression and localization of two resveratrol biosynthetic enzymes in a manner that increased product titers in yeast and mammalian cells (Zhang et al., "Using Unnatural Protein Fusions to Engineer Resveratrol Biosynthesis in Yeast and Mammalian Cells," *J. Am. Chem. Soc.* 128:13030-13031 (2006)). However, fusing more than two enzymes may prove problematic due to misfolding and/or proteolysis of the fusion protein. In a notable departure from fusion proteins, Fierobe and co-workers constructed artificial cellulosomes where selected enzymes were incorporated in specific locations on a protein scaffold (Fierobe et al., "Design and Production of Active Cellulosome Chimeras. Selective Incorporation of Dockerin-Containing Enzymes Into Defined Functional Complexes," *J. Biol. Chem.* 276:21257-21261 (2001)). Compared to their free enzyme counterparts, the resulting enzyme complexes exhibited enhanced synergistic action on crystalline cellulose. More recently, Dueber et al., "Synthetic Protein Scaffolds Provide Modular Control Over Metabolic Flux," *Nat. Biotechnol.* 27:753-759 (2009) expressed scaffolds built from the interaction domains of metazoan signaling proteins to assemble metabolic enzymes that were tagged with their cognate peptide ligands. Significant increases in the production of mevalonate and separately glucaric acid were observed in the presence of several of these scaffolds. Along similar lines, Delebecque et al., "Organization of Intracellular Reactions With Rationally Designed RNA Assemblies," *Science* 333:470-474 (2011) created RNA aptamer-based scaffolds to control the spatial organization of two metabolic enzymes involved in biological hydrogen production. Similar to protein scaffolds, RNA-based scaffolds increased the hydrogen output as a function of scaffold architecture.

SUMMARY OF THE INVENTION

A first aspect of the present invention is directed to a synthetic deoxyribonucleic acid scaffold comprising one or more subunits, each subunit comprising two or more different protein-binding sequences coupled together.

Another aspect of the present invention is directed to a system for carrying out a biological pathway involving a series of sequential reactions between a substrate and two or more proteins. This system includes a substrate of the biological pathway; two or more chimeric biological pathway proteins, each chimeric protein comprising a biological pathway protein portion coupled to a heterologous DNA binding portion; and a synthetic deoxyribonucleic acid scaffold comprising one or more subunits, each subunit comprising two or more different protein-binding sequences coupled together, wherein the two or more different protein-binding sequences are binding partners with the DNA binding portions of the two or more chimeric biological pathway proteins. The protein binding sequences of the deoxyribonucleic acid scaffold are spatially assembled within a subunit to allow a series of sequential reactions involving the substrate and the two or more chimeric proteins when the DNA binding portions of two or more chimeric proteins are bound to their corresponding protein binding sequences of the deoxyribonucleic acid scaffold.

Another aspect of the present invention is directed to a method for assembling a synthetic biological pathway involving a series of sequential reactions between a substrate and two or more proteins of the biological pathway. This method involves providing two or more chimeric biological pathway proteins, each chimeric protein comprising a biological pathway protein portion coupled to a heterologous DNA binding portion, and providing a synthetic deoxyribonucleic acid scaffold comprising one or more subunits, each subunit comprising two or more different protein-binding sequences coupled together, wherein the two or more different protein-binding sequences are binding partners with the DNA binding portions of the two or more chimeric biological pathway proteins. The protein binding sequences of the deoxyribonucleic acid scaffold are spatially assembled within a subunit to allow a sequential reaction involving a substrate of the biological pathway and the two or more chimeric proteins when the DNA binding portions of two or more chimeric proteins are bound to their corresponding protein binding sequences of the deoxyribonucleic acid scaffold. The method further includes contacting the two or more chimeric proteins and the synthetic deoxyribonucleic acid scaffold under conditions effective for the DNA binding portions of the two or more chimeric proteins to bind to their corresponding protein-binding sequences on the synthetic deoxyribonucleic acid scaffold thereby assembling the synthetic biological pathway.

The present invention is directed to an alternative method for generating artificial complexes of metabolic pathway enzymes that uses DNA as the scaffold. The choice of DNA for guiding enzyme assembly affords many advantages. First, DNA has a highly predictable local structure. Therefore, scaffolds based on DNA have the potential for arranging enzymes into a predefined order. For example, the spatial orientation of bound proteins may be tuned by varying the number of nucleotides between the protein binding sites. Second, the in vivo stability of DNA scaffolds is largely sequence independent, which means that numerous architectures of virtually any sequence and length can be generated without decreasing the availability of the scaffold. Protein- and RNA-based scaffolds, on the other hand, are subject to issues associated with misfolding, aggregation and susceptibility to degradation (Ponchon & Dardel, "Recombinant RNA Technology: The tRNA Scaffold," Nat. Methods 4:571-576 (2007); Baneyx & Mujacic, "Recombinant Protein Folding and Misfolding in Escherichia coli," Nat. Biotechnol. 22:1399-1408 (2004); Chang et al., "De Novo Folding of GFP Fusion Proteins: High Efficiency in Eukaryotes but Not in Bacteria," J. Mol. Biol. 353:397-409 (2005); Netzer & Hartl, "Recombination of Protein Domains Facilitated by Co-Translational Folding in Eukaryotes," Nature 388:343-349 (1997), which are hereby incorporated by reference in their entirety), which may become more pronounced as the scaffold designs become larger and more complex (i.e. more difficult to fold, greatly increasing the likelihood of forming off-pathway intermediates and more potential sites for enzymatic degradation). In fact, the folding and stability of protein- and RNA-based scaffolds may change from one design to the next, even for very subtle changes to the RNA or protein sequence. Third, a large number of different DNA-binding proteins exist in nature. Some of them, such as zinc fingers (ZFs), have modular structures that can be engineered to bind unique DNA sequences with nanomolar dissociation constants and discriminate effectively against nonspecific DNA (Greisman & Pabo, "A General Strategy for Selecting High-Affinity Zinc Finger Proteins for Diverse DNA Target Sites," Science 275: 657-661 (1997); Rebar & Pabo, "Zinc Finger Phage: Affinity Selection of Fingers With New DNA-Binding Specificities," Science 263:671-673 (1994), which are hereby incorporated by reference in their entirety). As a result of these and other advanced ZF selection methods (Maeder et al., "Rapid "Open-Source" Engineering of Customized Zinc-Finger Nucleases for Highly Efficient Gene Modification," Mol. Cell. 31:294-301 (2008); Sander et al., "Selection-Free Zinc-Finger-Nuclease Engineering by Context-Dependent Assembly (CoDA)," Nat. Methods 8:67-69 (2011), which are hereby incorporated by reference in their entirety), there are already more than 700 experimentally tested ZFs available for use with DNA scaffolds. Relative to the seemingly limitless number of highly active ZF domains and corresponding DNA sequences, there are far fewer characterized protein interaction domains and RNA-binding proteins with ultra-high affinity for their targets. Finally, fourth, because of the similar overall fold, different zinc finger domains have comparable in vivo folding and stability profiles compared to the more structurally diverse protein interaction and RNA-binding domains used in earlier systems.

BRIEF DESCRIPTION OF THE DRAWINGS

FIG. 1A is a HPLC chromatogram of pcoumaric acid and trans resveratrol standards that were used to identify and quantify metabolites in culture broth extracts. Representative samples of 10-fold diluted culture broth extracts from cells transformed with plasmids encoding for resveratrol pathway fusion enzymes and either the random scaffold control or the $[1:1]_{16}$, 2 bp scaffold. FIG. 1B is a MS analysis of trans-resveratrol standard or diluted culture broth extract. Trans-resveratrol is detected at m/z=227.

FIG. 2A is a HPLC chromatogram showing representative standards including succinic acid, lactic acid, 1,2-PD and ethanol that were used to identify and quantify metabolites in culture broth extracts. Representative samples of undiluted culture supernatant from cells transformed with a plasmid encoding the 1,2-PD pathway and either the random scaffold control or $[1:2:1]_2$, 12-bp scaffold. FIG. 2B shows GC-MS chromatograms corresponding to mevalonolactone standard and mevalonate extracted from cells with plasmids encoding the mevalonate pathway and either the random scaffold control or the $[1:2:2]_2$, 12-bp scaffold. Samples were selected for the 71 m/z ion for mevalonolactone and the 133 m/z ion for the internal added standard (−)-trans caryophyllene. Mevalonate standard was acid-treated and extracted identically to experimental sample.

FIG. 3A is a schematic of the $(1:1)_n$ system developed for resveratrol biosynthesis. Depicted are a representative DNA scaffold (n=1) (FIG. 3A, left) and the plasmid pET-Res-ZF-Enz for expression of the ZF-enzyme chimeras (FIG. 3A, right). E1 and E2 are the enzymes 4CL and STS, respectively, while ZF domains a and b are Zif268 and PBSII, respectively. FIG. 3B is a schematic of different scaffold arrangements used for the three-enzyme pathways producing either 1,2-PD or mevalonate. E1, E2 and E3 are the 1,2-PD or mevalonate biosynthetic enzymes (see Examples for details) and the ZF domains a, b, and c are ZFa, ZFb and ZFc, respectively. In all cases where n>1 (FIG. 3B, bottom), the scaffolds were designed such that the first enzyme was always flanked on both sides by the second and third enzyme giving rise to a bidirectional pathway arrangement. Also shown is the plasmid pBAD-PD-ZF-Enz or pTet-Mev-ZF-Env for expressing 1,2-PD or mevalonate ZF-enzyme chimeras, respectively (FIG. 3B, top right). All enzymes and ZF domains were connected by flexible polypeptide linkers.

FIGS. 4A-4D show the design and evaluation of ZF chimeras. FIG. 4A shows a calibration western blot using varying amounts of purified MBP-ZFa fusion protein as standard (lanes 2-9) to quantify the level of this protein inside cells after a 12 h fermentation (lane 1). From this analysis, the amount of ZF-chimera present in cells was estimated at approximately 5000 per cell or 8 µM. The plasmid concentration in cells was determined to be approximately 127 per cell or 2 µM. These values were used to design/select ZF domains with appropriate affinity and to design DNA scaffolds with enough binding sites to accommodate all ZF fusion proteins. FIG. 4B is a western blot analysis comparing the soluble and insoluble protein levels of unmodified MBP with MBP fused to 1, 2, 3 or 4 fingers as indicated. Flow cytometric analysis of cellular fluorescence levels of superfolder green fluorescent protein (sfGFP) fused to increasing number of fingers as indicated (FIG. 4B; right). FIG. 4C is an EMSA of purified PBSII-nYFP and cYFP-Zif268 chimeras using 375 mM DNA with PBSII or Zif268 binding sites. MW, molecular weight ladder. Arrow indicates chimera-DNA complexes. EMSA of purified MBP-ZFa, MBP-ZFb and MBP-ZFc chimeras using varying amounts of biotinylated DNA containing the ZFa, ZFb or ZFc binding site is shown in FIG. 4D. Detection of DNA and DNA-protein complexes was with streptavidin-HRP against biotinylated DNA. Arrows indicate chimera-DNA complexes; asterisk indicates MBP-ZFa-DNA dimers.

FIG. 5A shows DNA-guided reassembly of split YFP fragments, nYFP and cYFP, using ZF domains. Fluorescence spectra of mixtures containing purified PBSII-nYFP and cYFP-Zif268 chimeras in the presence of either buffer, a random DNA scaffold or a DNA scaffold containing specific PBSII/Zif268 sites separated by 2 bp. Binding of 5 µM cYFP-Zif268 alone or a mixture of 5 µM PBSII-nYFP and cYFP-Zif268 to the DNA scaffold containing PBSII and Zif268 binding sites separated by 2 bp is shown in FIG. 5B. Inset depicts binding of 1 µM cYFP-Zif268 to a specific or random DNA scaffold as indicated. The left panel of FIG. 5C is a graph showing the inhibition of β-gal expression by cells expressing the Zif268 or PBSII ZF domains and the lacZ gene controlled by PSYN. Induction of each ZF was driven from an arabinose inducible promoter. Data was normalized to the β-gal level measured in cells with no ZF induction (0% arabinose). The right panel of FIG. 5C is a graph showing inhibition of β-gal expression by Zif268 or PBSII in the presence of 1% arabinose, when the PSYN promoter contained either the specific ZF binding site (target DNA) or an unrelated DNA binding site (control DNA; CTCTATCAATGATAGAG (SEQ ID NO: 48)). Data was normalized to β-gal levels measured in cells carrying the control DNA binding site. Data are average of three replicate experiments and error bars are the SEM.

FIG. 6A is a schematic representation of the resveratrol biosynthetic pathway. FIG. 6B shows a comparison of resveratrol titers from E. coli cells expressing the 4CL-STS fusion or Zif268-4CL and PBSII-STS chimeras in the presence of DNA scaffolds (n=16) with different spacer lengths between ZF binding sites or a random scaffold control plasmid. Cells expressing the ZF-enzyme chimeras in the presence of the random scaffold control served as the control to which all data was normalized. Also shown are data for the separated $(1:1)_4$ scaffold where the spacing between the ZF binding sites was 850 bp. Samples were taken 6-h post-induction. The amount of resveratrol produced in random scaffold control cells was 2.31±0.20 mg/l. Data are the average of three replicate experiments and error bars are the standard error of the mean (SEM). FIG. 6C is a western blot of enzyme levels in cells expressing the 4CL-STS fusion protein compared to cells co-expressing the Zif268-4CL and PBSII-STS chimeras.

FIG. 7A is a schematic representation of the 1,2-PD biosynthetic pathway. FIG. 7B shows a comparison of 1,2-PD titers from E. coli cells expressing the MgsA-ZFa, DkgA-ZFb and GldA-ZFc chimeras in the presence of a (1:1:1), scaffold with n=4 or 16 and the spacing between ZF binding sites=4 or 12 bp as indicated. Cells expressing the ZF-enzyme chimeras in the presence of no scaffold served as the control to which all data were normalized. Also shown are data from cells carrying a random scaffold control. The amount of 1,2-PD produced in unscaffolded control cells was 0.13±0.01 g/l. FIG. 7C shows a comparison of enzyme levels (western blot of FIG. 7C, top) and fold improvement (graph of FIG. 7C, bottom) of 1,2-PD in cells carrying different $(1:2:1)_n$ scaffolds compared to no scaffold and random scaffold controls. Also shown are data for the separated $(1:2:1)_2$ scaffold where the spacing between the ZF binding sites was ~1000 bp. Data are the average of three replicate experiments and error bars are the standard error of the mean (SEM).

FIG. 9A is a schematic representation of the mevalonate biosynthetic pathway. FIG. 9B shows a comparison of enzyme levels and mevalonate titers from E. coli cells expressing the AtoB-ZFa, HMGS-ZFb and HMGR-ZFc chimeras in the presence of $(1:2:2)_n$ scaffolds with n=1, 2, 4, 8 or 16 and the spacing between ZF binding sites=12 bp as indicated. Cells expressing the ZF-enzyme chimeras in the presence of the random scaffold control served as the control to which all data were normalized. The amount of mevalonate produced in the random scaffold control cells was 1.7±0.07 g/l. Data are the average of three replicate experiments and error bars are the standard error of the mean (SEM).

DETAILED DESCRIPTION

Figure 1A:
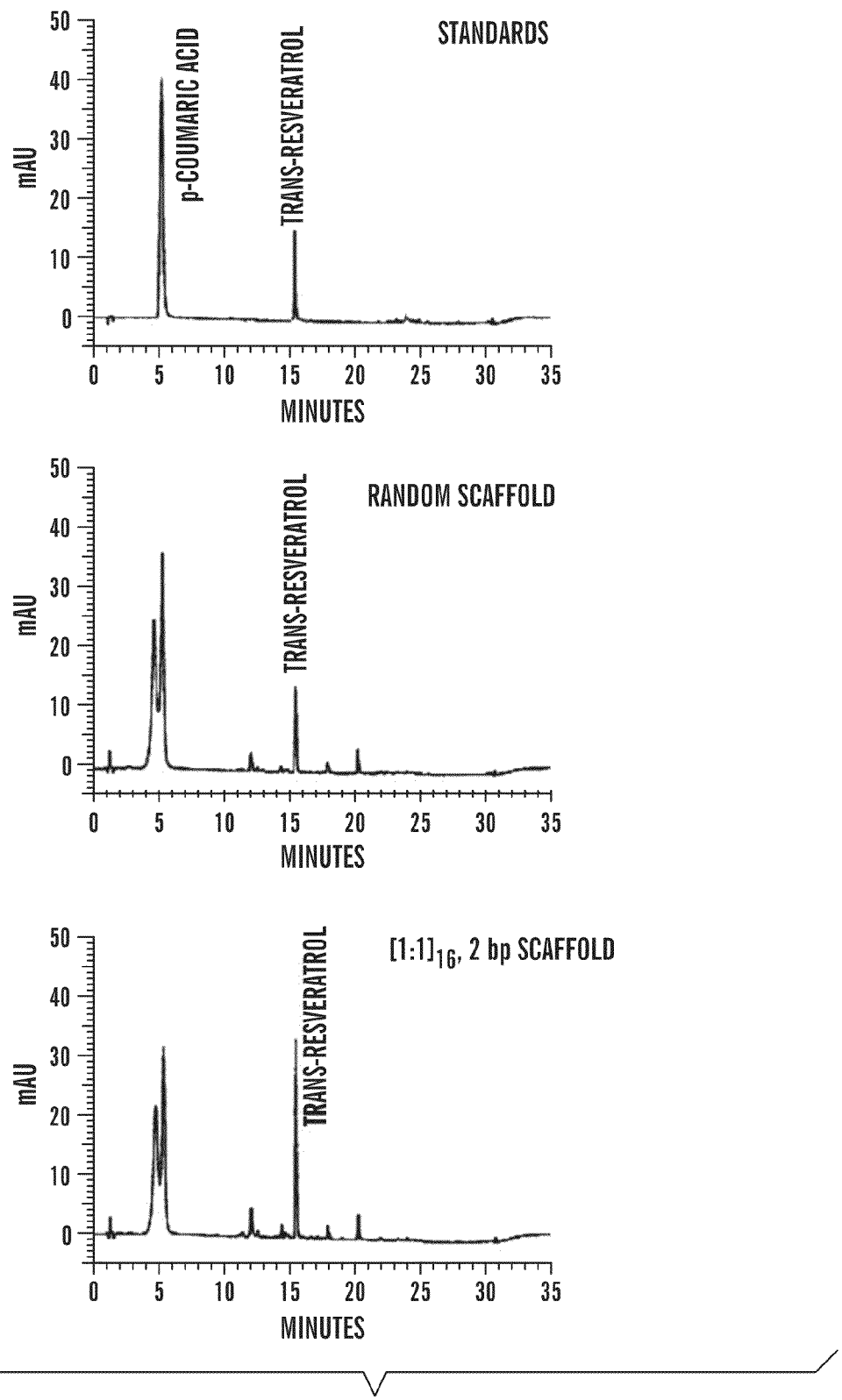
FIGS. 1A-1B show high-performance liquid chromatography (HPLC) chromatograms and mass spectroscopy (MS) analysis of resveratrol production.

A first aspect of the present invention is directed to a synthetic nucleic acid scaffold comprising one or more subunits, each subunit comprising two or more different protein-binding sequences coupled together.

As used herein, "nucleic acid", refers to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. In one embodiment of the present invention, the synthetic nucleic acid scaffold is a synthetic deoxyribonucleic acid scaffold. The deoxyribonucleotides of the synthetic scaffold may comprise purine and pyrimidine bases or other natural, chemically or biochemically modified, non-natural, or derivatized deoxyribonucleotide bases.

As used herein "synthetic" nucleic acid scaffold or "synthetic" deoxyribonucleic acid scaffold refers to a nucleic acid scaffold that is artificially produced and/or that does not exist in nature.

As described in more detail herein, the synthetic nucleic acid scaffold of the present invention is utilized to spatially and temporally assemble and immobilize two or more proteins involved in a biological pathway, i.e. biological pathway proteins, to create a functional complex. The assembly and immobilization of each biological pathway protein on the scaffold occurs via the binding interaction between one of the protein-binding sequences, i.e., protein docking sites, of the scaffold and a corresponding DNA-binding portion of a chimeric biological pathway protein. Accordingly, the synthetic nucleic acid scaffold comprises one or more subunits, each subunit comprising two or more protein-binding sequences to accommodate the binding of two or more different chimeric biological pathway proteins.

As used herein, a "protein-binding sequence" or "protein-binding site" refers to a specific nucleic acid sequence that is recognized and bound by a DNA-binding domain portion of a chimeric biological pathway protein. Many DNA-binding protein domains and their cognate binding partner recognition sites (i.e., protein binding sites) are well known in the art. For example, numerous zinc finger binding domains and their corresponding DNA protein binding target sites are known in the art and suitable for use in the present invention. Other DNA binding domains include, without limitation, leucine zipper binding domains and their corresponding DNA protein binding sites, winged helix binding domains and their corresponding DNA protein binding sites, winged helix-turn-helix binding domains and their corresponding DNA protein binding sites, HMG-box binding domains and their corresponding DNA protein binding sequences, helix-loop-helix binding domains and their corresponding DNA protein binding sequences, and helix-turn-helix binding domains and their corresponding DNA protein binding sequences. Other known DNA binding domains with known DNA protein binding sequences include the immunoglobulin DNA domain, B3 DNA binding domain, and TAL effector DNA binding domain. Nucleic acid scaffold subunits of the present invention may comprises any two or more of the aforementioned protein binding sites.

In one embodiment of the present invention, the nucleic acid scaffold subunits comprise two or more different zinc-finger protein binding sequences. A "zinc finger protein binding site" as used herein refers to a nucleotide sequence (e.g., DNA) that is recognized and bound by a particular zinc finger domain. Over 700 zinc finger domains and their corresponding target sequences are known in the art and are suitable for use in the present invention (see e.g., Greisman H A and Pabo C O, "A General Strategy for Selecting High-Affinity Zinc Finger Proteins for Diverse DNA Target Sites," *Science* 275: 657-661 (1997), Rebar E J and Pabo C O, "Zinc Finger Phage: Affinity Selection of Fingers with New DNA-Binding Specificities," Science 263:671-673 (1994); Maeder et al., "Rapid "Open-Source" Engineering of Customized Zinc-Finger Nucleases for Highly Efficient Gene Modification," *Mol. Cell.* 31:294-301 (2008), Sander et al., "Selection-Free Zinc-Finger-Nuclease Engineering by Context-Dependent Assembly (CoDA)," *Nat. Methods* 8:67-69 (2011), U.S. Pat. No. 5,5789,538 to Rebar, U.S. Pat. No. 6,410,248 to Greisman, U.S. Pat. No. 7,605,140 to Rebar, U.S. Pat. No. 6,140,081 to Barbas, U.S. Pat. No. 7,067,617 to Barbas, U.S. Pat. No. 6,205,404 to Michaels, and U.S. Patent Application Publication No. 20070178454 to Joung, which are hereby incorporated by reference in their entirety). By way of example only, Table 1 below provide a number of exemplary zinc finger DNA binding domain amino acid sequences along with the corresponding zinc finger protein binding sequences. The nucleic acid scaffold subunit of the present invention may comprise any two or more of the zinc finger protein binding sequences indentified in Table 1 or otherwise known in the art.

TABLE 1

Zinc Finger Binding DNA Binding Domain and Protein Binding Sequences

| Zinc Finger | DNA Binding Domain Sequence | Protein-Binding Sequence (5'→3') |
|---|---|---|
| Zif268 | PGEKPYACPVESCDRRFSRSDELTRHIRIHTGQ KPFQCRICMRNFSRSDHLTTHIRTHTGEKPFAC DICGRKFARSDERKRHTKIHT (SEQ ID NO: 17) | GCGTGGGCG (SEQ ID NO: 1) GCG GGG GCG (SEQ ID NO: 2) |
| PBSII | PGEKPYACPECGKSFSQRANLRAHQRTHTGE KPYKCPECGKSFSRSDHLTTHQRTHTGEKPYK CPECGKSFSRSDVLVRHQRTHT (SEQ ID NO: 18) | GTGTGGAAA (SEQ ID NO: 3) |

TABLE 1-continued

Zinc Finger Binding DNA Binding Domain and Protein Binding Sequences

| Zinc Finger | DNA Binding Domain Sequence | Protein-Binding Sequence (5'→3') |
|---|---|---|
| ZFa | PGERPFQCRICMRNFSDSPTLRRHTRTHTGEKP FQCRICMRNFSVRHNLTRHLRTHTGEKPFQCR ICMRNFSDRTSLARHLKTH (SEQ ID NO: 19) | GTCGATGCC (SEQ ID NO: 4) |
| ZFb | PGERPFQCRICMRNFSKKDHLRHTRTHTGEK PFQCRICMRNFSLSQTLKRHLRTHTGEKPFQC RICMRNFSRLDMLARHLKTH (SEQ ID NO: 20) | GCGGCTGGG (SEQ ID NO: 5) |
| ZFc | PGERPFQCRICMRNFSSPSKLIRHTRTHTGEKP FQCRICMRNFSDGSNLARHLRTHTGEKPFQCR ICMRNFSRVDNLPRHLKTH (SEQ ID NO: 21) | GAGGACGGC (SEQ ID NO: 6) |
| Tyr123 | EKPYKCPECGKSFSDRSNLTRHQRTHTGEKPY KCPECGKSFSTTSNLARHQRTHTGEKPFKCPE CGKSFSRSDALTRHQRTHT (SEQ ID NO: 22) | GTGGATGAC (SEQ ID NO: 7) |
| Tyr456 | EKPYKCPECGKSFSQSSNLARHQRTHTGEKPY KCPECGKSFSRSDHLTKHQRTHTGEKPFKCPE CGKSFSQSSNLARHQRTHT (SEQ ID NO: 24) | GAAGGGGAA (SEQ ID NO: 8) |
| Blues | ASDDRPYACPVESCDRRFSRRDVLMNHIRIHT GQKPFQCRICMRNFSRSDHLTTHIRTHTGEKPF ACDICGRKFANRDTLTRHSKIHLRQNDLE (SEQ ID NO: 25) | GTTTGGATG (SEQ ID NO: 9) |
| Jazz | ASDDRPYACPVESCDRRFSRSDELTRHIRIHTG QKPFQCRICMRNFSSRDVLRRHNRTHTGEKPF ACDICGRKFASRDVLRRHNRIHLRQNDLE (SEQ ID NO: 26) | GCTGCTGCG (SEQ ID NO: 10) |
| Bagly | EFMTGDRPYACPVESCDRRFSRSDELTRHIRIH TGQKPFQCRICMRNFSSRDVLRRHNRTHTGEK PFACDICGRKFASRDVLRRHNRIHLRQGRSHV CAECGKAFVESSKLKRHQLVHTGEKPFQLE (SEQ ID NO: 27) | CGGGCTGCTGCG (SEQ ID NO: 11) |
| Gli1 | KREPESVYETDCRWDGCSQEFDSQEQLVHHI NSEHIHGERKEFVCHWGGCSRELRPFKAQYM LVVHMRRHTGEKPHKCTFEGCRKSYSRLENL KTHLRSHTGEKPYMCEHEGCSKAFSNASDRA KHQNRTHSNEKPYVCKLPGCTKRYTDPSSLR KHVKTVHGPDAHVTKRHRGD (SEQ ID NO: 28) | GACCACCCAAGACGA (SEQ ID NO: 12) |
| HIVC | PFQCRICMRNFSLRTDLDRHTRTHTGEKPFQC RICMRNFSLSQTLRRHLRTHTGEKPFQCRICM RNFSLRSNLGRHLKTHTGEK (SEQ ID NO: 29) | GATGCTGCA (SEQ ID NO: 13) |
| B3 | AQAALEPKEKPYACPECGKSFSDPGNLVRHQ RTHTGEKPYKCPECGKSFSRSDKLVRHQRTHT GEKPYKCPECGKSFSQSSHLVRHQRTHTGKKT SGQAG (SEQ ID NO: 30) | GACGGGGG (SEQ ID NO: 14) |
| N1 | AQAALEPKEKPYACPECGKSFSQSSSLVRHQR THTGEKPYKCPECGKSFSQSSNLVRHQRTHTG EKPYKCPECGKSFSRSDKLVRHQRTHTGKKTS GQAG (SEQ ID NO: 31) | GTAGAAGGG (SEQ ID NO: 15) |
| Sp-1 | PGKKKQHICHIQGCGKVYGKTSHLRAHLR WHTGERPFMCTWSYCGKRFTR SDELQRHKRTHTGEKKFACPECPKRFMRS DHLSKHIKTHQNKKG (SEQ ID NO: 32) PGKKKQHACPECGKSFSKSSHLRAHQRTH TGERPYKCPECGKSFSRSDELQRHQRTHT GEKPYKCPECGKSFSRSDHLSKHQRTHQN KKG (SEQ ID NO: 33) | GGGGCGGGG (SEQ ID NO: 16) |

Methods for optimizing the DNA binding specificities of zinc finger domains and methods of engineering synthetic protein binding sites are also known in the art and can be utilized in the present invention to generate new zinc finger binding partners (see e.g., Bulyk et al., "Exploring the DNA-binding Specificities of Zinc Fingers with DNA Microarrays," *Proc. Nat'l Acad. Sci. U.S.A* 98(13): 7158-63 (2001) and "Hurt et al., "Highly Specific Zinc Finger Proteins Obtained by Directed Domain Shuffling and Cell-based Selection," *Proc. Nat'l Acad. Sci. U.S.A.* 100(21): 12271-6 (2003), U.S. Pat. No. 5,5789,538 to Rebar, U.S. Pat. No. 6,410,248 to Greisman, U.S. Pat. No. 7,605,140 to Rebar, U.S. Pat. No. 6,140,081 to Barbas, U.S. Pat. No. 7,067,617 to Barbas, U.S. Pat. No. 6,205,404 to Michaels, and U.S. Patent Application Publication No. 20070178454 to Joung which are hereby incorporated by reference in its entirety.

In accordance with this aspect of the present invention, the two or more different zinc finger protein-binding sites are located adjacent to each other within a scaffold subunit, coupled to each other in tandem or separated by at least one spacer nucleotide. The two or more different zinc finger protein binding sites may separated from each other by 2, 3, 4, 5, 6, 7, 8, 9, 10, 11, 12 13, 14, 15, 16, 17, 18, 19, 20, 25, 30, 35, 40, 45, 50, or more spacer nucleotides. The spacing between different zinc finger protein binding sites can vary within one scaffold unit (i.e., the spacing between a first and second protein binding site may differ from the spacing between the second and third protein binding site). Optimal spacing between different zinc finger protein-binding sites within a scaffold subunit will vary depending on the biological pathway proteins and the biological pathway, and should be optimized to achieve optimal biological pathway productivity. Methods of optimizing zinc finger protein-binding site spacing within the nucleic acid scaffold can be achieved using the methods described in the Examples herein.

Figure 3A:
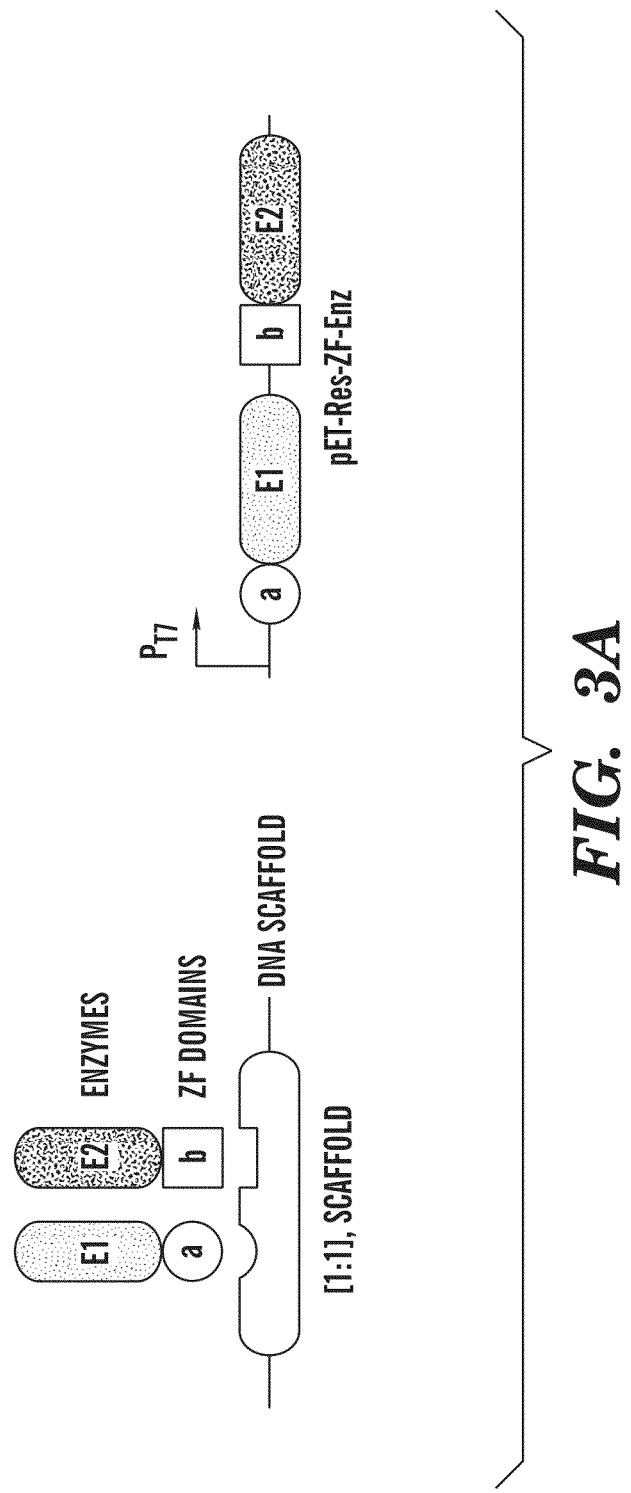
FIGS. 3A-3B are schematics showing DNA scaffold-assisted assembly of metabolic pathways in E. coli.
Figure 3B:
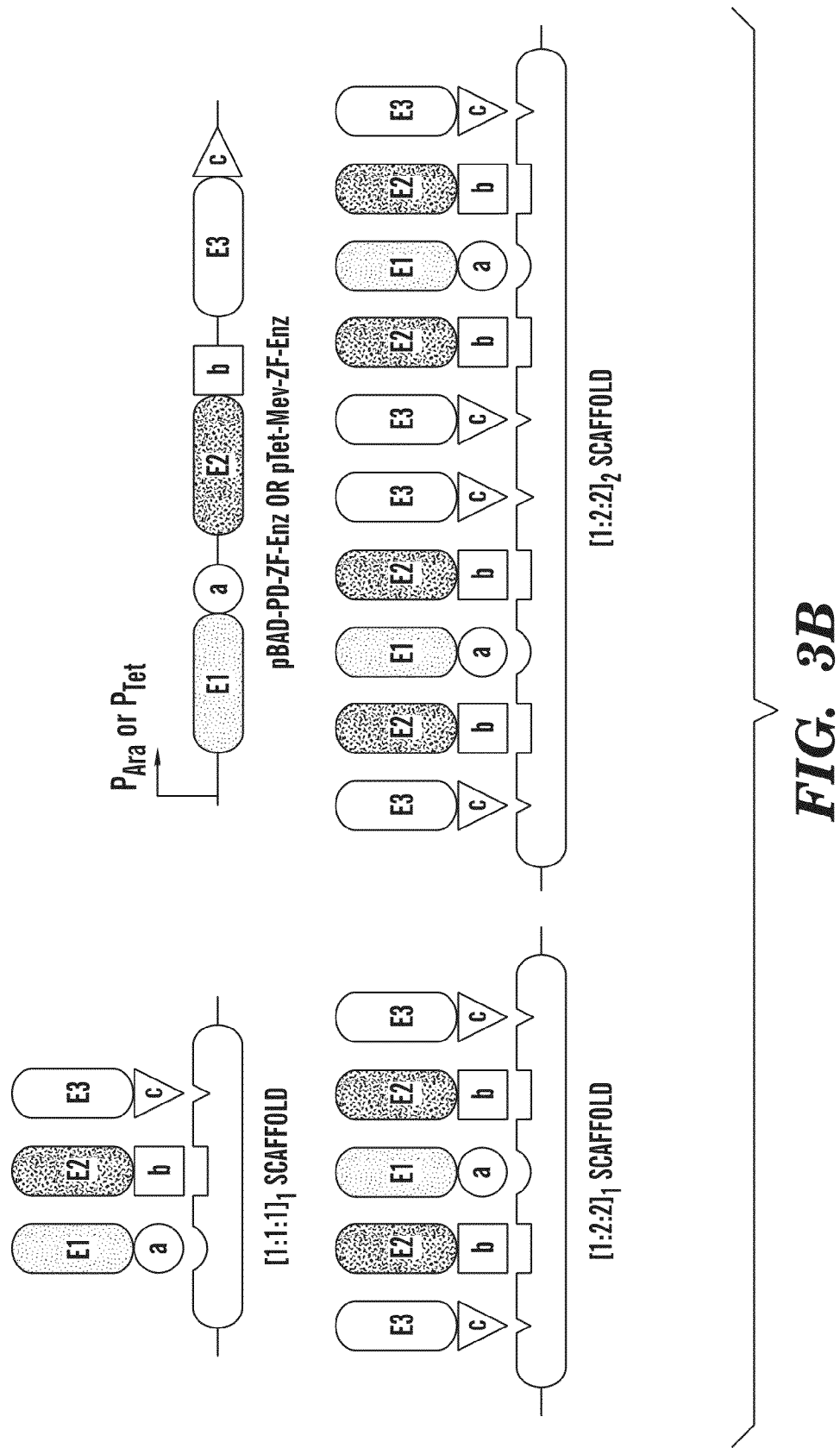

A nucleic acid scaffold subunit may comprise 2, 3, 4, 5, 6, 7, 8, 9, 10, 15, 20, 25, or more different zinc finger-protein binding sites coupled together to facilitate the binding and immobilization of 2, 3, 4, 5, 6, 7, 8, 9, 10, 15, 20, 25, or more different biological pathway proteins. Additionally, a nucleic acid scaffold subunit may comprise two or more copies of the same zinc finger protein-binding site. This architecture allows for optimizing the biological protein stiochiometry to be achieved. In accordance with this embodiment of the present invention, the same zinc finger protein binding sites may be coupled together within a subunit such that they are adjacent to each other. Alternatively, multiple copies of the same zinc finger protein binding sequence may be coupled together within a scaffold unit with one or more different zinc finger protein binding sequences separating them. Exemplary nucleic acid scaffold architectures are shown in FIGS. 3A and 3B.

The scaffold subunits are preferably repeated two or more times within the nucleic acid scaffold construct. In one embodiment of the present invention, the nucleic acid scaffold comprises one subunit repeated two or more times. In another embodiment of the present invention, the nucleic acid scaffold comprises two or more different subunits, each subunit repeated two or more times.

Another aspect of the present invention relates to a nucleic acid vector comprising the synthetic nucleic acid scaffold. Suitable nucleic acid vectors include, without limitation, plasmids, baculovirus vectors, bacteriophage vectors, phagemids, cosmids, fosmids, bacterial artificial chromosomes, viral vectors (for example, viral vectors based on vaccinia virus, poliovirus, adenovirus, adeno-associated virus, SV40, herpes simplex virus, and the like), P1-based artificial chromosomes, yeast plasmids, yeast artificial chromosomes, and other vectors. In some embodiments of the present invention, vectors suitable for use in prokaryotic host cells are preferred. Accordingly, exemplary vectors for use in prokaryotes such as *Escherichia coli* include, but are not limited to, pACYC184, pBeloBacll, pBR332, pBAD33, pBBR1MCS and its derivatives, pSC101, SuperCos (cosmid), pWE15 (cosmid), pTrc99A, pBAD24, vectors containing a ColE1 origin of replication and its derivatives, pUC, pBluescript, pGEM, and pTZ vectors.

The present invention further relates to a host cell comprising the synthetic nucleic acid scaffold of the present invention. Suitable host cells include both eukaryotic and prokaryotic cells. Eukaryotic host cells, include without limitation, animal cells, fungal cells, insect cells, plant cells, and algal cells. Suitable eukaryotic host cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorphs, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like. Suitable prokaryotic cells include, but are not limited to, any of a variety of laboratory strains of *Escherichia coli, Lactobacillus* sp., *Salmonella* sp., *Shigella* sp., *Rhodococcus* sp., *Bacillus* sp., *Pseudomonas* sp., and the like (see, e.g., Carrier et al. (1992) *J. Immunol.* 148:1176-1181; and Sizemore et al. (1995) Science 270:299-302), which are hereby incorporated by reference in their entirety).

Another aspect of the present invention is directed to a system for carrying out a biological pathway involving a series of sequential reactions between a substrate and two or more proteins. This system includes a substrate of the biological pathway; two or more chimeric biological pathway proteins, each chimeric protein comprising a biological pathway protein portion coupled to a heterologous DNA binding portion; and a synthetic deoxyribonucleic acid scaffold comprising one or more subunits, each subunit comprising two or more different protein-binding sequences coupled together, wherein the two or more different protein-binding sequences are binding partners with the DNA binding portions of the two or more chimeric biological pathway proteins. The protein binding sequences of the deoxyribonucleic acid scaffold are spatially assembled within a subunit to allow a series of sequential reactions involving the substrate and the two or more chimeric proteins when the DNA binding portions of two or more chimeric proteins are bound to their corresponding protein binding sequences of the deoxyribonucleic acid scaffold.

The chimeric biological pathway proteins of the system of the present invention comprise at least two portions. The first portion comprises a protein, or functional peptide thereof, involved in a biological pathway. The first portion of the chimeric biological pathway protein is operably coupled to a second portion comprising a DNA binding domain. As used herein, a "DNA binding domain" refers to a protein domain having at least one motif that recognizes double- or single-stranded DNA, preferably a specific DNA sequence. In a preferred embodiment of the present invention, the DNA binding domain portion differs in each chimeric biological pathway protein involved in a biological pathway.

As described supra, various DNA-binding domains of DNA binding proteins are known in the art along with their corresponding nucleotide recognition sites in DNA (i.e., protein binding sites) and are suitable for use in the system and methods of the present invention. For example, in one embodiment of the present invention, the DNA binding portion of a chimeric biological pathway protein comprises a leucine zipper DNA binding domain and a protein-binding sequence of the nucleic acid scaffold comprises the corresponding leucine zipper protein binding sequence. In another embodiment of the present invention, the DNA binding portion of a chimeric biological pathway protein comprises a helix-loop-helix DNA binding domain and a protein-binding sequence of the nucleic acid scaffold comprises the corresponding helix-loop-helix protein binding sequence. In another embodiment, the DNA binding portion of a chimeric biological pathway protein comprises a winged helix DNA binding domain and a protein-binding sequence of the nucleic acid scaffold comprises the corresponding winged helix protein-binding sequence. In another embodiment, the DNA binding portion of a chimeric biological pathway protein comprises a winged helix-turn-helix DNA binding domain and a protein-binding sequence of the nucleic acid scaffold comprises the corresponding winged helix-turn-helix protein-binding sequence. In another embodiment, the DNA binding portion of a chimeric biological pathway protein comprises a helix-turn-helix DNA binding domain and a protein-binding sequence of the nucleic acid scaffold comprises the corresponding helix-turn-helix protein-binding sequence. In another embodiment, the DNA binding portion of the chimeric biological pathway protein comprises a HMG-box DNA binding domain and a protein-binding sequence of the nucleic acid scaffold comprises the corresponding HMG-box protein-binding sequence. In another embodiment of the present invention, the DNA binding portion of a chimeric biological pathway protein comprises a zinc finger DNA binding domain and a protein-binding sequence of the nucleic acid scaffold comprises the corresponding zinc finger protein-binding sequence. Exemplary zinc finger DNA binding domain sequences and corresponding protein-binding sites are provided in Table 1 above. Other zinc finger DNA binding domains and their corresponding target sequences known in the art are also suitable for use in the present invention (see e.g., Greisman H A and Pabo C O, "A General Strategy for Selecting High-Affinity Zinc Finger Proteins for Diverse DNA Target Sites," Science 275:657-661 (1997), Rebar E J and Pabo C O, "Zinc Finger Phage: Affinity Selection of Fingers with New DNA-Binding Specificities," Science 263: 671-673 (1994); Maeder et al., "Rapid "Open-Source" Engineering of Customized Zinc-Finger Nucleases for Highly Efficient Gene Modification," Mol. Cell. 31:294-301 (2008), Sander et al., "Selection-Free Zinc-Finger-Nuclease Engineering by Context-Dependent Assembly (CoDA)," Nat. Methods 8:67-69 (2011), U.S. Pat. No. 5,5789,538 to Rebar, U.S. Pat. No. 6,410,248 to Greisman, U.S. Pat. No. 7,605,140 to Rebar, U.S. Pat. No. 6,140,081 to Barbas, U.S. Pat. No. 7,067,617 to Barbas, U.S. Pat. No. 6,205,404 to Michaels, and U.S. Patent Application Publication No. 20070178454 to Joung, which are hereby incorporated by reference in their entirety)

In accordance with this aspect of the present invention, the chimeric biological pathway proteins of the system can be formed by coupling the heterologous zinc finger DNA binding domain to the amino terminus, the carboxy terminus, or to an internal site within the biological pathway protein. When the zinc finger DNA binding domain is coupled to an internal site of the biological pathway protein, the zinc finger domain does not substantially reduce the activity of the biological pathway protein. In one embodiment of the present invention, the biological protein is coupled to its zinc finger DNA domain via a short polypeptide linker sequence. Suitable linkers include peptides of between about 6 and about 40 amino acids in length. Preferred linker sequences include glycine-rich (e.g. $G_{3-5}$), serine-rich (e.g. GSG, GSGS (SEQ ID NO: 34), GSGSG (SEQ ID NO: 35), $GS_NG$), or alanine rich (e.g., TSAAA (SEQ ID NO: 36)) linker sequences. Other exemplary linker sequences have a combination of glycine, alanine, proline and methionine residues such as AAAGGM (SEQ ID NO: 37); AAAGGMPPAAAGGM (SEQ ID NO: 38); AAAGGM (SEQ ID NO: 39); and PPAAAGGMM (SEQ ID NO: 40). Linkers may have virtually any sequence that results in a generally flexible chimeric biological pathway protein.

In one embodiment of this aspect of the present invention, the chimeric biological pathway proteins are provided in a purified isolated form. The chimeric biological proteins can be synthesized using standard methods of protein/peptide synthesis known in the art, including solid phase synthesis or solution phase synthesis. Alternatively, the chimeric biological pathway proteins can be generated using recombinant expression systems and purified using any method readily known in the art, including ion exchange chromatography, hydrophobic interaction chromatography, affinity chromatography, gel filtration, and reverse phase chromatography. In another embodiment of the present invention, the chimeric biological pathway proteins are provided in the form of a one or more nucleic acid molecules encoding the chimeric biological pathway proteins.

The preparation of nucleic acid constructs encoding chimeric biological pathway proteins can be carried using the methods described in the Examples infra or modifications thereof using standard cloning procedures well known in the art as described by Joseph Sambrook et al., MOLECULAR CLONING: A LABORATORY MANUAL (Cold Springs Harbor 1989). U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced into a suitable host cell by means of transformation and replicated by the host cell.

Nucleotide sequences encoding the chimeric biological pathway proteins may be modified such that the nucleotide sequence reflects the codon preference for the particular host cell. For example, when yeast host cells are utilized, the nucleotide sequences encoding the chimeric biological pathway proteins can be modified for yeast codon preference (see, e.g., Bennetzen and Hall (1982) J. Biol. Chem. 257(6): 3026-3031, which is hereby incorporated by reference in its entirety). Likewise, when bacterial host cells are utilized, e.g., E. coli cells, the nucleotide sequences encoding the chimeric biological pathway proteins can be modified for E. coli codon preference (see e.g., Gouy and Gautier, Nucleic Acids Res. 10(22):7055-7074 (1982); Eyre-Walker et al., Mol. Biol. Evol. 13(6):864-872 (1996) and Nakamura et al. Nucleic Acids Res. 28(1):292 (2000), which are hereby incorporated by reference in their entirety).

A variety of genetic signals and processing events that control many levels of gene expression (e.g., DNA transcription and messenger RNA ("mRNA") translation) can be incorporated into the nucleic acid construct encoding the chimeric biological pathway proteins to maximize protein production. For the purpose of expressing a cloned nucleic acid sequence encoding the desired chimeric biological pathway proteins, it is advantageous to use strong promoters to obtain a high level of transcription. Depending upon the host system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted chimeric genetic construct. Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR. Common promoters suitable for directing expression in a yeast cell include constitutive promoters such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, a PGK promoter, a GAPDH promoter, an ADC 1 promoter, a TRP 1 promoter, a URA3 promoter, a LEU2 promoter, an ENO promoter, a TP1 promoter, and a AOX1 promoter.

There are other specific initiation signals required for efficient gene transcription and translation in eukaryotic and prokaryotic cells that can be included in the nucleic acid construct to maximize chimeric protein production. Depending on the vector system and host utilized, any number of suitable transcription and/or translation elements, including constitutive, inducible, and repressible promoters, as well as minimal 5' promoter elements, enhancers, or leader sequences may be used. For a review on maximizing gene expression see Roberts and Lauer, "Maximizing Gene Expression On a Plasmid Using Recombination *In Vitro*," *Methods in Enzymology* 68:473-82 (1979), which is hereby incorporated by reference in its entirety.

A nucleic acid molecule encoding a chimeric biological pathway protein of the present invention, a promoter molecule of choice, including, without limitation, enhancers, and leader sequences; a suitable 3' regulatory region to allow transcription in the host, and any additional desired components, such as reporter or marker genes, are cloned into a vector of choice using standard cloning procedures in the art, such as described in Joseph Sambrook et al., MOLECULAR CLONING: A LABORATORY MANUAL (Cold Springs Harbor 1989); Frederick M. Ausubel, SHORT PROTOCOLS IN MOLECULAR BIOLOGY (Wiley 1999), and U.S. Pat. No. 4,237,224 to Cohen and Boyer, which are hereby incorporated by reference in their entirety. Suitable expression vectors include those described supra. Two or more nucleic acid molecules encoding two or more chimeric biological pathway proteins can be housed in the same or different expression vectors. In one embodiment of the present invention, two or more nucleic acid molecules encoding two or more chimeric biological pathway proteins are present in the same nucleic acid vector as the synthetic nucleic acid scaffold. In another embodiment of the present invention, two or more nucleic acid molecules or constructs encoding two or more chimeric biological pathway proteins are present in a different nucleic acid vector than the nucleic acid vector containing the synthetic nucleic acid scaffold.

In accordance with this embodiment of this aspect of the present invention, the system for carrying out a biological pathway further includes a host cell that houses the one or more nucleic acid vectors encoding the chimeric biological pathway proteins and the synthetic nucleic acid scaffold. Suitable eukaryotic and prokaryotic host cells are described supra. Nucleic acid vectors encoding the chimeric biological pathway proteins and containing the synthetic nucleic acid scaffolds can be stably or transiently introduced into a suitable host cell, using established techniques, including, but not limited to, electroporation, calcium phosphate precipitation, DEAE-dextran mediated transfection, liposome-mediated transfection, and the like. For stable transformation, a nucleic acid vector or construct will generally further include a selectable marker, e.g., any of several well-known selectable markers such as neomycin resistance, ampicillin resistance, tetracycline resistance, chloramphenicol resistance, kanamycin resistance, and the like. Stable transformation can also be effected (e.g., selected for) using a nutritional marker gene that confers prototrophy for an essential amino acid such as URA3, HIS3, LEU2, MET2, LYS2 and the like.

As used herein, a "biological pathway" involves a series of sequential reactions between a biological pathway substrate and two or more biological pathway proteins. There are several types of biological pathways, including, without limitation, a biosynthetic reaction pathway, metabolic reaction pathway, protein or nucleic acid degradation reaction pathway, protein folding pathway, and post translational modification pathway.

In one embodiment of this aspect of the present invention, the biological pathway is a biosynthetic reaction pathway and the two or more chimeric biological pathway proteins include enzymes of the biosynthetic reaction. The substrate of the biosynthetic reaction can be a precursor or intermediate precursor compound of the biosynthetic reaction product that is converted to a biosynthetic product via a series of sequential reactions with two or more biosynthetic reaction proteins.

In one embodiment of the present invention, the biosynthetic reaction is one that produces a natural product, such as a plant product. Exemplary natural products that can be produced via a biosynthetic reaction using the system of the present invention include, without limitation, phenylpropanoids (e.g., flavonoids and stilbenes, isoflavonoids, terpenoid quinones, coumarins, etc.), terpenoids and steroids, alkaloids, and antibiotics. The biosynthetic reactions, in particular the substrate and enzymes involved in the production of many natural products are well known in the art, see e.g., Paul M. Dewick, MEDICINAL NATURAL PRODUCTS A BIOSYNTHETIC APPROACH (John Wiley & Sons Ltd., 2002), which is hereby incorporated by reference in its entirety. Exemplary biosynthetic pathways for the production of natural products and the enzymes involved are described in more detail below.

In one embodiment of the present invention, the system is utilized to carry out the production of resveratrol, a stilbenoid in the phenylpropanoid family. As described herein, the production of trans-resveratrol is a two step process involving two chimeric biological pathway enzymes. In the first step, the substrate 4-coumaric acid is converted to 4-coumaroyl-CoA by the enzyme 4-coumarate:CoA ligase (4CL). In the second step, condensation of one molecule of 4-coumaroyl-CoA and three molecules of malonyl-CoA is carried out by the enzyme stilbene synthase (STS). Nucleotide and amino acid sequences for 4CL and STS enzymes are well known in the art, and any of these known sequence can be used to generate chimeric biological pathway enzymes for use in the methods and systems of the present invention. The 4CL and STS enzymes may be derived from the same plant, or alternatively, and as demonstrated herein, the 4CL and STS enzymes may be derived from different plants.

In addition to resveratrol production, other polypropanoid biosynthetic pathway enzymes are well known in the art and can be utilized in the system and methods of the present invention, see e.g., Mizutani et al., *Plant Physiol.* 113:755-763 (1997) and Gang et al., *Plant Physiol.* 130:1536-1544 (2002), which are hereby incorporated by reference in their entirety.

The system of the present invention can also be designed to carry out terpenoid biosynthesis using a mevalonate dependent or mevalonate independent pathway, i.e., the deoxyxylulose 5-phosphate (DXP) pathway. Enzymes involved in the mevalonate pathway include, without limitation, acetoacetyl-CoA thiolase, hydroxyl-methylglutaryl-CoA synthase (HMGS), hydroxymethylglutaryl-CoA reductase (HMGR), mevalonate kinase, phosphomevalonate kinase, mevalonate-5-pyrophosphate decarboxylase, isopentenyl-PP isomerase, prenyl transferase (farnesyl diphosphate synthase (FPPS), terpene synthase, and. Enzymes involved in the DXP pathway include, without limitation, 1-deoxy-D-xylulose-5-phosphate synthase (Dxs), 1-deoxy-D-xylulose-5-phosphate reductoisomerase (IspC), 4-diphosphocytidyl-2-C-methyl-D-erythritol synthase (IspD), 4-diphosphocytidyl-2-C-methyl-D-erythritol kinase (IspE), 2C-methyl-D-erythritol 2,4-cyclodiphosphate synthase (IspF), and 1-hydroxy-2-methyl-2-(E)-butenyl 4-diphosphate synthase (IspG). Nucleotide and amino acid sequences for the enzymes involved in the mevalonate dependent and DXP pathways are well known in the art, and any known sequence can be utilized to generate chimeric biological pathway enzymes for use in the methods and systems of the present invention. In some embodiments, the chimeric biological pathway proteins utilized in the system to achieve the terpenoid biosynthesis are derived from the same organism. In other embodiments, and as described herein, the enzymes can be derived from diverse organisms (e.g., *E. coli* and *S. cerevisiae*).

In another embodiment of the present invention, the biosynthetic reaction is one that produces a biosynthetic bio fuel product. Various bio fuel products that can be produced via biosynthetic reactions including, without limitation, isobutanol, 1-butanol, 1-proponal, 2-methyl-1-butanol, fatty acids, and hydrogen. Production of isobutanol is a multi-step process involving several enzymes including, without limitation, acetolactate synthase (AlsS), threonine dehydratase (IlvA), acetohydroxy acid isomeroreductase (IlvC), dihydroxy-acid dehydratase (IlvD), IlvIH, IlvBN, TdcB, 2-ketoacid decarboxylase (Kdc), and alcohol dehydrogenase (Adh). Enzymes involved in 1-butanol production include, without limitation, CimA, LeuABCD, KivD, Adh2, Kdc, Adh. Production of 1-proponal is a multi-step process involving several enzymes including, but not limited to, CimA, LeuABCD, KivD, Adh2, Kdc, Adh. Production of 2-methyl-1-butanol is a multi-step process involving several enzymes including, without limitation, CimA, LeuABCD, IlvIH, IlvBN, KivD, Adh2, Kdc, Adh. Enzymes involved in fatty acid synthesis include, without limitation acetyl-CoA carboxylase (AccABCD), malonyl-CoA:ACP transacylase (FabD), β-ketoacyl-ACP synthase III (FabH), β-ketoacyl-ACP synthase (Fab B), β-ketoacyl-ACP reductase (Fab G), enoyl-ACP reductase (FabI), β-hydroxyacyl-ACP dehydratase (FabZ), b-ketoacyl-ACP synthase II (FabF), glycerol-3-phosphate acyltransferase (PlsB), 1-acylglycerol-3-phosphate acyltransferase (PlsC), and acyl-ACP thioesterase (BTE) (see also Ikeda et al., *Proc. Natl. Acad. Sci. USA* 96:9509-9514 (1999) and Ward et al., *Antimicrob. Agents Chemother.* 48:4703-4712 (2004), which are hereby incorporated by reference in their entirety). Finally, hydrogen production involves the enzymes [Fefe]-hydrogenase and ferredoxin. The biosynthetic pathways and enzymes involved in the production of the aforementioned bio fuels have been well characterized. Likewise, the nucleotide and amino acid sequences for the enzymes involved in these production pathways are also well known in the art, and any known sequence can be utilized to generate chimeric biological pathway enzymes for use in the methods and systems of the present invention. As described above, chimeric biological pathway enzymes utilized in the system to achieve the biosynthesis of isobutanol, 1-butanol, 1-propanol, and the like can be derived from the same or different organisms.

In another embodiment of the present invention, the biosynthetic reaction is one that produces an organic commodity compound. For example, and as described herein, the system of the present invention can be designed to carry out the biosynthesis of 1,2-propanediol (1,2-PD), a valuable commodity compound useful in food additives, pharmaceuticals, cosmetics, and de-icers. Production of 1,2-PD is a three step process that requires at least three biological pathway enzymes, i.e., methylglyoxal synthase (MgsA), 2,5-diketo-D-gluconic acid reductase (DkgA), and glycerol dehydrogenase (GldA). Violacein is another commodity compound of pharmaceutical interest that can be produced in the system of the present invention using the vioA, vioB, vioC, vioD and vioE enzymes. Glucaric acid is compound of interest for it use as a dietary supplement, cancer chemotherapeutic and polymer production. The production of glucaric acid is a multi-step process involving several enzymes including, but not limited to Inol, MIOX, and Udh. 1,3-propanediol is another compound found in a variety of industrial products (e.g., composites, adhesives, laminates, molding), foods, cosmetics and medicines. Production of 1,3-propanediol is a multi-step process involving several enzymes including, but not limited to, DhaT, DhaB1, DhaB2, Pf1B, Pf1C, Pf1D, TutD, TutE, Adh, YqhD, glycerol dehydratase. The system and methods of the present invention can also be used for the production of 3-hydroxypropionaldehyde, a compound used in food preservation and polymer production. The production of 3-hydroxypropionaldehyde involves several enzymes including, but not limited to, DhaT, DhaB1, DhaB2, Pf1B, Pf1C, Pf1D, TutD, TutE, Adh, YqhD, glycerol dehydratase, 1,3-propanediol oxidoreductase. Nucleotide and amino acid sequences of the enzymes involved in aforementioned biosynthetic processes are well known in the art, and any known sequence can be utilized to generate chimeric biological pathway enzymes for use in the methods and systems of the present invention. The chimeric biological pathway proteins or enzymes utilized in a system to carry out biosynthesis can be derived from the same or different microorganism.

In another embodiment of the present invention the system is designed to carry out a metabolic pathway and the two or more chimeric biological pathway proteins include enzymes of a metabolic reaction pathway.

In another embodiment of the present invention, the system is designed to carry out a protein folding pathway, and the two or more chimeric biological proteins include enzymes involved in protein folding. Enzymes involved in protein folding include, without limitation, DnaK, DnaJ, GroEL, GroES, GrpE, Trigger Factor, PspA, IbpA, IbpB, Skp, SurA, Fkbp12, Hsp104, SecB, and SRP. Enzymes involved in oxidative protein folding include, without limitation, DsbA, DsbB, DsbC, DsbD, DsbG, TrxA, TrxB, GST, Gor, AhpC, Pdi, BiP. Nucleotide and amino acid sequences of the enzymes involved in protein folding processes are well known in the art, and any known sequence can be utilized to generate chimeric biological pathway enzymes for use in the methods and systems of the present invention. The chimeric biological pathway proteins or enzymes utilized in a system to carry out protein folding can be derived from the same or different microorganism.

In another embodiment of the present invention, the system is designed to carry out a protein or nucleic acid degradation pathways, and the two or more chimeric biological proteins include enzymes involved in protein or nucleic acid degradation pathways. Exemplary enzymes involved in protein and nucleic acid degradation include, without limitation, DegP, Lon, ClpB, ClpP, ClpS, ClpX, HIV-1 protease, thrombin, enterokinase, HtrA, FtsH, RNaseA, RNaseE, CasABCDE, Cas1, Cas2, Cas3. Nucleotide and amino acid sequences of the enzymes involved in protein or nucleic acid degradation processes are well known in the art, and any known sequence can be utilized to generate chimeric biological pathway enzymes for use in the methods and systems of the present invention. The chimeric biological pathway proteins or enzymes utilized in a system to carry out protein or nucleic acid degradation can be derived from the same or different microorganism.

In another embodiment of the present invention, the system is designed to carry out a post-translational modification pathway, and the two or more proteins include enzymes of the post-translational modification pathway. In one embodiment of the present invention, the post translational modification pathway is ubiquitination. Enzymes involved in ubiquitination include, without limitation E1, E2, E3 ubiquitin ligase, and ubiquitin. In another embodiment of the present invention, the post-translational modification pathway is sumoylation. Enzymes involved in sumoylation include, without limitation, SENP protease, Ulp1, SUMO E1, SUMO E2, and SUMO E3, In another embodiment of the present invention, the post-translational modification pathway is glycosylation. Enzymes involved in glycosylation include, without limitation, oligosaccharyltransferase, glycosyltransferases, and flippase. In another embodiment of the present invention, the post-translational modification pathway is phosphorylation. Enzymes involved in phosphorylation include, without limitation, phosphatase, phosphorylase, dephosphatase, dephosphorylase. Nucleotide and amino acid sequences of the enzymes involved in post-translational modification processes are well known in the art, and any known sequence can be utilized to generate chimeric biological pathway enzymes for use in the methods and systems of the present invention. The chimeric biological pathway proteins or enzymes utilized in a system to carry out post-translational modifications can be derived from the same or different microorganism.

Another aspect of the present invention is directed to a method for assembling a synthetic biological pathway involving a series of sequential reactions between a substrate and two or more proteins of the biological pathway. This method involves providing two or more chimeric biological pathway proteins, each chimeric protein comprising a biological pathway protein portion coupled to a heterologous DNA binding portion, and providing a synthetic deoxyribonucleic acid scaffold comprising one or more subunits, each subunit comprising two or more different protein-binding sequences coupled together, wherein the two or more different protein-binding sequences are binding partners with the DNA binding portions of the two or more chimeric biological pathway proteins. The protein binding sequences of the deoxyribonucleic acid scaffold are spatially assembled within a subunit to allow a sequential reaction involving a substrate of the biological pathway and the two or more chimeric proteins when the DNA binding portions of two or more chimeric proteins are bound to their corresponding protein binding sequences of the deoxyribonucleic acid scaffold. The method further includes contacting the two or more chimeric proteins and the synthetic deoxyribonucleic acid scaffold under conditions effective for the DNA binding portions of the two or more chimeric proteins to bind to their corresponding protein-binding sequences on the synthetic deoxyribonucleic acid scaffold thereby assembling the synthetic biological pathway.

In some embodiments of the present invention, the method of assembling a synthetic biological pathway involves immobilizing at least a first chimeric biological pathway protein and a second chimeric biological pathway protein onto the synthetic nucleic acid scaffold. The first chimeric biological pathway protein produces a first product that is a substrate for the second chimeric biological pathway protein. The second chimeric biological pathway protein is immobilized onto the scaffold construct such that it is positioned adjacent to or very close to the first chimeric biological pathway protein. In this way, the effective concentration of the first product is high, and the second chimeric biological pathway protein can act efficiently on the first product. As an example, a synthetic nucleic acid scaffold has immobilized thereon, in order from 3'→5' or 5'→3' of the scaffold construct a) the first chimeric biological pathway protein, and b) the second chimeric biological pathway protein to form a scaffold subunit. The scaffold subunit can be repeated two or more times within the synthetic nucleic acid scaffold.

In accordance with this and all aspects of the present invention, two or more copies (e.g., two, three, four, five, six, seven, eight, nine, ten, or more molecules) of each chimeric biological pathway protein can be immobilized onto a scaffold subunit. For example, in some embodiments, a scaffold subunit has immobilized thereon, a) one molecule (copy) of the first chimeric biological pathway protein and b) one molecule of the second chimeric biological pathway protein. In other embodiments, a scaffold subunit has immobilized thereon, a) one molecule of the first chimeric biological pathway protein and b) two or more molecules (e.g., two, three, four, five, six, or more molecules) of the second chimeric biological pathway protein. Accordingly, the ratio of any given protein in a biological pathway to any other protein in the pathway can be varied. By way of example only, the ratio of a first chimeric biological pathway protein to a second chimeric biological pathway protein can be varied from about 0.1:10 to about 10:0.1, e.g., from about 0.1:10 to about 0.5:10, from about 0.5:10 to about 1.0:10, from about 1.0:10 to about 2:10, from about 2:10 to about 5:10, from about 5:10 to about 7:10, from about 7:10 to about 10:10, from about 10:7 to about 10:5, from about 10:5 to about 10:2, from about 10:2 to about 10:1, from about 10:1 to about 10:0.5, or from about 10:0.5 to about 10:1.

In some embodiments, at least three chimeric biological pathway proteins are immobilized onto the synthetic nucleic acid scaffold to comprise a scaffold subunit. In accordance with this embodiment of the present invention, the first chimeric biological pathway protein produces a first product that is a substrate for the second chimeric biological pathway protein, and the second chimeric biological pathway protein produces a second product that is a substrate for the third chimeric biological pathway protein. In these embodiments, a scaffold subunit has immobilized thereon, in order from 3'→5' or 5'→3' of the scaffold a) the first chimeric biological pathway protein, b) the second chimeric biological pathway protein, and c) the third biological pathway protein. The scaffold unit can be repeated two or more times in the nucleic acid construct as described supra.

In another embodiment of the present invention, at least four chimeric biological pathway proteins are immobilized onto the nucleic acid scaffold. In another embodiment of the present invention, at least five chimeric biological pathway proteins are immobilized onto the nucleic acid scaffold. It will be apparent from these examples that a sixth, seventh, eighth, ninth, tenth, etc., chimeric biological pathway protein can be immobilized onto the nucleic acid scaffold, that the chimeric proteins are immobilized spatially in the order in which they function in a pathway, and that each protein can be immobilized onto the scaffold in one two, three, four, five, six, seven, eight, nine, ten, or more copies (or molecules).

In accordance with this aspect of the present invention, the synthetic biological pathway can be assembled in a cell-free (in vitro) environment. In another embodiment of the present invention, the synthetic biological pathway is assembled in a host cell (in vivo). Suitable host cells are described supra.

When the biosynthetic pathway is assembled in a host cell, the host cell is cultured in a suitable culture medium optionally supplemented with one or more additional agents, such as an inducer (e.g., where a nucleotide sequence encoding a chimeric biological pathway protein is under the control of an inducible promoter). In one embodiment of the present invention, the substrate of the biological pathway is endogenous to the host cell and upon assembly of the biological pathway in the host cell, the substrate is readily converted by the assembled pathway. In another embodiment, the substrate of the biological pathway is exogenous to the host cell. In accordance with this embodiment, the culture medium is supplemented with a substrate or substrate precursor that can be readily taken up by the host cell and converted by the assembled biological pathway. Suitable substrates include, without limitation, proteins, nucleic acid molecules, organic compounds, lipids, and glycans.

In one embodiment of the present invention, the host cell is cultured in a suitable medium and is overlaid with an organic solvent, e.g. dodecane, forming an organic layer. In accordance with this embodiment, if the biological pathway product is a secreted product, the product partitions into the organic layer following production and secretion from the host cell. Subsequently, the product can be readily purified from the organic layer.

In another embodiment of the present invention, the biological pathway product or biological pathway precursor product is separated from other products, macromolecules, etc., which may be present in the cell culture medium, the cell lysate, or the organic layer. Separation of the biological pathway product or biological pathway precursor product from other products that may be present in the cell culture medium, cell lysate, or organic layer is readily achieved using standard methods known in the art, e.g., standard chromatographic techniques. Accordingly, the biological pathway product or biological pathway precursor produced by the assembled biological pathway of the present invention can be in a purified form, e.g., at least about 40% pure, at least about 50% pure, at least about 60% pure, at least about 70% pure, at least about 80% pure, at least about 90% pure, at least about 95% pure, at least about 98%, or more than 98% pure. "Pure" in the context of a biological pathway product or biological pathway precursor refers to a product that is free from other biological pathway intermediate or precursor products, macromolecules, contaminants, etc.

A host cell comprising an assembled biological pathway of the present invention provides for enhanced production of a biological pathway product or biological pathway precursor, compared to a control host cell not containing the synthetically assembled biological pathway. Thus, production of a biological pathway product or biological pathway precursor product is increased by at least about 10%, at least about 20%, at least about 25%, at least about 30%, at least about 40%, at least about 50%, at least about 60%, at least about 70%, at least about 80%, at least about 90%, at least about 100% (or two-fold) compare to a control host cell. In other embodiments of the present invention, the biological pathway product is produced at least about 2.5-fold, at least about 3-fold, at least about 5-fold, at least about 7-fold, at least about 10-fold, at least about 15-fold, at least about 20-fold, at least about 50-fold, at least about 100-fold, or more, higher in the host cell comprising the assembled biological pathway compared to the level of the product produced in a control host cell.

A biological pathway product or a biological pathway precursor produced by the system and methods of the present invention may be produced in an amount of from about 10 mg/L to about 50 g/L, e.g., from about 10 mg/L to about 25 mg/L, from about 25 mg/L to about 50 mg/L, from about 50 mg/L to about 75 mg/L, from about 75 mg/L to about 100 mg/L, from about 100 mg/L to about 250 mg/L, from about 250 mg/L to about 500 mg/L, from about 500 mg/L to about 750 mg/L, from about 750 mg/L to about 1000 mg/L, from about 1 g/L to about 1.2 g/L, from about 1.2 g/L to about 1.5 g/L, from about 1.5 g/L to about 1.7 g/L, from about 1.7 g/L to about 2 g/L, from about 2 g/L to about 2.5 g/L, from about 2.5 g/L to about 5 g/L, from about 5 g/L to about 10 g/L, from about 10 g/L to about 20 g/L, from about 20 g/L to about 30 g/L, from about 30 g/L to about 40 g/L, or from about 40 g/L to about 50 g/L, or more.

As described supra, virtually any biological pathway can be assembled using the methods and systems of the present invention to produce a biological pathway product or product precursor. For example biosynthetic reaction pathways can be assembled for the production organic compounds, including, but are not limited to, isoprenoid compounds, isoprenoid precursor compounds, terpenoid compounds, terpenoid precursor compounds, alkaloid compounds, alkaloid precursor compounds, phenylpropanoid compounds, phenylpropanoid precursor compounds, flavonoid compounds, flavonoid precursor compounds, steroid compounds, steroid precursor compounds, polyketide compounds, polyketide precursor compounds, macrolide compounds, sugar alcohols, phenolic compounds, biofuels, pharmaceuticals, antibiotics, and the like. Other biological pathways can also be assembled using the methods and systems of the present invention, including, but not limited to metabolic pathways for the production of metabolites, protein folding pathways for the production of folded proteins, and post-translational modification pathways for the production of post-translationally modified proteins.

EXAMPLES

The following examples are provided to illustrate embodiments of the present invention but they are by no means intended to limit its scope.

Materials and Methods for Examples 1-4

Plasmid construction and protein purification. Genes for Zif268 and PBSII were codon optimized for expression in *E. coli* and synthesized by GeneArt. Chimeric PBSII-nYFP and cYFP-Zif268 proteins were assembled according to Biobrick standards into plasmid vector BBa_K245008. *E. coli* BL21 (DE3) pLysS strain was used for production of PBSII-nYFP and cYFP-Zif268 chimeras. Plasmids encoding fusion proteins under the T7 promoter were transformed in *E. coli* BL21(DE3) pLysS strain using a standard heat shock protocol, plated on LB plates with ampicillin and grown overnight at 37° C. to obtain single colonies. Single colonies were further picked for inoculation of 100 ml of LB media with ampicillin and grown at 37° C. at 160 rpm overnight. Overnight cultures were used to inoculate 1.2 L of 2xYT media (16 g/l bacto tryptone, 10 g/l bactoyeast extract, 5 g/l NaCl, pH 7) containing 100 µM $ZnCl_2$ and enriched with 10 g/l glucose to a final $OD_{600}$ of 0.15. Protein production was induced by 1 mM IPTG when bacterial cultures reached $OD_{600}$ of 0.7. After 4 h of induction, bacterial cells were pelleted and lysed in 10 mM Tris (pH 7.5), 0.1% deoxycholate, 100 µM $ZnCl_2$ and 1 mM dithiothreitol (DTT) by sonication. Most of the proteins were expressed as inclusion bodies (IB). IB were washed three times with the lysis buffer and solubilized in buffer A (10 mM Tris (pH 7.5), 100 mM NaCl, 5 mM DTT, 100 µM $ZnCl_2$) containing 6M urea. Solubilized IB were either directly dialyzed against buffer A and used in experiments or purified on Ni-NTA agarose beads (Qiagen). Solubilized IB were passed over Ni-NTA agarose beads and eluted with buffer A containing 4 M urea and increasing concentration of imidazole. Most fusion proteins eluted in the 250 mM imidazole fraction. Afterwards fusion proteins were either used in experiments directly or dialyzed against buffer A.

Maltose binding protein (MBP) was PCR amplified from *E. coli* MG1665 genomic DNA and cloned into pET28a(+) (Invitrogen). The 3'-end was appended with a codon optimized L5 linker along with the appropriate zinc finger with or without epitope tags. Growth and purification were followed as described (Moon et al., "Use of Modular, Synthetic Scaffolds for Improved Production of Glucaric Acid in Engineered *E. coli*," Metab. Eng. 12:298-305 (2010), which is hereby incorporated by reference in its entirety) with the following exceptions. Cell cultures were induced with 0.3 mM IPTG for 3 h. Cell lysates were applied over amylose resin (NEB) using Poly-Prep Chromatography Columns (Bio-Rad) with WB1 buffer substituted for column buffers. Elutions were collected in fractions of WB1 buffer supplemented with 10 mM maltose and the resulting protein concentrations were estimated by absorbance at 280 nm.

Electrophoretic mobility shift assay. For EMSA with PBSII and Zif268, 1 µg of the purified PBSII-nYFP and cYFP-Zif268 chimeras were incubated with 375 µM scaffold DNA for 3 h. Samples diluted with high-grade laboratory water to 20 µl were loaded on a 2.0% agarose gel with ethidium bromide and run at 70 V for 40 min. Nucleic acid-protein complexes were detected under UV light. Alternatively, for MBP-ZF chimeras, DNA oligos were 5' biotinylated (IDT) and annealed by slow cooling from 95° C. Binding assays were performed as described (Moon et al., "Use of Modular, Synthetic Scaffolds for Improved Production of Glucaric Acid in Engineered *E. coli*," Metab. Eng. 12:298-305 (2010), which is hereby incorporated by reference in its entirety). Samples were loaded on 5% TBE-PAGE gels (Bio-Rad) at 4° C. and then transferred to Biodyne B Nylon Membranes (Pierce). Detection of nucleic acid-protein complexes was performed using a LightShift Chemiluminescent EMSA Kit (Pierce).

Split YFP reassembly assay. Purified proteins (2.5 µM PBSII-nYFP and cYFP-Zif268) were mixed with 0.7 µM of DNA scaffold containing binding sites for PBSII and Zif268, and dialyzed into buffer A over a period of 24 h. Reconstitution experiments were conducted using D-Tube™ Dialyzer Midi, MWCO 3.5 kDa (Novagen). Successful reconstitution of YFP fluorescence was measured by Perkin Elmer LS 55 fluorometer using excitation of 480 nm and measuring emission spectra between 500 and 600 nm.

Surface plasmon resonance. Proteins that were directly dialyzed against buffer A (see above) were used in surface plasmon resonance (SPR) experiments. Proteins were further concentrated using Amicon Ultra-15 Centrifugal Filter Unit with Ultracel-10 membrane. The experiments were conducted using T100 apparatus (GE Healthcare, Biacore) and streptavidin-coated sensor chip (SA). The chip was equilibrated in an SPR buffer (20 mM HEPES, 150 mM NaCl, 2 mM DTT, 0.1 mM $ZnCl_2$ and 0.005% P20, pH 7.4) and conditioned with three pulses of 1 M NaCl in 50 mM NaOH as suggested by the producer. The biotinylated single-stranded anchor DNA (5'-CGCTCGAGTAGTAAC-3'-Biotin; SEQ ID NO: 41) was immobilized on all four flow-cells. The anchor allowed capture of the double-stranded DNA molecule with complementary overhang. A DNA scaffold (5'-GTTACTACTCGAGCGATCGGAATTC-GAAGGGGAATTGCTGCTG CGGTGTTTGGATGGA GCGTGGGCGGG GTGTGGAAATTGATGCTGCATTGACC ACCCAAGAC-GACTGCAGTACA-3'; SEQ ID NO: 42) was used that contained ZF binding sites for Zif268 and PBSII (underlined), respectively. Control DNA (5'-GTTACTACTCGAGCG-AATTCATCTAAGTTA CTAGAGTCCTTATAGT-TGACTCTTGTTCCACATTCTACTGTA-CACGCTCAGTA CTCGAGCATACCTATCTCCTGCAGTACA-3'; SEQ ID NO: 43) contained a scrambled version of the scaffold and was used to correct the responses for unspecific binding of ZF chimeras. The control DNA was immobilized in the first flow-cell, while the DNA scaffold was used in the second flow cell. Typically, immobilization of control and scaffold DNA used 0.5 µM DNA and was performed for 5 min at 5 µl/min. Protein binding was measured following injection of appropriate concentration of PBSII-nYFP and/or cYFP-Zif268 chimeras in the SPR buffer. The surface of the sensor chip was regenerated by two 30 s injections of 50 mM NaOH that removed the DNA from the anchor.

β-galactosidase inactivation assay. To test the binding activity of ZF domains in vivo, a lacZ reporter assay was designed on a single low-copy plasmid. The expression of lacZ was driven by a synthetic promoter $P_{SYN}$, which contained different ZF binding sites between the −35 and −10 promoter region (in italics): $P_{SYN}$-Zif268 (5' TTGACACATC GCGTGGGCGTCGATTATTTT ACC 3'; SEQ ID NO: 44); $P_{SYN}$-PBSII (5' TTGACACATC GTGTGGAAATCGATTATTTTACC 3; SEQ ID NO: 45); or the non-specific control $P_{SYN}$-tetO (TTGACACTCTAT-CAATGATAGAGTTATTTTACC; SEQ ID NO: 46). In addition, the plasmid also carried a gene for expression of the PBSII or Zif268 domains controlled by the arabinose-inducible $P_{BAD}$ promoter. All the elements were assembled according to Biobrick standards. β-gal activity was assessed after overnight incubation of *E. coli* DH5α cultures containing one of the above plasmids at 37° C., 180 rpm, and with or without 1% L-arabinose. Each culture (5 µl) was transferred to a 96-well clear bottom microtiter plate in triplicate. Z-buffer (100 µl) with chloroform (Z-buffer: 0.06 M $Na_2HPO_4 \times 7H_2O$, 0.04 M $NaH_2PO_4 \times H_2O$, 0.1M KCl, 0.001 M $MgSO_4 \times 7H_2O$, pH 7; Z-buffer with chloroform: Z-buffer, 1% β-mercaptoethanol, 10% chloroform) was added and bacterial cells were lysed by addition of 50 µl of Z-buffer with SDS (Z-buffer, 1.6% SDS) followed by incubation for 10 min at 28° C. 50 µl of 0.4% ONPG solution in Z-buffer was added to each well and enzyme kinetics were measured by monitoring absorbance at 405 nm over a period of 20 min in 30 sec intervals using a microplate reader. Miller units (MU) were calculated by dividing $V_{max}$ by the optical density of the corresponding bacterial cultures and multiplied by 1000.

Plasmid construction for biosynthetic pathways. Chimeric enzymes for the resveratrol biosynthetic pathway were constructed by linking the genes encoding 4CL and STS to the 3'-end of the genes encoding Zif268 and PBSII, respectively.

Each construct included a GGSGGGSGGS (SEQ ID NO: 23) polypeptide linker separating the enzyme from the ZF domain. 4CL was from *Arabidopsis thaliana* and STS was from *Vitis vinifera* and were not codon optimized for *E. coli*. Genes for Zif268 and PBSII were codon optimized for expression in *E. coli* and synthesized by GeneArt. PCR products corresponding to the coding regions for enzymes and zinc fingers were fused together by overlap extension PCR. The Zif268-4CL PCR product was restriction digested using XbaI and ApaI and PBSII-STS was digested by ApaI and BamHI. Both fragments were simultaneously ligated in XbaI/BamHI digested pET19b vector to obtain plasmid pET-Res-ZF-Enz. The 4CL-STS fusion protein in plasmid pET28a (pET-ResFusion) (Zhang et al., "Using Unnatural Protein Fusions to Engineer Resveratrol Biosynthesis in Yeast and Mammalian Cells," *J. Am. Chem. Soc.* 128:13030-13031 (2006), which is hereby incorporated by reference in its entirety) was provided by Dr. Oliver Yu (DDPSC).

The genes encoding MgsA, DkgA and GldA were PCR-amplified from *E. coli* MG1655 genomic DNA. These genes were then cloned into pBAD18 (Guzman et al., "Tight Regulation, Modulation, and High-Level Expression by Vectors Containing the Arabinose PBAD Promoter," *J. Bacteriol.* 177:4121-4130 (1995), which is hereby incorporated by reference in its entirety) as a polycistron for 1,2-PD synthesis as follows: the mgsA gene was placed between NheI and XbaI, the dkgA gene between XbaI and SphI, and the gldA gene between SphI and HindIII. The same strong ribosomal binding site was placed directly upstream of each gene in the polycistron with an NdeI site at each start codon. To the 3'-end of mgsA, dkgA and gldA, codon-optimized versions of the ZF triplets OZ052 (ZFa), OZ300 (ZFb) and OZ076 (ZFc) (Maeder et al., "Rapid "Open-Source" Engineering of Customized Zinc-Finger Nucleases for Highly Efficient Gene Modification," *Mol. Cell.* 31:294-301 (2008), which is hereby incorporated by reference in its entirety), were connected, respectively, by a codon optimized L5 polylinker (TSAAA) (Chang et al., "De Novo Folding of GFP Fusion Proteins: High Efficiency in Eukaryotes but Not in Bacteria," *J. Mol. Biol.* 353:397-409 (2005), which is hereby incorporated by reference in its entirety). Each ZF was appended with a C-terminal HA epitope tag. The resulting plasmid was named pBAD-PD-ZF-Enz.

The mevalonate pathway enzymes were tethered to ZF domains directly in the construct pRM178 (Dueber et al., "Synthetic Protein Scaffolds Provide Modular Control Over Metabolic Flux," *Nat. Biotechnol.* 27:753-759 (2009), which is hereby incorporated by reference in its entirety). Here, the linker and ligand at the 3'-end of each gene was excised and replaced exactly with the L5 linker and appropriate ZF domains as above. ZFa was fused to AtoB, ZFb fused to HMGS and ZFc fused to HMGR, with an HA epitope tag introduced on the C-terminus of all proteins. The resulting plasmid was named pTet-Mev-ZF-Enz.

Plasmid construction for DNA scaffolds. Primer pairs encoding Zif268 or PBSII binding sites (Table 2) separated by 2-, 4- or 8-bp spacers and flanked by standard Biobrick restriction sites were annealed by 10-min incubation at 95° C. and subsequent slow cooling to room temperature. Multiple copies of a DNA scaffold were assembled according to standard Biobrick assembly (Shetty et al., "Engineering BioBrick Vectors From BioBrick Parts," *J. Biol. Eng.* 2:5. (2008), which is hereby incorporated by reference in its entirety) and cloned into the high copy pSB1K3 vector.

TABLE 2

Zinc Finger Domain and Zinc Finger Binding Site Sequences

Zif268 protein sequence
target = 5'-GCGTGGGCG-3'
(SEQ ID NO: 1)
M:::::::PGEKPYACPVESCDRRFSRSDELTRHIRIHTGQKPFQCRICMR
NFSRSDHLTTHIRTHTGEKPFACDICGRKFARSDERKRHTKIHT
:::::::: (SEQ ID NO: 47)

PBSII protein sequence
target = 5'-GTGTGGAAA-3'
(SEQ ID NO: 3)
M:::::::PGEKPYACPECGKSFSQRANLRAHQRTHTGEKPYKCPECGKSF
SRSDHLTTHQRTHTGEKPYKCPECGKSFSRSDVLVRHQRTHT
:::::::: (SEQ ID NO: 48)

Zfa protein sequence
target = 5'-GTCGATGCC-3'
(SEQ ID NO: 4)
:::::PGERPFQCRICMRNFSDSPTLRRHTRTHTGEKPFQCRICMRNFSV
RHNLTRHLRTHTGEKPFQCRICMRNFSDRTSLARHLKTH:::::::
(SEQ ID NO: 49)

ZFb protein sequence
target = 5'-GCGGCTGGG-3'
(SEQ ID NO: 5)
:::::PGERPFQCRICMRNFSKKDHLRRHTRTHTGEKPFQCRICMRNFSL
SQTLKRHLRTHTGEKPFQCRICMRNFSRLDMLARHLKTH:::::::
(SEQ ID NO: 50)

ZFc protein sequence
target = 5'-GAGGACGGC-3'
(SEQ ID NO: 6)
:::::PGERPFQCRICMRNFSSPSKLIRHTRTHTGEKPFQCRICMRNFSD
GSNLARHLRTHTGEKPFQCRICMRNFSRVDNLPRHLKTH:::::::
(SEQ ID NO: 51)

For ZFa, ZFb and ZFc binding sites, pUC19 served as the basis for construction of the DNA scaffold. pUC19 was completely digested with AatII and PvuII and replaced with a polylinker containing the following restriction sites: AatII-SacI-SpeI-XbaI-SphI-ClaI-PvuII. DNA scaffolds were assembled using SpeI and XbaI cohesive ends for ligation. Basic parts were made so that scaffolds would be flanked by SpeI sites on the 5'-end and XbaI sites on the 3'-end. Composite scaffolds were constructed by digesting the backbone with XbaI and ligating an SpeI/XbaI-digested insert at the 3'-end, thus maintaining the SpeI site at the 5'-end and XbaI site at the 3'-end for future ligations. To separate the binding sites, a 4- or 12-bp spacer was employed. For 1,2-PD production, the resulting scaffolds were subcloned into pBAD18, between the β-lactamase and $P_{BAD}$ promoters, directly after the AgeI site. For mevalonate production, the scaffolds were employed directly from the pUC19 plasmid.

Bacterial strains, media and growth conditions. Resveratrol was produced in *E. coli* Rosetta (DE3) pLysS harboring pET-Res-ZF-Enz encoding the Zif268-4CL and PBSII-STS chimeras or pET-Res-Enz encoding 4CL and STS without the ZF domains in the presence of a DNA scaffold in plasmid pSB1K3. Overnight bacterial cultures were diluted to optical density measured at 600 nm ($A_{600}$) of 0.2 in 100 ml 2×YT medium in shake flasks and grown at 30° C. and 160 rpm. At $A_{600}$ of 0.8, 1 mM IPTG and 0.3 mM coumaric acid were added to induce gene expression and provide the substrate for resveratrol production, respectively. Samples were taken for analysis 6 h after induction of the ZF-enzyme chimeras. *Escherichia coli* strain W3110 harboring the pBAD-PD-ZF-Enz plasmid encoding the ZF-enzyme chimeras and corresponding DNA scaffolds was used for 1,2-PD production. 1,2-PD anaerobic fermentations were followed as described (Altaras & Cameron, "Metabolic Engineering of a 1,2-Propanediol Pathway in *Escherichia coli,*" *Appl. Environ. Microbiol.* 65:1180-1185 (1999), which is hereby incorporated by reference in its entirety) with the following exceptions. 1-Arabinose was added to 0.2% (w/v) at the time of inoculation to induce gene expression. All fermentations were run at 37° C., either at 200 or 250 rpm, with tubes held vertically or at a 45° angle. The 10-ml fermentation mixtures were inoculated to an $A_{600}$ of 0.05 with the overnight culture. Samples were taken for analysis at 9 h post-induction for Western blot analysis and 24 h post-induction for fermentation yields. Mevalonate production was conducted as described (Dueber et al., "Synthetic Protein Scaffolds Provide Modular Control Over Metabolic Flux," *Nat. Biotechnol.* 27:753-759 (2009), which is hereby incorporated by reference in its entirety) but with *E. coli* DP 10 cells harboring the pTet-Mev-ZF-Enz plasmid and a pUC19-based DNA scaffold. An inducer concentration of 250 nM anhydrotetracycline was used for all experiments. Samples were taken for analysis at 25 h post-induction for Western blot analysis and 50 h post-induction for fermentation yields. Antibiotics were provided at the following concentrations: ampicillin, 100 µg/ml; chloramphenicol, 25 µg/ml; and kanamycin, 50 µg/ml.

Figure 1B:
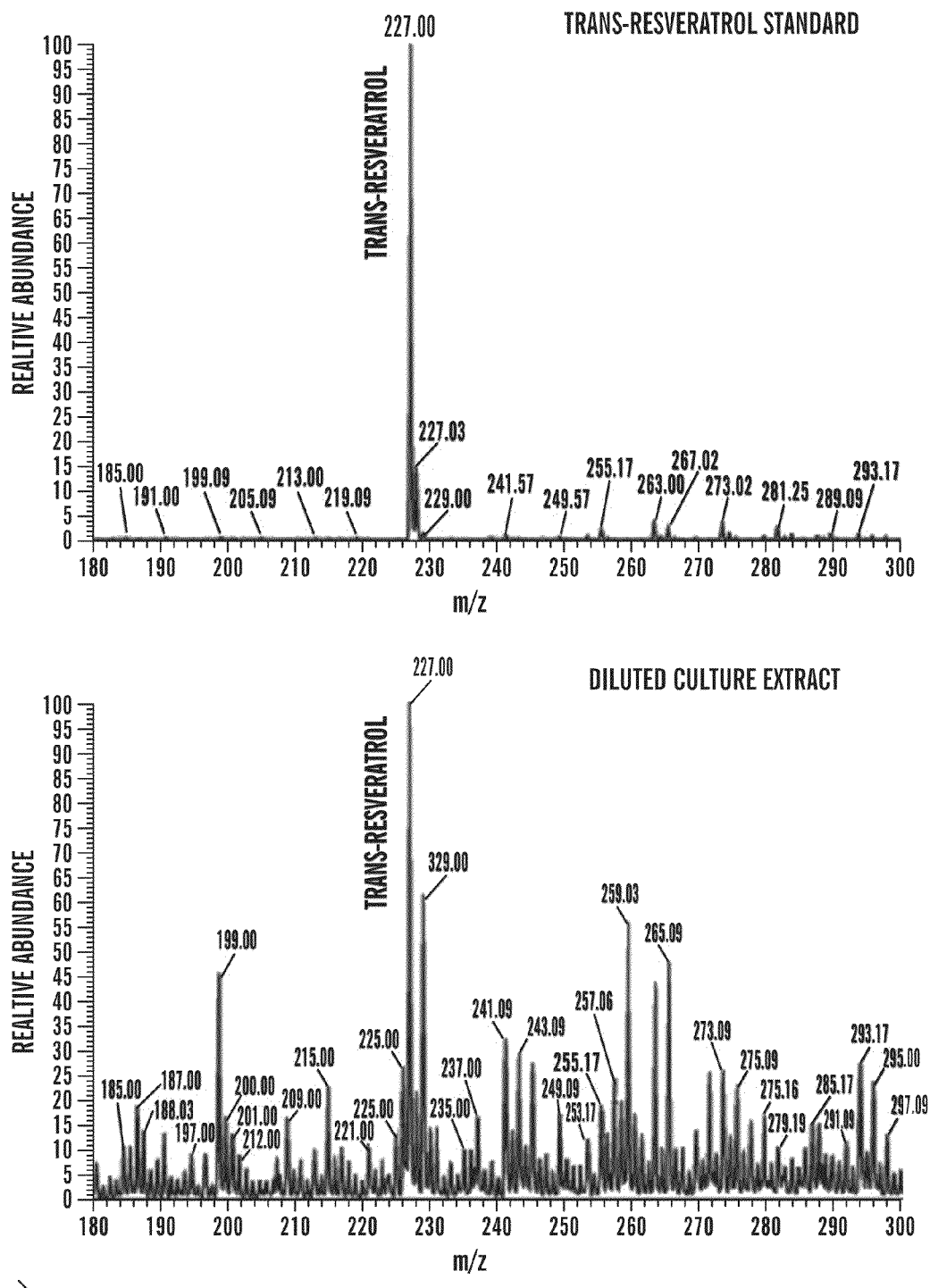
Figure 2A:
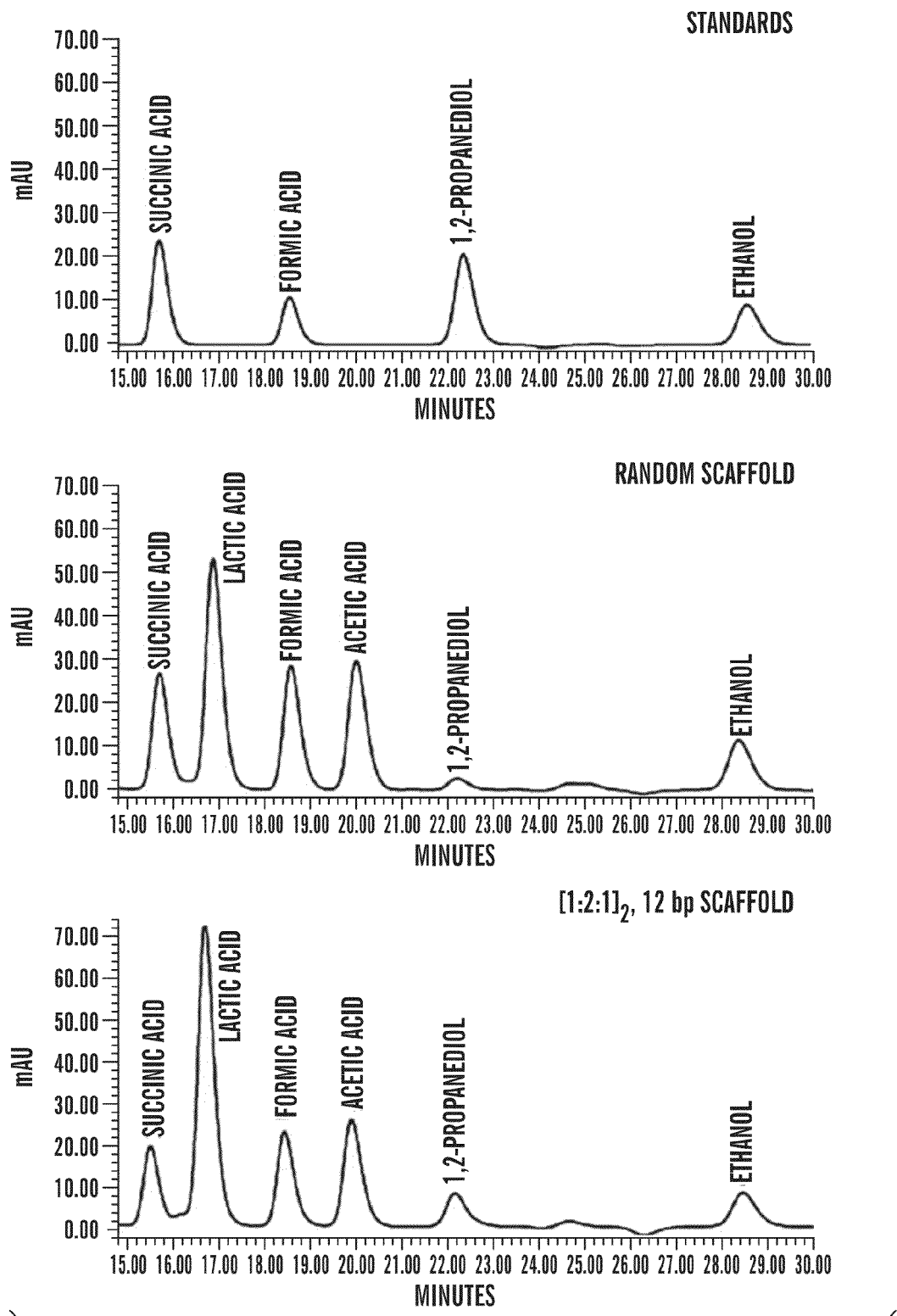
FIGS. 2A-2B are chromatograms for 1,2-PD and mevalonate production.
Figure 2B:
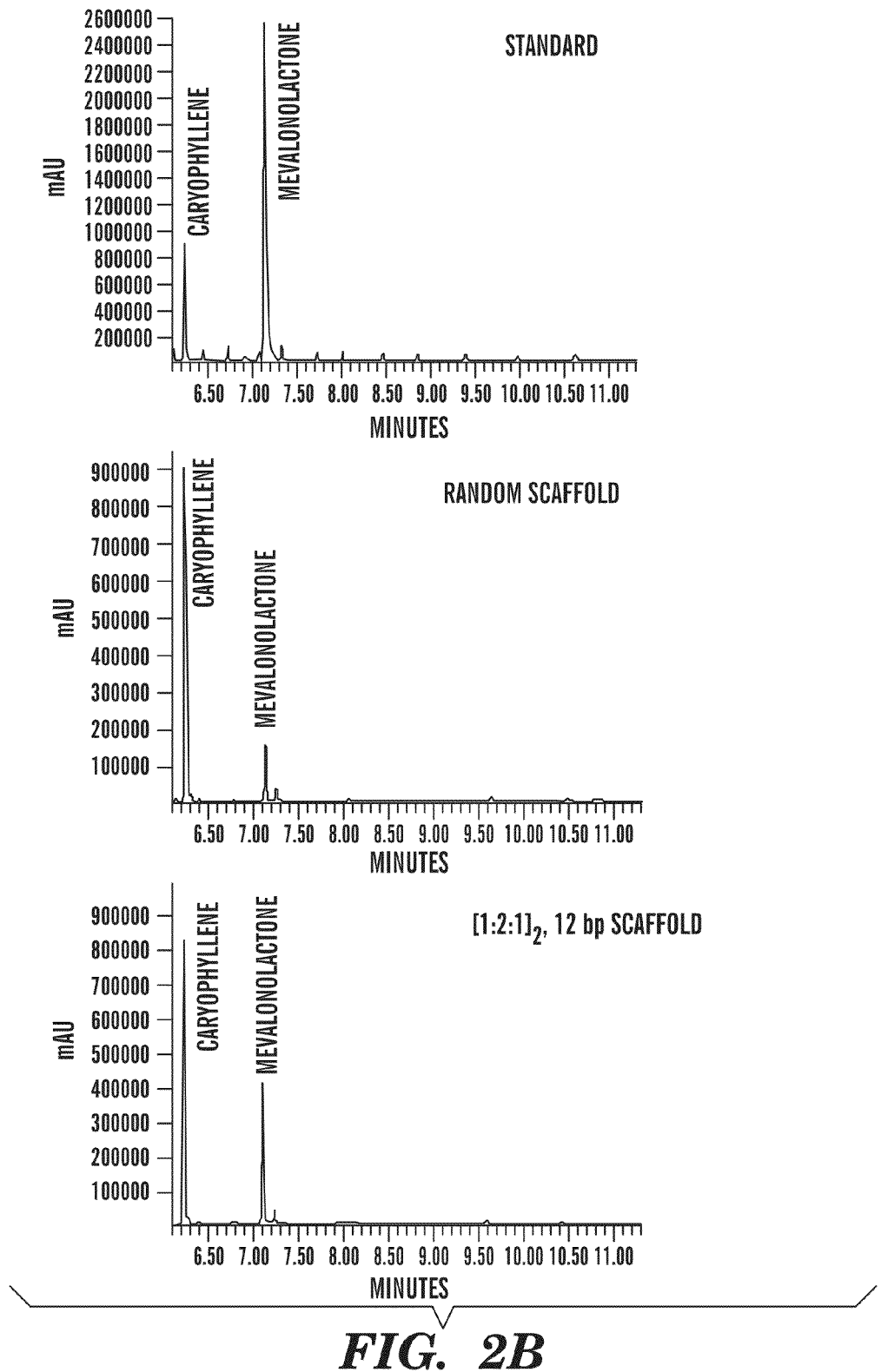

Product recovery and analysis. At selected time points, resveratrol was extracted from 1 ml of bacterial supernatants by ethyl acetate as described (Beekwilder et al., "Production of Resveratrol in Recombinant Microorganisms," *Appl. Environ. Microbiol.* 72:5670-5672 (2006), which is hereby incorporated by reference in its entirety). Briefly, supernatants were obtained after removing bacteria from culture by centrifugation at 13000 rpm. Supernatants were acidified by 1 M HCl (50 µl/1 ml supernatant) and kept at −80° C. until extracted twice by equal volumes of ethyl acetate. Ethyl acetate was removed by evaporation in vacuum evaporator and the remaining pellet resuspended in methanol prior to analysis by HPLC (Thermo Finnigan). Separation was performed at 25° C. on a stainless-steel column Hypersil ODS C18 (150×4.6 mm I.D., particle size: 5 µm, Thermo) protected by Phenomenex HPLC guard cartridge C18 as a pre-column. Adequate separation was achieved in 35 min by a gradient elution and a mobile phase consisting of acetate buffer with pH 5.6 (solvent A) and acetonitrile (solvent B). Gradient elution program applied at flow rate 1.5 ml/min was as follows: 5 min 95% A, 15 min 95-50% A, 3 min 50-5% A, 5 min 5% A, 2 min 5-95% A and 5 min 95% A. Chromatograms were monitored at 303 nm (FIG. 1A). Quantitative determination of trans-resveratrol was performed using calibration standards (0.1, 0.25, 0.5, 1 and 2 µg/ml) prepared from a stock solution of trans-resveratrol (99%, Sigma Aldrich) in 50% (v/v) methanol in water. The standard solutions were stored at −80° C. The identity of resveratrol was also confirmed by MS analysis (FIG. 1B). 1,2-PD present in the fermentation media was recovered by removal of cells and quantified as described (Altaras & Cameron, "Metabolic Engineering of a 1,2-Propanediol Pathway in *Escherichia coli,*" *Appl. Environ. Microbiol.* 65:1180-1185 (1999), which is hereby incorporated by reference in its entirety) with the following exceptions. Compounds were measured with a Waters Breeze HPLC system (FIG. 2A). The mobile phase was a 0.03 N sulfuric acid solution, with a flow rate of 0.45 ml/min, and the column and detector temperatures were 50° C. and 40° C., respectively. All samples were filtered through 0.22-µm-pore-size membranes prior to analysis. Mevalonate was recovered by acidifying cell cultures to form mevalonolactone followed by extraction with ethyl acetate exactly as described elsewhere (Dueber et al., "Synthetic Protein Scaffolds Provide Modular Control Over Metabolic Flux," *Nat. Biotechnol.* 27:753-759 (2009), which is hereby incorporated by reference in its entirety). The samples were then run on Agilent Technologies chiral cyclosil-B column (30 m length× 0.25 mm i.d.×0.25 µm Film) to determine the relative abundance of mevalonolactone as described in detail elsewhere (Dueber et al., "Synthetic Protein Scaffolds Provide Modular Control Over Metabolic Flux," *Nat. Biotechnol.* 27:753-759 (2009), which is hereby incorporated by reference in its entirety) (FIG. 2B).

Western blot analysis. *Escherichia coli* Rosetta (DE3) cells co-expressing the Zif268-4CL and PBSII-STS chimeras or expressing the 4CL-STS fusion for 6 h were harvested by centrifugation. Likewise, W3110 cultures expressing the 1,2-PD ZF-enzyme chimeras for 9 h or DP 10 cultures expressing the mevalonate ZF-enzyme chimeras for 25 h were harvested by centrifugation. Cell pellets were resuspended in PBS, lysed via sonication and centrifuged at 16 000 rpm for 10 min. The supernatant was retained as the soluble cell lysate. All samples were normalized to the amount of total soluble protein. Immunoblot analysis of soluble lysates was performed with anti-His antibodies (Sigma) to detect Zif268-4CL, PBSII-STS or 4CL-STS chimeras and anti-HA antibodies (Sigma) for detection of 1,2-PD- or mevalonate-related chimeras according to standard procedures. GroEL served as a loading control and was detected with anti-GroEL antibodies (Sigma).

Example 1

Targeting DNA In Vitro and In Vivo with ZF Domains

Figure 4A:
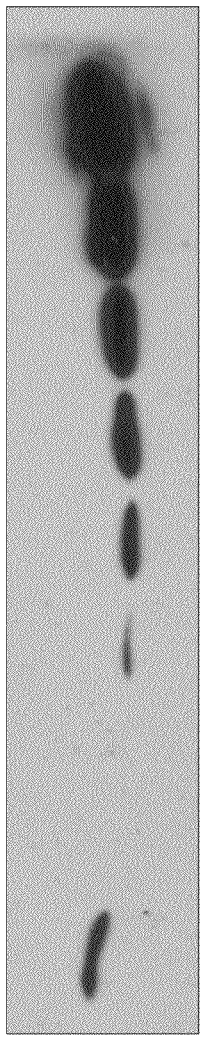
Figure 4B:
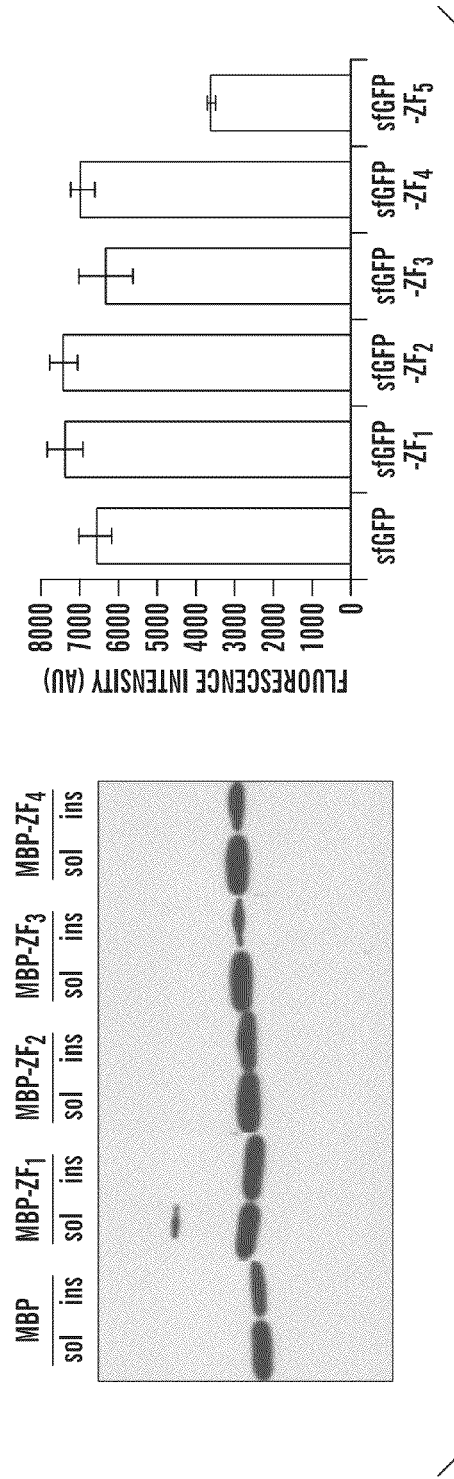

Plasmid DNA was used as a scaffold onto which cellular proteins of interest could be docked (FIG. 3). This required a method for site-specific targeting of enzymes along the DNA surface. To this end, five different ZF domains (PBSII, Zif268, ZFa, ZFb and ZFc) were used that each comprised three fingers with specificity for unique 9 base-pair DNA sequences (Maeder et al., "Rapid "Open-Source" Engineering of Customized Zinc-Finger Nucleases for Highly Efficient Gene Modification," *Mol. Cell.* 31:294-301 (2008); Hurt et al., "Highly Specific Zinc Finger Proteins Obtained by Directed Domain Shuffling and Cell-Based Selection," *Proc. Nat'l. Acad. Sci. U.S.A.* 100:12271-12276 (2003); Ooi et al., "Sequence-Enabled Reassembly of Beta-Lactamase (SEER-LAC): A Sensitive Method for the Detection of Double-Stranded DNA," *Biochemistry* 45:3620-3625 (2006); Pavletich & Pabo, "Zinc Finger-DNA Recognition: Crystal Structure of a Zif268-DNA Complex at 2.1 A," *Science* 252: 809-817 (1991); Stains et al., "DNA Sequence-Enabled Reassembly of the Green Fluorescent Protein," *J. Am. Chem. Soc.* 127:10782-10783 (2005), which are hereby incorporated by reference in their entirety) (Table 1). The selection criteria for choosing these particular ZF domains was as follows: first, the ZF domain should be non-toxic to the host cells (Sander et al., "An Affinity-Based Scoring Scheme for Predicting DNA-Binding Activities of Modularly Assembled Zinc-Finger Proteins," *Nucleic Acids Res.* 37:506-515 (2009), which is hereby incorporated by reference in its entirety); second, the ZF domains should be capable of binding orthogonal sequences with high affinity. Based on the estimation of approximately 127 plasmids per cells (0.2 µM) and approximately 5000 enzyme chimeras/cell (8 µM) (FIG. 4A), the zinc fingers should have sub-µM affinity. The five ZF domains tested here all bind DNA with low nanomolar affinity. An additional design goal was to balance fusion protein stability with the number of competitive binding sites in the *E. coli* genome. Zinc fingers comprising as many as four fingers did not impact the stability or activity of the protein to which they were fused (FIG. 4B). Of these, three-finger design were the focus, because these were relatively short (84-87 amino acids in length) and minimally cross-reactive with host DNA (only approximately 15 predicted binding sites in the E. coli genome). Importantly, none of the selected ZF domains were predicted to bind functional regions of essential genes in E. coli and thus would be unlikely to hamper bacterial fitness.

Figures 5A, 5B:
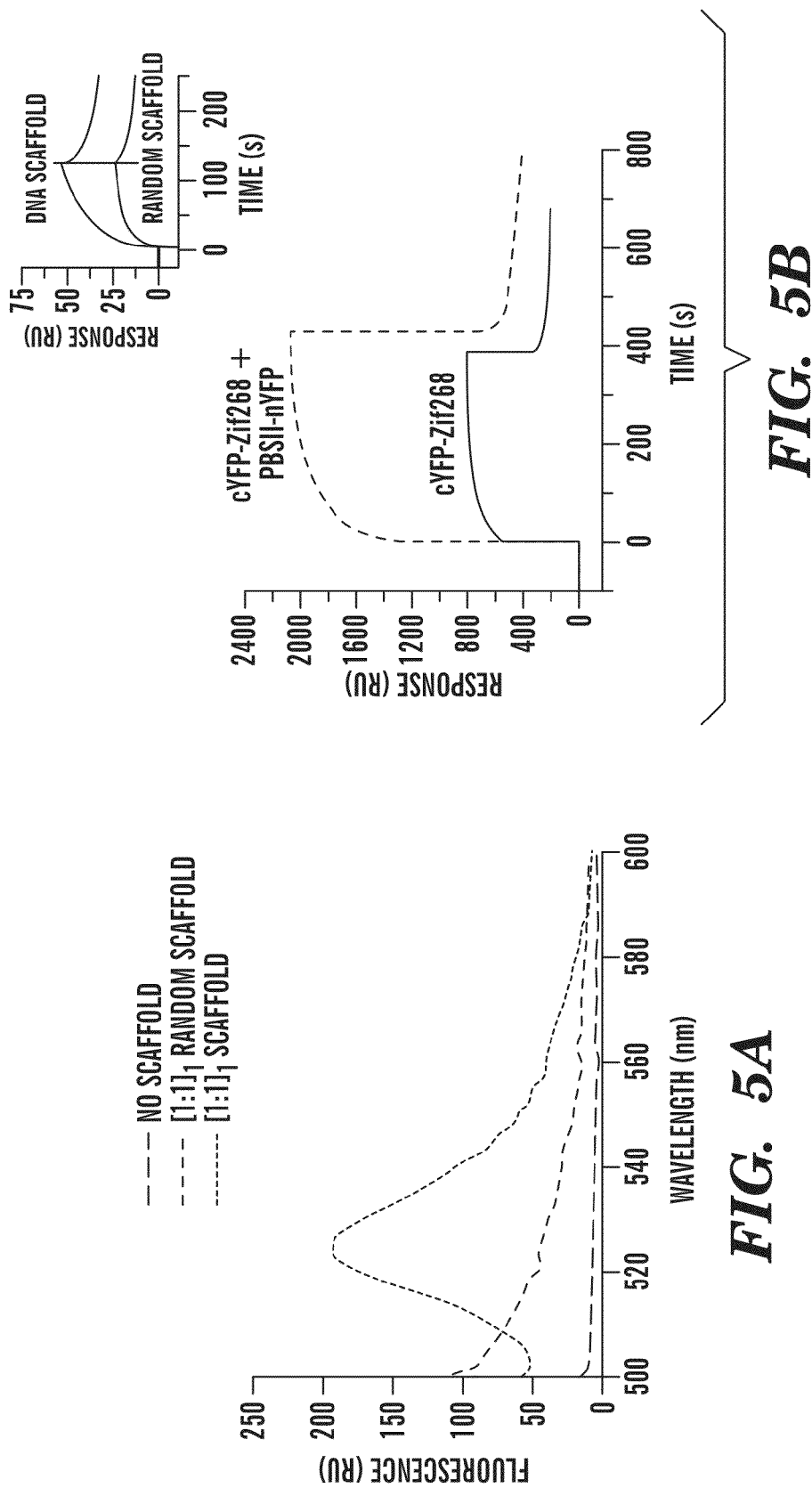
FIGS. 5A-5C demonstrate the targeting of DNA in vitro and in vivo with ZF domains.

As a first test of the system components, DNA binding of candidate ZF domains fused to the N- or C-terminus of different model proteins including fragments of the yellow fluorescent protein (YFP) and E. coli maltose-binding protein (MBP) was verified. Following purification from E. coli, all ZF chimeras bound their target DNA sequences when positioned either N- or C-terminally (FIGS. 4C and 4D). Next, whether ZF domains could bind to neighboring sites on a DNA scaffold was determined. For this, split YFP was genetically fused to the N- and C-termini of the ZF domains PBSII and Zif268, respectively. As expected, reassembly of split YFP did not occur in solution in the absence of a DNA scaffold, or in the presence of a DNA scaffold where the binding sites for the neighboring pairs were scrambled. However, strong fluorescence observed was indicative of YFP reassembly in the presence of a DNA scaffold that contained neighboring binding sites for PBSII and Zif268 separated by only two DNA base pairs (bp) (FIG. 5A). Binding of these PBSII and Zif268 chimeras to the same DNA scaffold was independently confirmed using surface plasmon resonance (SPR) (FIG. 5B). Taken together, these results indicate that (i) the expression and/or activity of different target proteins was not significantly affected when fused with these relatively small ZF domains, (ii) ZF domains retained DNA binding activity when fused to different proteins and (iii) two orthogonal ZF domains can simultaneously bind their target sequences in a DNA scaffold and bring their fused protein domains into close proximity as evidenced by the YFP reassembly.

Figure 5C:
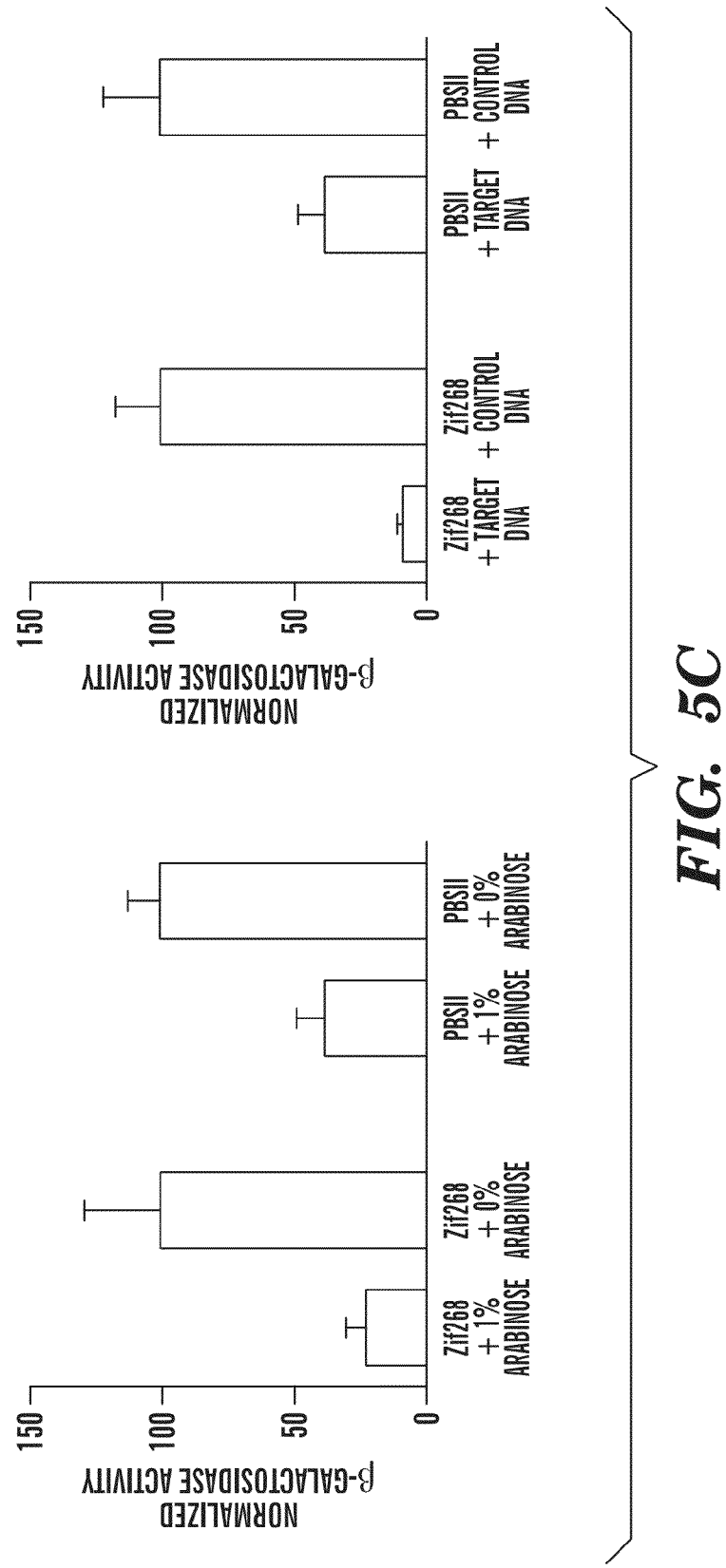

As a final test, whether these ZF domains could bind their cognate DNA targets in vivo was tested. To confirm target DNA binding by ZFs in vivo, a simple β-galactosidase (β-gal) screen for ZF activity in E. coli was generated. The assay involved a single, low-copy plasmid encoding a synthetic promoter, $P_{SYN}$, into which a DNA-binding sequence specific for each ZF domain was inserted (between 35 and 10 sites of the promoter). This promoter was positioned upstream of the lacZ reporter gene, expression of which was controlled by $P_{SYN}$. The gene encoding the ZF domain was cloned in the same plasmid but under control of the arabinose inducible $P_{BAD}$ promoter. The principle of this screen is that an active ZF domain should bind to its specific target sequence in the $P_{SYN}$ promoter and act as a synthetic repressor, thereby decreasing the basal activity of this promoter and lowering β-gal levels. As expected, induction of each ZF domain resulted in a strong reduction of β-gal activity, whereas β-gal activity was unchanged in controls where the $P_{SYN}$ promoter contained a binding site of an unrelated zinc finger (FIG. 5C). These results confirm that the ZF domains used in our studies bind specifically to their corresponding DNA target sites in vivo and thus are ideally suited for directing diverse cellular enzymes to specific sites on plasmid DNA.

Example 2

Enhancing Trans-Resveratrol Biosynthesis in the Presence of DNA Scaffolds

Figure 6A:
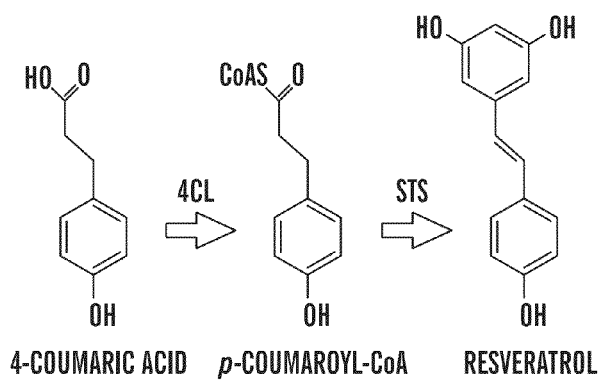
FIGS. 6A-6C show enhancement of trans-resveratrol biosynthesis in the presence of DNA scaffolds.

The ability of the ZF domains to assemble the resveratrol (trans-3,5,4'-trihydroxystilbene) biosynthetic enzymes on DNA in the cytoplasm of E. coli was also investigated. The metabolic pathway for this natural plant product has been reconstituted in microbes (Zhang et al., "Using Unnatural Protein Fusions to Engineer Resveratrol Biosynthesis in Yeast and Mammalian Cells," J. Am. Chem. Soc. 128:13030-13031 (2006); Beekwilder et al., "Production of Resveratrol in Recombinant Microorganisms," Appl. Environ. Microbiol. 72:5670-5672 (2006); Watts et al., "Biosynthesis of Plant-Specific Stilbene Polyketides in Metabolically Engineered Escherichia coli," BMC Biotechnol. 6:22 (2006), which are hereby incorporated by reference in their entirety). Production of trans-resveratrol from 4-coumaric acid occurs in two steps in which 4-coumaric acid is converted to 4-coumaroyl-CoA by 4-coumarate:CoA ligase (4CL) and trans-resveratrol is formed by condensation of one molecule of 4-coumaroyl-CoA and three molecules of malonyl-CoA by stilbene synthase (STS) (FIG. 2A). Successful DNA-guided assembly of this simple metabolic pathway would lead to measurable increases in resveratrol titers compared to the unassembled pathway. To test this notion, genes encoding 4CL and STS were fused to the Zif268 and PBSII ZF domains, respectively, in one plasmid while the DNA scaffold was present on a second plasmid. It should be noted that a large number of possible enzyme arrangements on plasmid DNA are possible. The different architectures tested here are described as $[E1_a:E2_b]_n$ for a two-enzyme system, where a and b describe the enzyme stoichiometry within a single scaffold unit [hereafter denoted as (a:b)] and n is the number of times the scaffold unit is repeated in the plasmid (FIG. 3A). For resveratrol assembly, the initial focus was on a simple (1:1) scaffold unit that was repeated 16 times on the plasmid (n=16). The rationale for this number of repeats was based on the fact that plasmid DNA copy numbers in E. coli are commonly far below that of overexpressed metabolic enzymes. Thus, it was predicted that most simple scaffold units would need to be repeated tens of times on a plasmid to accommodate all of the expressed enzymes. When the plasmids for a $(1:1)_{16}$ resveratrol system were combined in E. coli, resveratrol production was consistently enhanced by 2- to 3-fold compared to the case where a random scaffold control plasmid was present (FIG. 6).

Figure 6B:
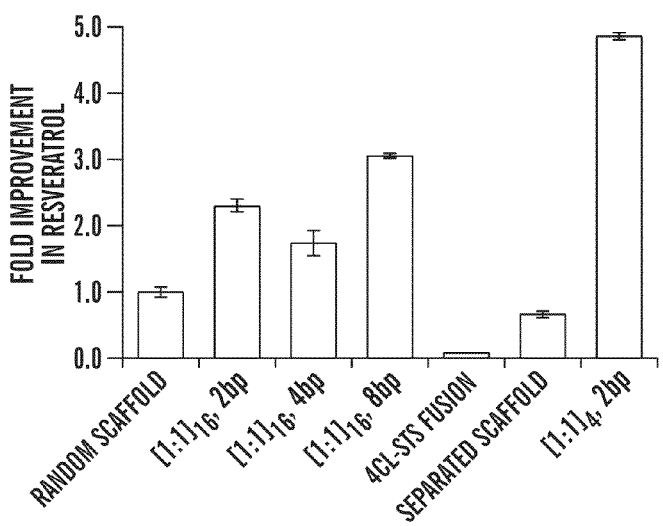

In addition to enzyme stoichiometry, additional degrees of freedom of the DNA scaffold system include the number of repetitive scaffold units and the spacer length between the ZF binding sites. In the case of the $(1:1)_{16}$ resveratrol system, the largest product enhancement was observed for spacer lengths of 2 and especially 8 bp, while a spacer length of 4 bp showed a smaller yet measureable improvement over the unscaffolded enzymes (FIG. 6B). An even larger increase in titer enhancement of nearly 5-fold was observed when the number of scaffold repeats was decreased from 16 to 4 (FIG. 2B). These improvements highlight the ability to impact resveratrol production via simple changes in scaffold design that may lead in some cases to optimal arrangements of the enzymes on the DNA. Next, whether the enhanced product titers were dependent upon the close proximity (2-8 bp) of the two pathway enzymes was examiner. To test this notion, the ZF binding sites within the $(1:1)_4$ scaffold were separated on the plasmid by either 2 bp or 850 bp. The latter configuration provided the same number of binding sites on the plasmid for both enzymes but prevented the bound enzymes from localizing in close proximity to one another. It is important to note here that no changes were made to either of the chimeric enzymes. As would be expected for a proximity effect, the 5-fold enhancement in resveratrol production observed for the $(1:1)_4$ scaffold was abolished when the binding sites for each enzyme were positioned far apart on the plasmid (FIG. 6B).

Figure 6C:
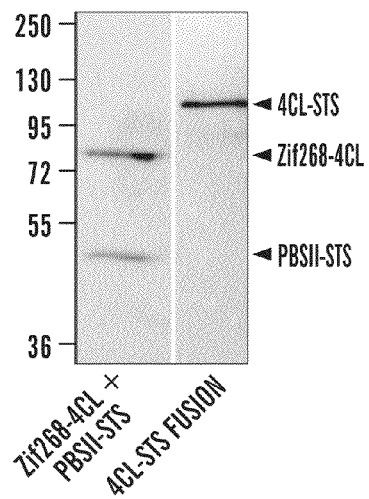

An alternative strategy for enzyme co-localization using a 4CL-STS fusion protein which was previously reported to increase resveratrol production in yeast up to ~6-fold was also evaluated (Zhang et al., "Using Unnatural Protein Fusions to Engineer Resveratrol Biosynthesis in Yeast and Mammalian Cells," *J. Am. Chem. Soc.* 128:13030-13031 (2006), which is hereby incorporated by reference in its entirety). In *E. coli*, however, the $(1:1)_{16}$ scaffold system produced >50 times more resveratrol than the 4CL-STS fusion (FIG. 6B), even though bacterial growth was very similar in both cases and the 4CL-STS fusion protein was expressed at an equal or slightly higher level than both the ZF-enzyme chimeras (FIG. 6C). This result may be due to the propensity of multidomain fusion proteins to misfold (and hence be less active) in *E. coli* (Chang et al., "De Novo Folding of GFP Fusion Proteins: High Efficiency in Eukaryotes but Not in Bacteria," *J. Mol. Biol.* 353:397-409 (2005), which is hereby incorporated by reference in its entirety) and highlights the advantage of the DNA assembly strategy whereby each of the ZF-enzyme fusions fold independently.

Example 3

Improving the Metabolic Performance of a Three-Enzyme Pathway for 1,2-PD

Figure 7A:
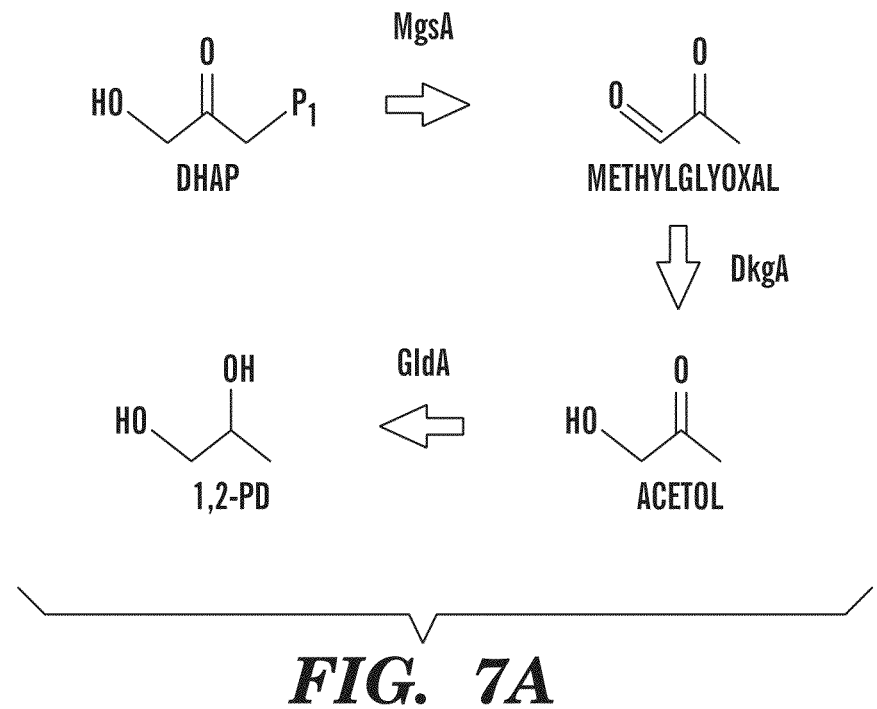
FIGS. 7A-7C depict DNA scaffold-assisted production of 1,2-PD.
Figure 7B:
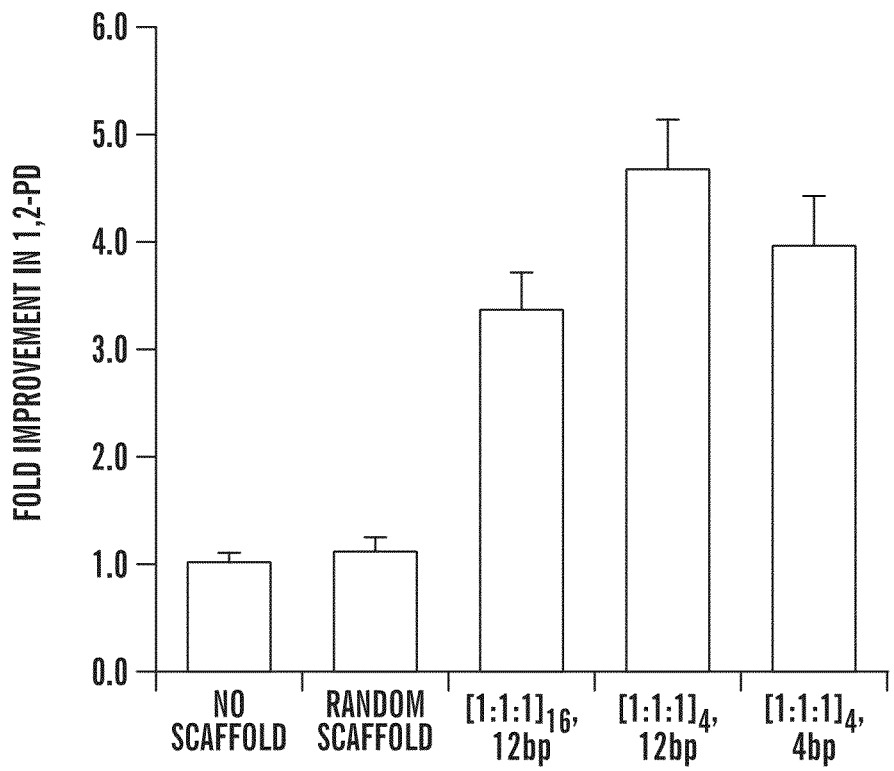

To test the generality of the system, a three-enzyme pathway for producing 1,2-PD from dihydroxyacetone phosphate (DHAP) was tested (FIG. 7A). This pathway was chosen because a biosynthetic route for 1,2-PD in *E. coli* is well established (Altaras & Cameron, "Metabolic Engineering of a 1,2-Propanediol Pathway in *Escherichia coli*," *Appl. Environ. Microbiol.* 65:1180-1185 (1999), which is hereby incorporated by reference in its entirety). For targeting the 1,2-PD metabolic pathway enzymes to DNA, methylglyoxal synthase (MgsA), 2,5-diketo-d-gluconic acid reductase (DkgA) and glycerol dehydrogenase (GldA) (all from *E. coli*) were fused to the N-termini of ZFa, ZFb and ZFc, respectively. For the scaffold design, target DNA sequences corresponding to each of the ZF domains were placed on the same plasmid as the ZF-enzyme chimeras. Given that there are approximately 127 plasmids per cell and approximately 5000 ZF-enzyme chimeras per cell (FIG. 4A), DNA scaffolds for the three-enzyme pathway were designed that would provide enough binding sites to accommodate all of the expressed enzymes. Specifically, scaffolds with enzyme:scaffold ratios in the range of 40:1 to 1:3 [$(1:1:1)_1$ to $(1:4:2)_{32}$, respectively] were constructed and tested. Like the resveratrol results above, *E. coli* with the $(1:1:1)_{16}$ 1,2-PD system produced ~3.5 times more 1,2-PD than cells expressing the ZF-enzyme fusions in the presence of no scaffold or a random scaffold control (FIG. 7B). Moreover, the growth rate of the cells in all of these cases was nearly identical. Also similar to the resveratrol results was the observation that protein fusions including MgsA-DkgA, DkgA-GldA and MgsA-DkgA-GldA did not improve 1,2-PD titers over the unscaffolded enzymes. Interestingly, when the number of scaffold unit repeats, n, was reduced from 16 to 4, 1,2-PD titers increased to approximately 4.5-fold above the unscaffolded controls. Here, only a small drop-off in metabolic performance was observed when the spacing between ZF binding sites was reduced from 12 to 4 bp for the $(1:1:1)_4$ scaffold.

Figure 8A:
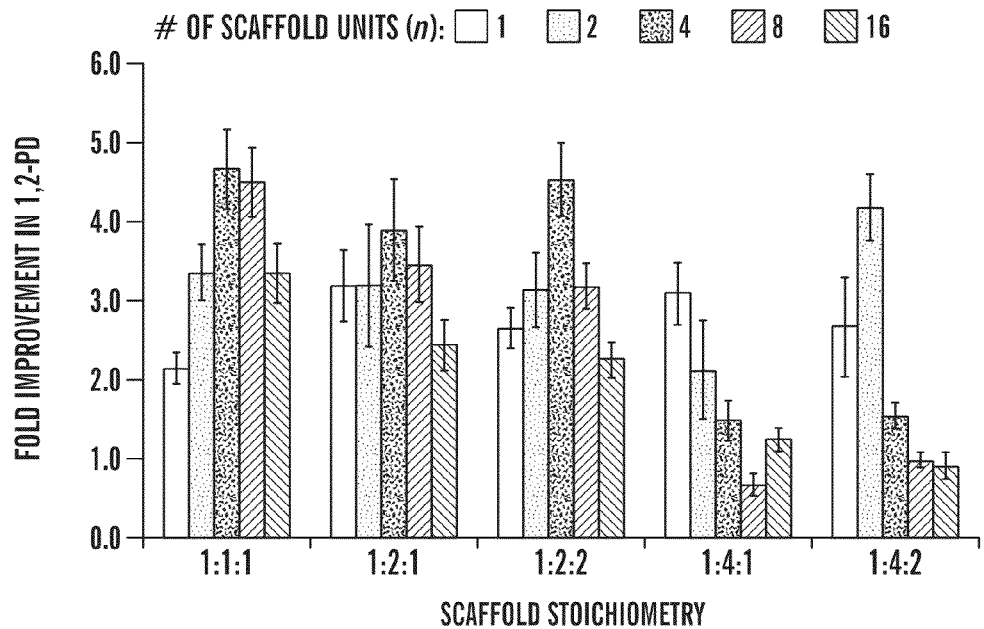
FIGS. 8A-8B depict the impact of different scaffold architectures on 1,2-PD production. 1,2-PD titers from E. coli cells expressing the MgsA-ZFa, DkgA-ZFb and GldA-ZFc chimeras in the presence of different $[a:b:c]_n$ scaffolds as indicated where the spacing was 12 bp (FIG. 8A) or 4 bp (FIG. 8B). Cells expressing the ZF-enzyme chimeras in the presence of a random scaffold served as the control to which all data was normalized. The amount of 1,2-PD produced in the random scaffold control cells was 0.13±0.01 g/L. Data are the average of three replicate experiments and error bars are the SEM.
Figure 8B:
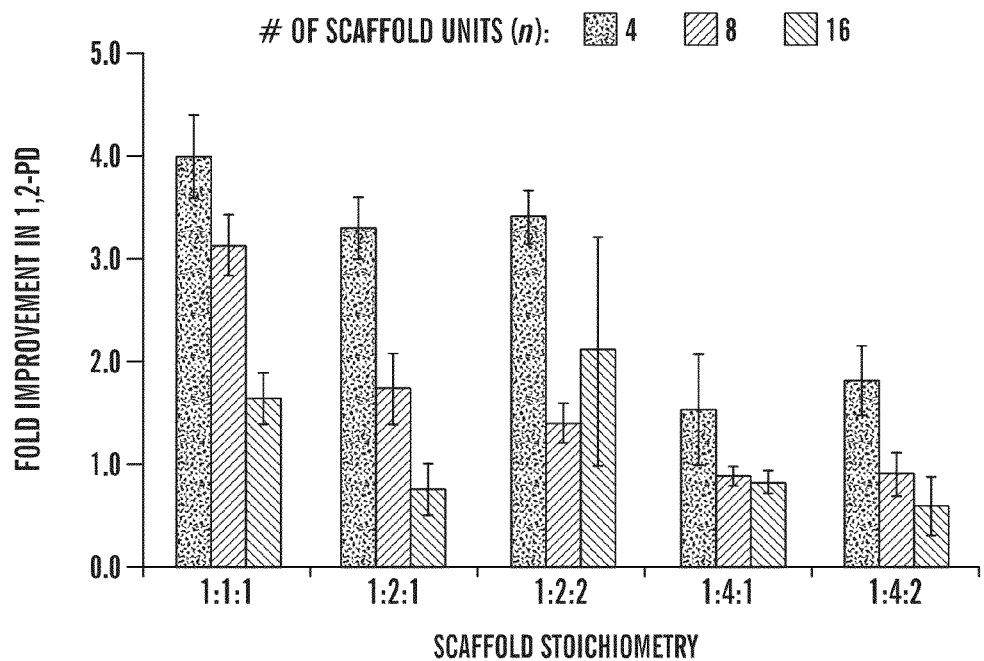

To systematically investigate the relationship between scaffold design variables and product formation, a matrix of additional plasmid-encoded DNA scaffolds was generated where a was always 1, while b and c were varied to give the following stoichiometries: 1:1:1, 1:2:1, 1:2:2, 1:4:1 and 1:4:2. The number of scaffold units, n, was varied to be 1, 2, 4, 8, 16 or 32 and the spacing between ZF binding sites was either 4 or 12 bp. It should also be noted that the first pathway enzyme, MgsA, was flanked on each side by the second and third pathway enzymes, giving rise to a bidirectional pathway arrangement (FIG. 3B). To determine the impact of these designs, *E. coli* cells were transformed with plasmids encoding the ZF-enzyme chimeras and the different scaffolds. Nearly all of the scaffolds with 12-bp spacers between ZF binding sites were observed to enhance 1,2-PD production (FIG. 8A). In particular, the $[1:1:1]_4$, $[1:1:1]_8$, $[1:2:1]_4$, $[1:2:2]_4$, and $[1:4:2]_2$ scaffolds each increased 1,2-PD levels by ~4-5 fold compared to the unscaffolded control. These data also revealed that when only a single scaffold unit was present (n=1), product titers were largely insensitive to the scaffold stoichiometry. However, as the number of scaffold units was increased, the effect of scaffold stoichiometry on 1,2-PD levels became more varied. Nearly all scaffolds with 4-bp spacers between ZF binding sites were less effective than their 12-bp counterparts at improving 1,2-PD titers (FIG. 8B).

Figure 7C:
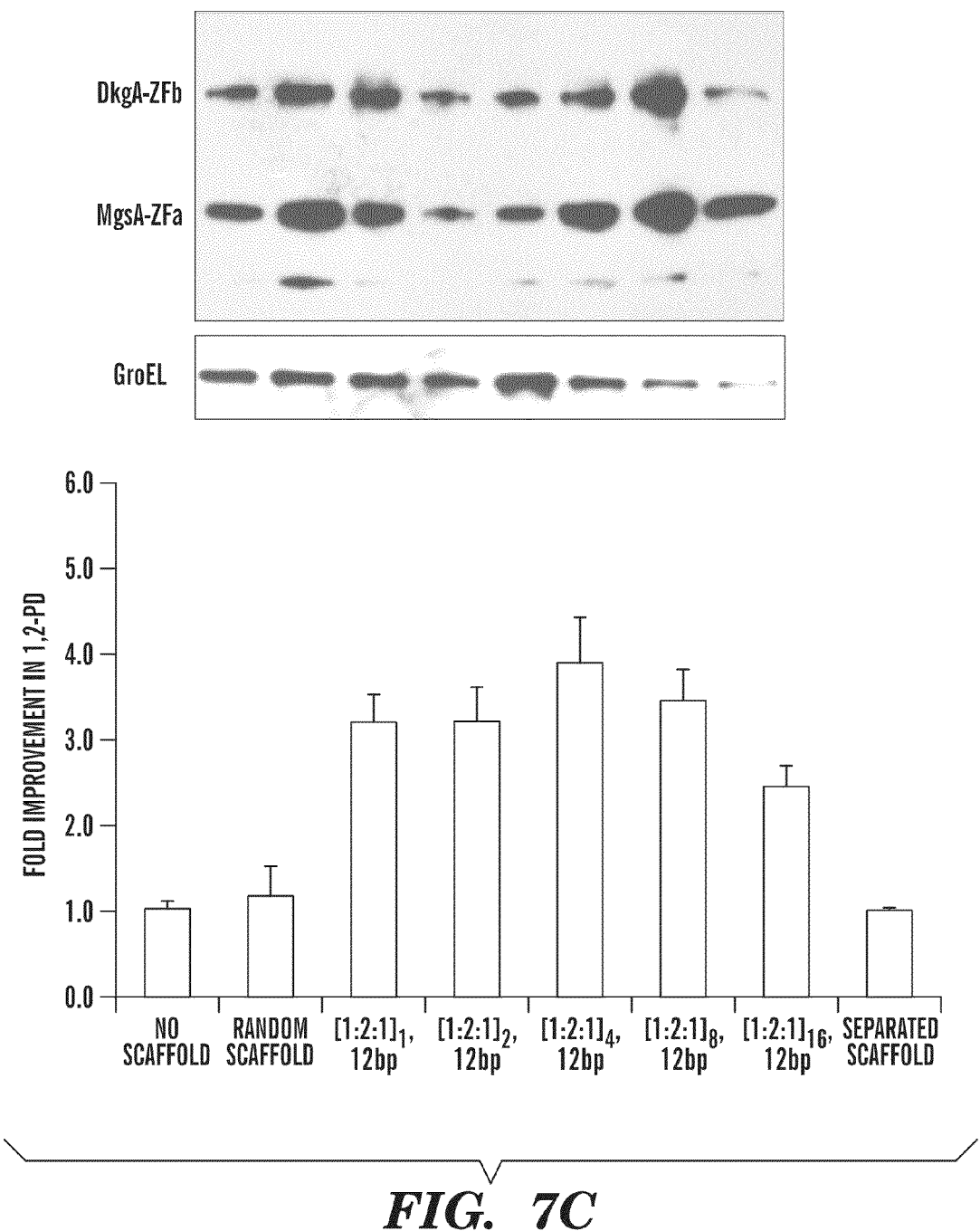

To investigate the factors underlying the observed enhancement of 1,2-PD production, the cellular expression levels of ZF-enzyme chimeras were measured in the presence of different DNA scaffolds. Regardless of whether the cells carried a $(1:2:1)_n$ scaffold, a random scaffold sequence or lacked a scaffold altogether, the expression level of these chimeras were all very similar with the exception of cells carrying the $(1:2:1)_2$ and $(1:2:1)_4$ scaffolds, which appeared to accumulate slightly lower levels of MgsA-ZFa and DkgA-ZFb enzymes (FIG. 7C). However, this lower expression on it's own was insufficient to explain the improved 1,2-PD titers conferred by these scaffolds. This is because the $(1:2:1)_1$ and the $(1:2:1)_8$ scaffolds showed similar enhancements in 1,2-PD titers but with enzyme expression levels that were nearly indistinguishable from the unscaffolded controls. Therefore, a simple change in cellular enzyme levels is not the cause of the DNA scaffold-guided enhancement of 1,2-PD levels. To test whether enzyme proximity was important for enhanced 1,2-PD titers, the ZF binding sites within the $(1:2:1)_2$ scaffold were separated on the plasmid by ~1000 bp. As seen above for resveratrol production, the enhancement in 1,2-PD production was abolished when the binding sites for each enzyme were positioned far apart on the plasmid (FIG. 7C). Hence, the relative proximity of the enzymes appears to be a key factor underlying the observed titer enhancements.

Example 4

Extending DNA Scaffolds to Mevalonate Production

Figure 9A:
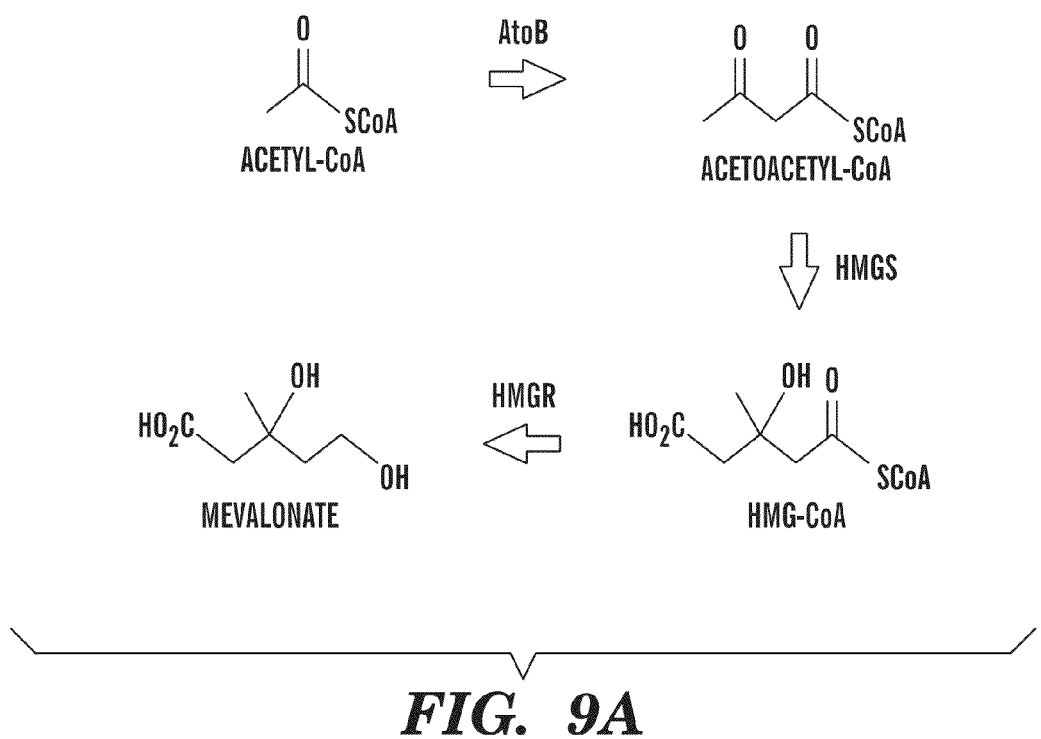
FIGS. 9A-9B show DNA scaffold-assisted production of mevalonate.
Figure 9B:
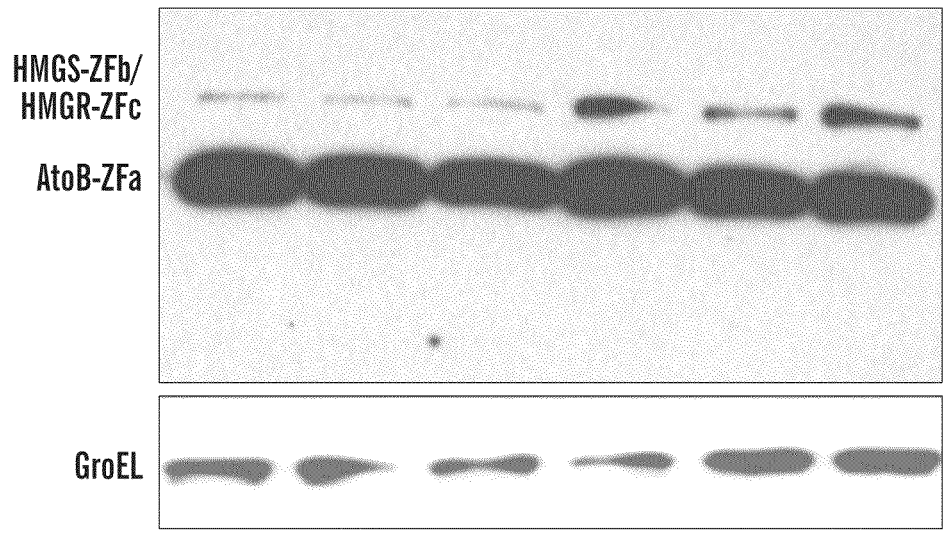
Figure 9B:
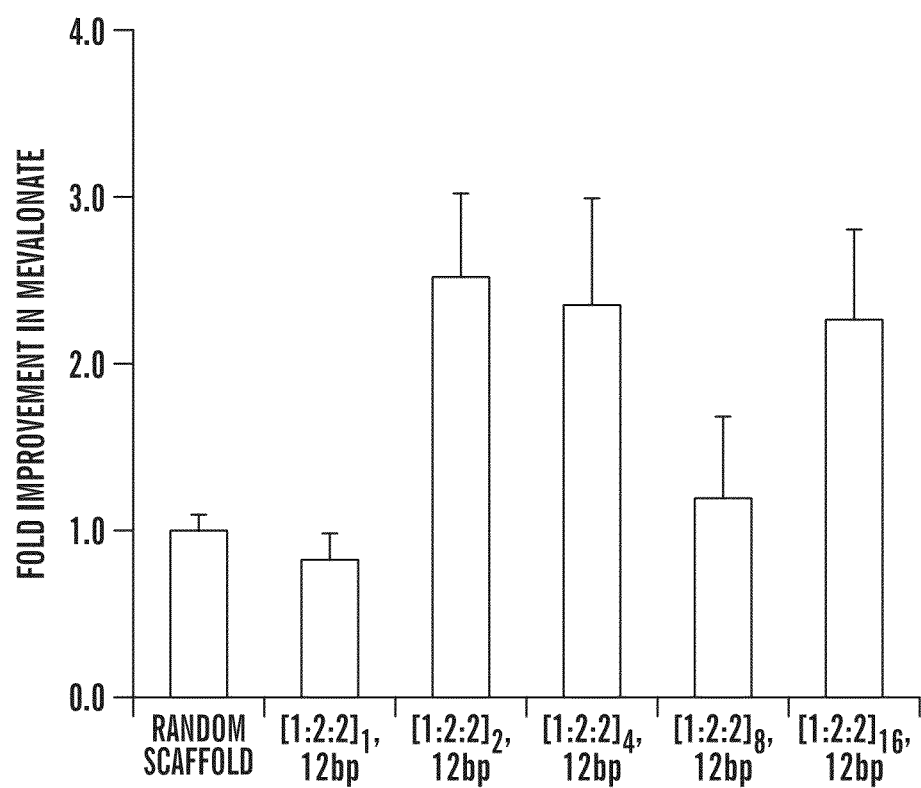
Figure 10A:
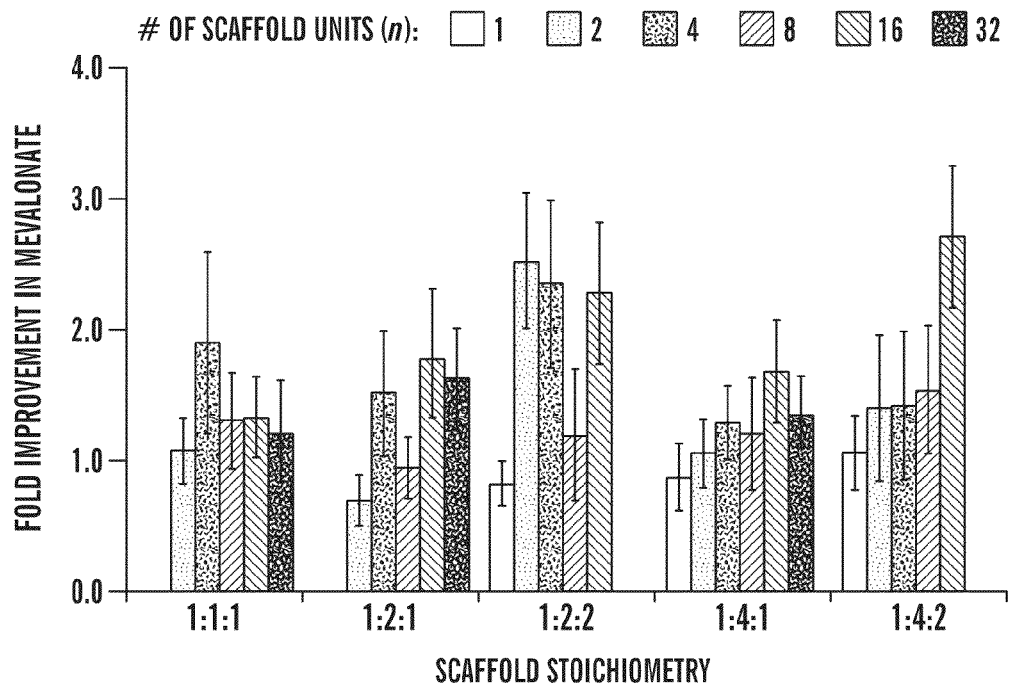
FIGS. 10A-10B show the impact of different scaffold architectures on mevalonate production. Mevalonate titers from E. coli cells expressing the AtoB-ZFa, HMGS-ZFb and HMGR-ZFc chimeras in the presence of different [a:b:c]n scaffolds as indicated where the spacing was 12 bp (FIG. 10A) or 4 bp (FIG. 10B). Cells expressing the ZF-enzyme chimeras in the presence of a random scaffold served as the control to which all data was normalized. The amount of mevalonate produced in the random scaffold control cells was 1.7±0.07 g/L. Data are the average of three replicate experiments and error bars are the SEM.
Figure 10B:
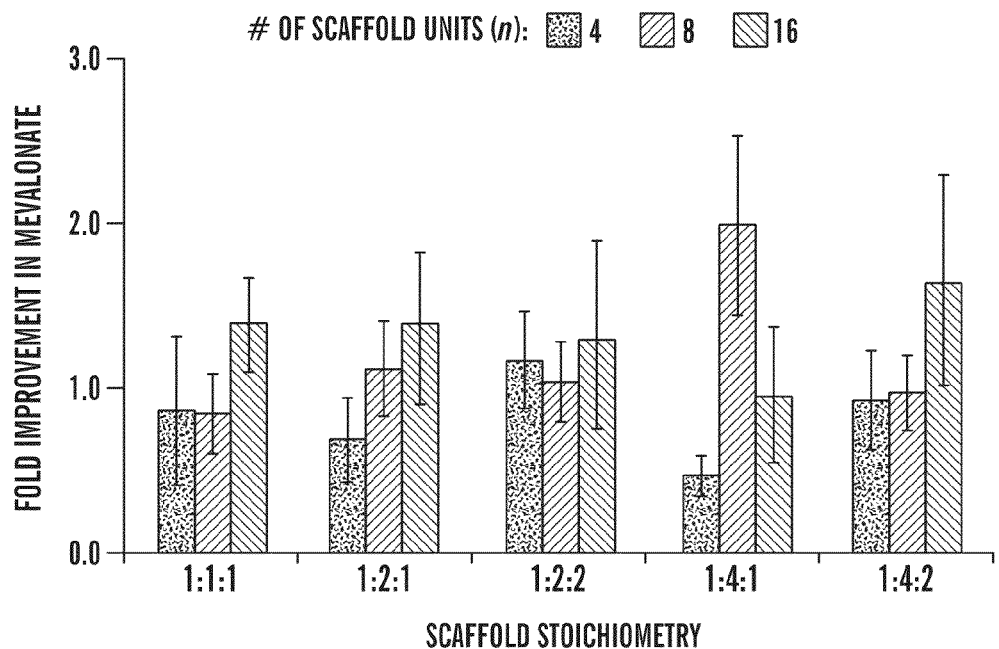

As a final test of the generality of the system, the DNA scaffolds were used to improve mevalonate production. This pathway was chosen because production of mevalonate from acetyl-CoA in *E. coli* has been described (FIG. 9A) (Martin et al., "Engineering a Mevalonate Pathway in *Escherichia coli* for Production of Terpenoids," *Nat. Biotechnol.* 21:796-802 (2003), which is hereby incorporated by reference in its entirety). Furthermore, as mentioned above, previous studies demonstrated that assembly of the mevalonate biosynthetic enzymes on a protein scaffold caused cells to accrue significantly higher titers of mevalonate (Dueber et al., "Synthetic Protein Scaffolds Provide Modular Control Over Metabolic Flux," *Nat. Biotechnol.* 27:753-759 (2009), which is hereby incorporated by reference in its entirety); therefore, this pathway allows direct comparison between the DNA scaffolds and earlier protein-based scaffolds. ZF-enzyme chimeras were created by fusing the mevalonate biosynthetic enzymes E. coli acetoacetyl-CoA thiolase (AtoB), Saccharomyces cerevisiae hydroxy-methylglutaryl-CoA synthase (HMGS) and S. cerevisiae hydroxy-methylglutaryl-CoA reductase (HMGR) to the N-termini of ZFa, ZFb and ZFc, respectively. For the scaffold design, target DNA sequences corresponding to each of the ZF domains were placed on a separate plasmid. Similar to the resveratrol and 1,2-PD cases above, mevalonate titers were increased 2- to 3-fold in the presence of several different scaffold designs (FIG. 10A). While no clear trend was apparent, the greatest titer enhancement—an increase of nearly 3-fold—came from the $(1:4:2)_{16}$ scaffold. This was followed closely by several of the $(1:2:2)_n$ scaffolds (i.e. n=2, 4 and 16) that each enhanced mevalonate titers by ~2.5 fold compared to the random scaffold control (FIG. 9B). The fact that the best yield enhancement using protein-based scaffolds also came from a 1:2:2 motif (Dueber et al., "Synthetic Protein Scaffolds Provide Modular Control Over Metabolic Flux," *Nat. Biotechnol.* 27:753-759 (2009), which is hereby incorporated by reference in its entirety) suggests that this arrangement may be optimal for balancing pathway flux. Consistent with the results above for 1,2-PD, the smaller 4-bp spacers between the ZF binding sites resulted were less effective than their 12-bp counterparts at improving metabolic performance (FIG. 10B). In fact, most scaffolds containing 4-bp spacers resulted in little to no enhancement of mevalonate titers compared to unscaffolded enzymes. Finally, while the expression levels of the ZF-enzyme chimeras were largely unaffected by the presence or absence of a specific DNA scaffold, the amount of AtoB-ZFa that accumulated in cells was much greater compared to the HMGS-ZFb/HMGR-ZFc chimeras (FIG. 9B). In contrast, the expression levels of the ZF-enzyme chimeras for 1,2-PD were more evenly balanced, which might account for the generally larger fold improvements seen for the production of 1,2-PD versus mevalonate. These data suggest that more balanced expression of the ZF-enzyme chimeras may further increase mevalonate titers in the future.

Discussion of Examples 1-4

The Examples above demonstrate that DNA scaffold-assisted biosynthesis is a viable strategy for significantly enhancing the titers of three diverse metabolic products. This enhancement appears to arise from the enforced proximity of metabolic enzymes that likely increases the effective concentrations of intermediary metabolites. In every case tested, DNA scaffold-assisted biosynthesis was implemented on an existing microbial metabolic pathway and did not require any a priori knowledge about the structure or function of any of the underlying biosynthetic enzymes, making the implementation of this new approach simple and generalizable to virtually any pathway. This was made possible by the ability to fuse distinct ZF domains to diverse protein targets at will without significant loss of the ZF domains' DNA binding activity or the target proteins' enzymatic activity. As a result, this is the first ever report of DNA as an intracellular scaffold for controlling the flow of information in a metabolic or signaling context.

It should be pointed out that scaffolds comprising expressed proteins and RNAs have recently been reported that have been used for directing new cell signaling behaviors (Bashor et al., "Using Engineered Scaffold Interactions to Reshape MAP Kinase Pathway Signaling Dynamics," *Science* 319:1539-1543 (2008); Park et al., "Rewiring MAP Kinase Pathways Using Alternative Scaffold Assembly Mechanisms," *Science* 299:1061-1064 (2003), which are hereby incorporated by reference in their entirety) and linking together metabolic enzymes to more efficiently synthesize desired chemical products (Dueber et al., "Synthetic Protein Scaffolds Provide Modular Control Over Metabolic Flux," *Nat. Biotechnol.* 27:753-759 (2009); Delebecque et al., "Organization of Intracellular Reactions With Rationally Designed RNA Assemblies," *Science* 333:470-474 (2011), which is hereby incorporated by reference in its entirety). Compared to these systems, DNA scaffolds present a number of unique challenges and opportunities for improvement. For example, much larger titer enhancements were observed with both protein- and RNA-based scaffolds (>50-fold) compared to DNA scaffolds (up to ~5-fold). In the case of protein scaffolds, however, the largest titer enhancements (77-fold) were observed only under conditions where enzyme expression levels were very low. When saturating amounts of the inducer were used, which were on par with the inducer concentration used in our studies (i.e. ~250 nM anhydrotetracycline), the scaffold-dependent increases in mevalonate titers decreased to levels that were similar to or even below those observed here. Furthermore, when protein scaffolds were applied to a second metabolic system, namely glucaric acid production, the improvement was ~2-5 fold (Dueber et al., "Synthetic Protein Scaffolds Provide Modular Control Over Metabolic Flux," *Nat. Biotechnol.* 27:753-759 (2009); Moon et al., "Use of Modular, Synthetic Scaffolds for Improved Production of Glucaric Acid in Engineered *E. coli*," *Metab. Eng.* 12:298-305 (2010), which are hereby incorporated by reference in their entirety), which was consistent with the improvements achieved with DNA scaffolds. In the case of RNA scaffolds, studies were focused on just a single metabolic system, namely biohydrogen production. Thus, whether such a large titer enhancement can be generalized to other pathways remains to be shown. A potential drawback of DNA scaffolds is that the placement of repetitive sequences in plasmid DNA may result in recombination of the plasmid to remove the repeat regions. To date, however, numerous DNA sequencing and restriction digestion analysis experiments have been performed and there is no evidence of plasmid recombination under any of the conditions tested. Nonetheless, a recA⁻ strain background in which recombination events are minimized could be used as the scaffolding host. Another challenge associated with plasmid DNA is its tendency to become supercoiled in cells. Plasmid supercoiling may restrict the ability to spatially control enzyme orientation especially over long distances. In contrast, the use of RNA permits the assembly of discrete one- and two-dimensional scaffolds (Delebecque et al., "Organization of Intracellular Reactions With Rationally Designed RNA Assemblies," *Science* 333:470-474 (2011), which is hereby incorporated by reference in its entirety). However, with the recent development of methods for rationally designing DNA nanostructures with complex secondary structures that assemble in the cytoplasm of *E. coli* (Lin et al., "In Vivo Cloning of Artificial DNA Nanostructures," *Proc. Nat'l. Acad. Sci. U.S.A.* 105: 17626-17631 (2008), which is hereby incorporated by reference in its entirety), it may be possible in the future to create nanostructured DNA scaffolds in vivo that permit exquisite patterning of target proteins.

Despite some of these challenges, the ultra-stable nature of DNA and its ability to support locally ordered scaffolds, here up to 2.4 kb with over 150 individual ZF binding sites, will enable scalability of DNA scaffolds to large metabolic systems (i.e. comprising more than three enzymes and/or more than one pathway) arranged in virtually any stoichiometry and repeated many times over. Another major advantage of DNA scaffolds is their modularity, which permits a very high degree of freedom with respect to important system variables such as: stoichiometry of enzyme binding sites, number of scaffold units (n), spacing of ZF binding sites, location of binding sites on the plasmid, copy number of the plasmid, and binding affinity of the ZF domain for the DNA target sequence. The number of tunable parameters that can be used to advantageously tailor a metabolic system increases dramatically if one also considers the range of modifications that can be made to the ZF-enzyme fusion (e.g. N- or C-terminal attachment of ZF domain, length and composition of the linker connecting ZF domain to the enzyme, sequence of the ZF domain, etc.). By studying different DNA scaffold architectures, enzyme stoichiometries, and flux balanced or imbalanced scenarios, it should be possible to determine when enzyme co-localization is most beneficial. This, in turn, will be very useful for guiding future design of these systems and in envisioning new applications for enzyme co-localization. The DNA scaffold approach described here is highly complementary to many of the existing methods for enzyme, pathway and strain engineering that are already in the cellular engineer's toolkit. Hence, a successful strategy for achieving the production yields, near theoretical maximum, necessary for industrial viability will likely involve a combination of these approaches. Of course, DNA scaffolds could also be used to flexibly control the flow of different classes of biological information that extend beyond metabolic pathways and small-molecule products. For example, DNA scaffolds could be used to rewire intracellular signaling pathways or to coordinate other assembly-line processes such as protein folding, degradation and post-translational modifications. Thus, DNA scaffolds should enable the construction of reliable protein networks to program a range of useful cellular behaviors. Even though the beauty of nature's most elegant compartmentalization strategies such as a protected tunnel (Hyde et al., "Three-Dimensional Structure of the Tryptophan Synthase $\alpha_2\beta_2$ Multienzyme Complex From *Salmonella typhimurium*," *J. Biol. Chem.* 263:17857-17871 (1988), which is hereby incorporated by reference in its entirety) or intracellular organelles (Bobik T. A., "Polyhedral Organelles Compartmenting Bacterial Metabolic Processes," *Appl. Microbiol. Biotechnol.* 70:517-525 (2006); Straight et al., "A Singular Enzymatic Megacomplex From *Bacillus subtilis*," *Proc. Nat'l. Acad. Sci. U.S.A.* 104:305-310 (2007), which are hereby incorporated by reference in their entirety) have yet to be recapitulated by engineers, the use of DNA scaffolds is an important early step towards this goal.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A synthetic deoxyribonucleic acid scaffold comprising one or more subunits, each subunit comprising two or more different protein-binding sequences separated by at least one nucleic acid spacer, wherein the at least one nucleic acid spacer comprises no more than 850 base pairs, and wherein the two or more different protein-binding sequences comprise a first, second, and third protein-binding sequence, wherein the first protein-binding sequence is flanked on both sides by the second and third protein-binding sequences in a bidirectional pathway arrangement.

2. The synthetic deoxyribonucleic acid scaffold of claim 1 wherein the two or more different protein-binding sequences are zinc-finger protein binding sequences.

3. The synthetic deoxyribonucleic acid scaffold of claim 2, wherein the one or more subunits are repeated two or more times.

4. A nucleic acid vector comprising the synthetic deoxyribonucleic acid scaffold of claim 2.

5. host cell comprising the synthetic deoxyribonucleic acid scaffold of claim 2.

6. The host cell of claim 5, wherein the host cell is selected from the group consisting of an animal cell, insect cell, plant cell, bacterial cell, fungal cell, and synthetic cell.

7. A system comprising:
a substrate of an enzymatic reaction;
two or more chimeric enzyme proteins involved in said enzymatic reaction, each chimeric enzyme protein comprising an enzyme portion coupled to a heterologous DNA binding portion;
a synthetic deoxyribonucleic acid scaffold comprising one or more subunits, each subunit comprising two or more different protein-binding sequences separated by at least one nucleic acid spacer, wherein the at least one nucleic acid spacer comprises no more than 850 base pairs, wherein the two or more different protein-binding sequences comprise a first, second, and third protein-binding, sequence, wherein the first protein-binding, sequence is flanked on both sides by the second and third protein-binding sequences in a bidirectional pathway arrangement, wherein the two or more different protein-binding sequences are binding partners with the DNA binding portions of the two or more chimeric enzyme proteins, and wherein the protein binding sequences of the deoxyribonucleic acid scaffold are spatially assembled within a subunit to allow a series of sequential reactions involving the substrate and the two or more chimeric enzyme proteins when the DNA binding portions of two or more chimeric enzyme proteins are bound to their corresponding protein binding sequences of the deoxyribonucleic acid scaffold; and
a host cell, wherein the substrate of the enzymatic reaction, the two or more chimeric enzyme proteins, and the synthetic deoxyribonucleic acid scaffold are present within the host cell.

8. The system of claim 7, wherein the heterologous DNA binding portions of the chimeric enzyme proteins comprise zinc finger DNA binding domains and the protein binding sequences of the synthetic deoxyribonucleic acid scaffold comprise zinc finger protein binding sequences.

9. The system of claim 8, wherein the zinc, finger DNA binding domain portion of cacti of the two or more chimeric enzyme proteins is different.

10. The system of claim 8, wherein the enzyme portion of each of the two or more chimeric enzyme proteins is coupled to its respective zinc finger DNA binding domain portion via a polypeptide linker sequence.

11. The system of claim 8, wherein the enzyme portion of each of the two or more enzyme proteins is coupled to its respective zinc finger DNA binding domain portion via its amino-terminus or its carboxy-terminus.

12. The system of claim 8, wherein the one or more subunits of the synthetic deoxyribonucleic acid scaffold are repeated two or more times.

13. The system of claim 8, wherein the two or more chimeric enzyme proteins comprise enzymes of a biosynthetic reaction.

14. The system of claim 8, wherein the two or more chimeric enzyme proteins comprise enzymes of a metabolic reaction.

15. The system of claim 8, wherein the two or more chimeric enzyme proteins comprise enzymes involved in protein folding.

16. The system of claim 8, wherein the two or more chimeric enzyme proteins comprise enzymes involved in a protein degradation reaction.

17. The system of claim 8, wherein the two or more chimeric enzyme proteins comprise enzymes of a post-translational modification reaction.

18. The system of claim 7, wherein the host cell is selected from the group consisting of an animal cell, insect cell, plant cell, bacterial cell, fungal cell, and synthetic cell.

19. A method for assembling a synthetic enzymatic reaction pathway comprising:
providing two or more chimeric enzyme proteins involved in said enzymatic reaction pathway, each chimeric enzyme protein comprising an enzyme portion coupled to a heterologous DNA binding portion;
providing a synthetic deoxyribonucleic acid scaffold comprising one or more subunits, each subunit comprising two or more different protein-binding sequences separated by at least one nucleic acid spacer, wherein the at least one nucleic acid spacer comprises no more than 850 base pairs, wherein the two or more different protein-binding sequences comprise a first, second, and third protein-binding sequence, wherein the first protein-binding sequence is flanked on both sides by the second and third protein-binding sequences in a bidirectional pathway arrangement, wherein the two or more different protein-binding sequences are binding partners with the DNA binding portions of the two or more chimeric enzyme proteins, and wherein the protein binding sequences of the deoxyribonucleic acid scaffold are spatially assembled within a subunit to allow a series of sequential reactions involving a substrate of the enzymatic reaction pathway and the two or more chimeric enzyme proteins when the DNA binding, portions of two or more chimeric enzyme proteins are bound to their corresponding protein binding sequences of the deoxyribonucleic acid scaffold; and contacting the two or more chimeric enzyme proteins and the synthetic deoxyribonucleic acid scaffold under conditions effective for the DNA binding portions of the two or more chimeric enzyme proteins to bind to their corresponding protein-binding sequences on the synthetic deoxyribonucleic acid scaffold thereby assembling the synthetic enzymatic reaction pathway.

20. The method of claim 19, wherein the heterologous DNA binding portions of the chimeric enzyme proteins comprise zinc finger DNA binding domains and the protein binding sequences of the synthetic deoxyribonucleic acid scaffold comprise zinc finger protein binding sequences.

21. The method of claim 20, wherein the zinc finger DNA binding domain portion of each of the two or more chimeric enzyme proteins is different.

22. The method of claim 20, wherein the one or more subunits of the synthetic deoxyribonucleic acid scaffold are repeated two or more times.

23. The method of claim 19 further comprising:
producing an enzymatic reaction pathway product or an enzymatic reaction pathway product precursor of the assembled synthetic enzymatic reaction pathway after said contacting wherein said producing comprises:

providing a substrate of the enzymatic reaction pathway and contacting the substrate with the assembled enzymatic reaction pathway under conditions effective for a sequential reaction between the substrate and the two or more chimeric enzyme proteins of the assembled synthetic enzymatic reaction pathway.

24. The method of claim 23, wherein the two or more chimeric enzyme proteins and the synthetic deoxyribonucleic acid scaffold are present together in a host cell and said contacting occurs within the host cell.

25. The method of claim 24, wherein the host cell is selected from the group consisting of an animal cell, insect cell, plant cell, bacterial cell, fungal cell, and synthetic cell.

26. The synthetic deoxyribonucleic acid scaffold of claim 1, wherein the scaffold is a plasmid deoxyribonucleic acid scaffold.

27. The system of claim 7, wherein the synthetic deoxyribonucleic acid scaffold is a plasmid deoxyribonucleic acid scaffold.

28. The method of claim 19, wherein the synthetic deoxyribonucleic acid scaffold is a plasmid deoxyribonucleic acid scaffold.

29. The synthetic deoxyribonucleic acid scaffold of claim 1 wherein the scaffold comprises two or more different protein-binding sequences that encode two or more chimeric enzyme proteins on a single construct.

* * * * *